(12) United States Patent
Scheer et al.

(10) Patent No.: US 9,637,557 B2
(45) Date of Patent: May 2, 2017

(54) PRODUCTION OF HETEROMULTIMERIC PROTEINS

(75) Inventors: Justin Scheer, San Francisco, CA (US); Christoph Spiess, Los Altos, CA (US); Daniel G. Yansura, Pacifica, CA (US)

(73) Assignee: Genentech, Inc., South San Francisco, CA (US)

(*) Notice: Subject to any disclaimer, the term of this patent is extended or adjusted under 35 U.S.C. 154(b) by 1431 days.

(21) Appl. No.: 13/092,708

(22) Filed: Apr. 22, 2011

(65) Prior Publication Data

US 2011/0287009 A1 Nov. 24, 2011

Related U.S. Application Data

(60) Provisional application No. 61/327,302, filed on Apr. 23, 2010.

(51) Int. Cl.
| | |
|---|---|
| *C07K 16/00* | (2006.01) |
| *C07K 16/46* | (2006.01) |
| *C07K 16/24* | (2006.01) |
| *C07K 16/28* | (2006.01) |
| *C07K 16/30* | (2006.01) |
| *A61K 39/00* | (2006.01) |

(52) U.S. Cl.
CPC .......... *C07K 16/468* (2013.01); *C07K 16/244* (2013.01); *C07K 16/247* (2013.01); *C07K 16/2863* (2013.01); *C07K 16/30* (2013.01); *A61K 2039/505* (2013.01); *C07K 2317/31* (2013.01); *C07K 2317/526* (2013.01); *C07K 2317/73* (2013.01); *C07K 2317/76* (2013.01); *C07K 2317/90* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,120,649 A | 10/1978 | Schechter | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,533 A | 3/1982 | Barré | |
| 4,317,821 A | 3/1982 | Miyashita et al. | |
| 4,322,348 A | 3/1982 | Asai et al. | |
| 4,331,598 A | 5/1982 | Hasegawa et al. | |
| RE30,985 E | 6/1982 | Cartaya | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,419,446 A | 12/1983 | Howley et al. | |
| 4,424,219 A | 1/1984 | Hashimoto et al. | |
| 4,450,254 A | 5/1984 | Isley et al. | |
| 4,560,655 A | 12/1985 | Baker | |
| 4,601,978 A | 7/1986 | Karin | |
| 4,657,866 A | 4/1987 | Kumar | |
| 4,665,077 A | 5/1987 | Stringfellow et al. | |
| 4,767,704 A | 8/1988 | Cleveland et al. | |
| 4,816,567 A | 3/1989 | Cabilly et al. | |
| 4,927,762 A | 5/1990 | Darfler | |
| 4,965,199 A | 10/1990 | Capon et al. | |
| 4,975,278 A | 12/1990 | Senter et al. | |
| 5,053,394 A | 10/1991 | Ellestad et al. | |
| 5,114,721 A | 5/1992 | Cohen et al. | |
| 5,122,469 A | 6/1992 | Mather et al. | |
| 5,143,844 A | 9/1992 | Abrahmsen et al. | |
| 5,208,020 A | 5/1993 | Chari et al. | |

(Continued)

FOREIGN PATENT DOCUMENTS

| | | |
|---|---|---|
| EP | 0 340 109 B1 | 11/1989 |
| EP | 0 404 097 B1 | 12/1990 |

(Continued)

OTHER PUBLICATIONS

Karawajew et al (HBT, 31:367-368, 1987).*
Shin et al (B&B, 101(6):1288-1296, 2008).*
Merchant et al, Nature Biotech., 16,):677-681, 1998.*
Labrijn et al, Nature Biotech., 27(8):767-771, 2009.*
Bachmann., "Derivations and Genotypes of Some Mutant Derivatives of *Escherichia coli* K-12." *Escherichia coli* and *Salmonella Typhimurium*: Cellular and Molecular Biology. (Washington, DC: American Society for Microbiology.), Chapter 72, 2:1190-1219 (1987).

(Continued)

*Primary Examiner* — Brad Duffy
(74) *Attorney, Agent, or Firm* — Morrison & Foerster LLP

(57) ABSTRACT

Described herein are methods for the efficient production of antibodies and other multimeric protein complexes (collectively referred to herein as heteromultimeric proteins) capable of specifically binding to more than one target. The targets may be, for example, different epitopes on a single molecule or located on different molecules. The methods combine efficient, high gene expression level, appropriate assembly, and ease of purification for the heteromultimeric proteins. The invention also provides methods of using these heteromultimeric proteins, and compositions, kits and articles of manufacture comprising these antibodies.

75 Claims, 43 Drawing Sheets

(56) References Cited

U.S. PATENT DOCUMENTS

| | | | |
|---|---|---|---|
| 5,264,356 A | 11/1993 | Rohrschneider | |
| 5,362,852 A | 11/1994 | Geoghegan | |
| 5,500,362 A | 3/1996 | Robinson et al. | |
| 5,508,192 A | 4/1996 | Georgiou et al. | |
| 5,591,828 A | 1/1997 | Bosslet et al. | |
| 5,635,483 A | 6/1997 | Pettit et al. | |
| 5,639,635 A | 6/1997 | Joly et al. | |
| 5,641,870 A | 6/1997 | Rinderknecht et al. | |
| 5,648,237 A | 7/1997 | Carter | |
| 5,663,149 A | 9/1997 | Pettit et al. | |
| 5,712,374 A | 1/1998 | Kuntsmann et al. | |
| 5,714,586 A | 2/1998 | Kunstmann et al. | |
| 5,731,168 A | 3/1998 | Carter et al. | |
| 5,739,116 A | 4/1998 | Hamann et al. | |
| 5,767,285 A | 6/1998 | Hamann et al. | |
| 5,770,701 A | 6/1998 | McGahren et al. | |
| 5,770,710 A | 6/1998 | McGahren et al. | |
| 5,773,001 A | 6/1998 | Hamann et al. | |
| 5,780,588 A | 7/1998 | Pettit et al. | |
| 5,807,706 A | 9/1998 | Carter et al. | |
| 5,821,337 A | 10/1998 | Carter et al. | |
| 5,844,093 A | 12/1998 | Kettleborough et al. | |
| 5,877,296 A | 3/1999 | Hamann et al. | |
| 6,027,888 A | 2/2000 | Georgiou et al. | |
| 6,083,715 A | 7/2000 | Georgiou et al. | |
| 6,129,914 A * | 10/2000 | Weiner et al. | 424/133.1 |
| 6,331,415 B1 | 12/2001 | Cabilly et al. | |
| 6,358,509 B1 | 3/2002 | Ramanthan et al. | |
| 6,534,628 B1 | 3/2003 | Nilsson et al. | |
| 6,660,843 B1 | 12/2003 | Feige et al. | |
| 6,835,809 B1 | 12/2004 | Liu et al. | |
| 6,919,426 B2 | 7/2005 | Boone et al. | |
| 6,979,556 B2 | 12/2005 | Simmons et al. | |
| 7,138,370 B2 | 11/2006 | Oliner et al. | |
| 7,183,076 B2 | 2/2007 | Arathoon et al. | |
| 7,205,275 B2 | 4/2007 | Oliner et al. | |
| 7,259,137 B2 | 8/2007 | Min et al. | |
| 7,332,474 B2 | 2/2008 | Min et al. | |
| 7,472,724 B2 | 1/2009 | Lester et al. | |
| 7,498,420 B2 | 3/2009 | Michaud et al. | |
| 7,501,121 B2 | 3/2009 | Tchistiakova et al. | |
| 7,612,181 B2 | 11/2009 | Wu et al. | |
| 7,615,213 B2 | 11/2009 | Kasaian et al. | |
| 7,642,228 B2 | 1/2010 | Carter et al. | |
| 7,674,459 B2 | 3/2010 | Fung et al. | |
| 2002/0004587 A1 | 1/2002 | Miller et al. | |
| 2003/0078385 A1 | 4/2003 | Arathoon et al. | |
| 2003/0176352 A1 | 9/2003 | Min et al. | |
| 2003/0195156 A1 | 10/2003 | Min et al. | |
| 2003/0229023 A1 | 12/2003 | Oliner et al. | |
| 2003/0236193 A1 | 12/2003 | Oliner et al. | |
| 2005/0136051 A1* | 6/2005 | Scallon | C07K 16/241 424/133.1 |
| 2005/0169933 A1 | 8/2005 | Steeves et al. | |
| 2005/0186208 A1 | 8/2005 | Fyfe et al. | |
| 2005/0238649 A1 | 10/2005 | Doronina et al. | |
| 2006/0204493 A1* | 9/2006 | Huang | C07K 16/00 424/133.1 |
| 2007/0178552 A1 | 8/2007 | Arathoon et al. | |
| 2008/0241160 A1 | 10/2008 | Herrera et al. | |
| 2008/0274114 A1 | 11/2008 | Beidler et al. | |
| 2009/0182127 A1 | 7/2009 | Kjaergaard et al. | |
| 2009/0214523 A1 | 8/2009 | Fung et al. | |
| 2010/0098730 A1 | 4/2010 | Lowman et al. | |
| 2010/0105874 A1* | 4/2010 | Schuurman | C07K 16/00 530/387.3 |
| 2010/0255010 A1 | 10/2010 | Fuh et al. | |
| 2011/0123532 A1 | 5/2011 | Gurney et al. | |
| 2014/0294810 A1 | 10/2014 | Lowman et al. | |

FOREIGN PATENT DOCUMENTS

| | | |
|---|---|---|
| EP | 0 425 235 B1 | 5/1991 |
| EP | 1 391 213 A1 | 2/2004 |
| JP | H11-500915 A | 1/1999 |
| JP | 2001-523971 A | 11/2001 |
| JP | 2004-502428 A | 1/2004 |
| JP | 2006-515503 A | 6/2006 |
| JP | 2007-515493 A | 6/2007 |
| JP | 2008-511337 A | 4/2008 |
| JP | 2008-515780 A | 5/2008 |
| WO | WO-87/00195 A1 | 1/1987 |
| WO | WO-90/03430 A1 | 4/1990 |
| WO | WO-90/08187 A1 | 7/1990 |
| WO | WO-90/11294 A1 | 10/1990 |
| WO | WO-91/01133 A1 | 2/1991 |
| WO | 93/11161 A1 | 6/1993 |
| WO | WO-93/21232 A1 | 10/1993 |
| WO | WO-94/11026 A2 | 5/1994 |
| WO | WO-94/11026 A3 | 5/1994 |
| WO | WO-96/27011 A1 | 9/1996 |
| WO | 98/50431 | 11/1998 |
| WO | WO-98/50431 A2 | 11/1998 |
| WO | WO-98/50431 A3 | 11/1998 |
| WO | 00/29004 A1 | 5/2000 |
| WO | WO-00/24770 A2 | 5/2000 |
| WO | WO-00/24770 A3 | 5/2000 |
| WO | WO-02/02773 A2 | 1/2002 |
| WO | WO-02/02773 A3 | 1/2002 |
| WO | 02/051870 A2 | 7/2002 |
| WO | 02/051870 A3 | 7/2002 |
| WO | WO-02/088172 A2 | 11/2002 |
| WO | WO-02/088172 A3 | 11/2002 |
| WO | WO-02/092620 A2 | 11/2002 |
| WO | WO-02/092620 A3 | 11/2002 |
| WO | WO-03/031589 A2 | 4/2003 |
| WO | WO-03/031589 A8 | 4/2003 |
| WO | 03/035694 A2 | 5/2003 |
| WO | 03/035694 A3 | 5/2003 |
| WO | 03/057134 A2 | 7/2003 |
| WO | 03/057134 A3 | 7/2003 |
| WO | 2004/009618 A2 | 1/2004 |
| WO | WO-2004/026329 A1 | 4/2004 |
| WO | 2005/035572 A2 | 4/2005 |
| WO | 2005/035572 A3 | 4/2005 |
| WO | WO-2005/062916 A2 | 7/2005 |
| WO | WO-2005/062916 A3 | 7/2005 |
| WO | 2006/028936 A2 | 3/2006 |
| WO | 2006/028936 A3 | 3/2006 |
| WO | 2006/028956 A2 | 3/2006 |
| WO | WO-2006/085938 A2 | 8/2006 |
| WO | WO-2006/085938 A3 | 8/2006 |
| WO | 2007/147901 A1 | 12/2007 |
| WO | 2009/089004 A1 | 7/2009 |
| WO | WO-2010/045193 A1 | 4/2010 |
| WO | 2011/034605 A2 | 3/2011 |

OTHER PUBLICATIONS

Baldwin and Byers, "Monoclonal Antibodies in Cancer Treatment" *LANCET* 327(8481):603-605 (Mar. 15, 1986).

Barnes and Sato, "Methods for Growth of Cultured Cells in Serum-Free Medium" *Analytical Biochem.* 102:255-270 (1980).

Bass et al. et al., "Hormone Phage: An Enrichment Method for Variant Proteins with Altered Binding Properties" *Proteins* 8(4):309-314 (1990).

Bothmann and Pluckthun, "The Periplasmic *Escherichia coli* Peptidylprolyl cis,trans-Isomerase FkpA" *J Biol. Chem.* 275(22):17100-17105 (Jun. 2, 2000).

Carlsson et al. et al., "Protein Thiolation and Reversible Protein-Protein Conjugation" *Biochem J* 173:723-737 (1978).

Chari et al., "Immunoconjugates Containing Novel Maytansinoids: Promising Anticancer Drugs" *Cancer Res* 52:127-131 (1992).

Chen et al., "Chaperone activity of DsbC" *J Biol Chem* 274(28):19601-19605 (Jul. 9, 1999).

Chen, Y. et al., "Selection and Analysis of an Optimized anti-VEGF Antibody:Crystal Structure of an Affinity-Matured Fab in Complex With Antigen" *J Mol Biol* 293:865-881 (1999).

Chothia et al."The Nature of the Accessible and Buried Surfaces in Proteins" *J. Mol. Biol.* 105:1-12 (revised form Mar. 15, 1976).

Clynes, et al., "Fc Receptors are Required in Passive and Active Immunity to Melanoma" *Proc. Natl. Acad. Sci.* 95:652-656 (Jan. 1998).

(56) References Cited

OTHER PUBLICATIONS

Doronina et al., "Development of potent monoclonal antibody auristatin conjugates for cancer therapy" *Nat Biotechnol* 21(7):778-784 (Jul. 2003).
Ellman et al., "Biosynthetic method for introducing unnatural amino acids site-specifically into proteins" *Meth Enzym* 202:301-336 (1991).
Fraker and Speck, "Protein and cell membrane iodinations with a sparingly chloroamide, 1,3,4,6-tetrachloro-3a,6a-diphrenylglycoluril," *Biochem Bioph Res Co* 80(40):849-857 (1978).
Gazzano-Santoro et al., "A Non-Radiactive Complement-Dependent Cytotoxicity Assay for Anti-CD20 Monoclonal Antibody" *J Immunol Methods* 202:163-171 (1997).
Geoghegan et al. "Site-Directed Conjugation of Nonpeptide Groups to Peptides and Proteins via Periodate Oxidation of a 2-Amino Alcohol. Application to Modification at N-Terminal Serine," *Bioconjugate Chem* 3:138-146 (1992).
Graham et al., "Characteristics of a Human Cell Line Transformed by DNA from Human Adenovirus Type 5" *J. Virol.* 36:59-72 (1977).
Guss et al. "Structure of the IgG-Binding Regions of Streptococcal Protein G," *The EMBO Journal* 5(7):1567-1575 (1986).
Ham et al., "Media and growth requirements" *Method Enzymol* 58:44-93 (1979).
Hara et al., "Overproduction of Penicillin-Binding Protein 7 Suppresses Thermosensitive Growth Defect at Low Osmolarity Due to an spr Mutation of *Escherichia coli*" *Microb. Drug Resist.* 2(1):63-72 (Spring 1996).
Janeway, C., "Immunotherapy by Peptides?" *Nature* 341:482-483 (Oct. 12, 1989).
Joly et al., "Overexpression of *Escherichia coli* Oxidoreductases Increases Recombinant Insulin-Like Growth Factor-I Accumulation" *Proc. Natl. Acad. Sci. USA* 95:2773-2777 (Mar. 1998).
Kabat et al. *Sequences of Proteins of Immunological Interest*, fifth Edition, U.S. Department of Health and Human Services, Bethesda, MD, NIH Publication No. 90-3242, pp. 688-696, (1991).
Kindt et al., *Kuby Immunology*, Antigens and Antibodies, Chapter 4, 6th ed. Edition, N.Y. W.H. Freeman and Co. p. 91 (2007).
Liu et al., "Eradication of Large Colon Tumor Xenografts by Targeted Delivery of Maytansinoids" *Proc Natl Acad Sci U S A*. 93(16):8618-8623 (Aug. 6, 1996).
Mandler et al. Modifications in Synthesis Strategy Improve the Yield and Efficacy of Geldanamycin-Herceptin Immunoconjudgates *Bioconjugate Chem* 13:786-791 (2002).
Mandler et al., "Immunoconjugates of Geldanamycin and Anti-HER2 Monoclonal antibodies: antiproliferative activity on human breast carcinoma cell lines" *J National Cancer Institute* 92(19):1573-1581 (Oct. 4, 2000).
Mandler et al., "Synthesis and Evaluation of Antiproliferative Activity of a Geldanamycin-Herceptin(tm) Immunoconjugate" *Bioorg Med Chem Lett* 10:1025-1028 (2000).
Mather, "Establishment and Characterization of Two Distinct Mouse Testicular Epithelial Cell Lines" *Biol. Reprod.* 23:243-252 (1980).
Mather et al., "Culture of Testicular Cells in Hormone-Supplemented Serum-Free Medium" *Ann NY Acad Sci* 383:44-68 (1982).
Murakami, et al., "Cell Cycle Regulation, Oncogenes, and Antieioplastic Drugs" *The Molecular Basis of Cancer*, Philadelphia:W.B. Saunders, Chapter 1, pp. 3-17 (1995).
Nicolaou et al., "Calicheamicin θ: A Rationally Designed Molecule With Extremely Potent and Selective DNA Cleaving Properties and Apoptosis Inducing Activity." *Agnew Chem Intl Ed Engl* 33(2):183-186 (1994).
Niculescu-Duvaz and Springer, "Antibody-Directed Enzyme Prodrug Therapy (ADEPT): A Review" *Adv. Drug Deliv. Rev.* 26:151-172 (1997).
Noren et al., "A General Method for Site-Specific Incorporation of Unnatural Amino Acids Into Proteins" *Science* 244(4901):182-188 (Apr. 14, 1989).

Offner et al., "T Cell Receptor Peptide Therapy Triggers Autoregulation of Experimental Encephalomyelitis" *Science* 251:430-432 (1991).
Pettit et al., "Marine Animal Biosynthetic Constituents for Cancer Chemotherapy" *J. Nat. Prod.* 44(4):482-485 (Jul. 1981).
Pettit. *Progress in the Chemistry of Organic Natural Products*, W. Hertz et al., SpringerWienm NewYork, vol. 70:1-79 (1997).
Pettit et al., "Antineoplastic Agents 360. Synthesis and Cancer Cell Growth Inhibitory Studies of Dolastatin 15 Structural Modifications" *Anticancer Drug Des.* 13(1):47-66 (Jan. 1998).
Pettit et al., "Specific Activities of Dolastatin 10 and Peptide Derivatives Against Cryptococcus Neoformans" *Antimicrob Agents and Chemotherapy* 42(11):2961-2965 (Nov. 1998).
Pinheiro et al., Linear and Nonlinear Mixed effects Models, (2008). R-Package version 3:1-89.
Pluckthun, A. *The Pharmacology of Monoclonal Antibodies: Handbook of Pharmacology* "Antibodies from *Escherichia coli*" (Chapter 11), Rosenberg and Moore, eds., Berlin:Springer-Verlag, vol. 113:269-315 (1994).
Poncet, "The Dolastatins, a Family of Promising Antineoplastic Agents" *Curr. Pharm. Des.* 5(3):136-162 (Mar. 1999).
Ponder and Richards, "Tertiary Templates for Proteins. Use of Packing Criteria in the Enumeration of Allowed Sequences for Different Structural Classes" *J Mol Biol.* 193(4):775-791 (Feb. 20, 1987).
Proba et al. et al., "Functional Antibody Single-Chain Fragments From the Cytoplasm of *Escherichia coli*: Influence of Thioredoxin Reductase (TrxB)" *Gene* 159:203-207 (1995).
Ramm and Pluckthun, "The Periplasmic *Escherichia coli* Peptidylprolyl cis,trans-Isomerase FkpA" *J. Biol. Chem.* 275(22):17106-17113 (Jun. 2, 2000).
Reyes et al., "Expression of Human β-Interferon cDNA Under the Control of a Thymidine Kinase Promoter From Herpes Simplex Virus" *Nature* 297:598-601 (Jun. 17, 1982).
Rowland et al., "Drug Localisation and Growth Inhibition Studies of Vindesine-Monoclonal Anti-CEA Conjugates in a Human Tumour Xenograft" *Cancer Immunol Immunother* 21:183-187 (1986).
Schroder and K. Lubke "The Peptides"Academic Press, vol. 1:76-136 (1965).
Siebenlist et al., "*E. coli* RNA Polymerase Interacts Homologously with two Different Promoters" *Cell* 20(2):269-281 (Jun. 1980).
Simmons et al., "Expression of Full-Length Immunoglobulins in *Escherichia coli* : Rapid and Efficient Production of Aglycosylated Antibodies" *J Immunol. Methods* 263:133-147 (2002).
Stella et al. "Prodrugs: A Chemical Approach to Targeted Drug Delivery," *Directed Drug Delivery*, Humana Press, New Jersey, pp. 247-267 (1985).
Syriogos et al., "Antibody Directed Enzyme Prodrug Therapy (ADEPT): A Review of the Experimental and Clinical Considerations" *Anticancer Reserach* 19(1A):605-613 (Jan. 1999).
Thorpe, "Antibody Carriers of Cytotoxic Agents in Cancer Therapy: a Review" Antibodies '84: Biological and Clinical Applications (A Pinchera, G. Doria, F. Dammacco and A. Bargellesi, eds. pp. 475-506 (1985)).
Urlaub et al., "Isolation of Chinese Hamster Cell Mutants Deficient in Dihydrofolate Reductase Activity" *P Natl Acad Sci USA* 77(7):4216-4220 (Jul. 1980).
Vitetta et al., "Redesign Nature's Poisions to Create Anti-Tumor Reagents" *Science* 238:1098-1104 (Nov. 20, 1987).
Wilman D.E.V.., Production in Cancer Chemotherapy Biochemical Society Transitions, 615th Meeting, Belfast, Ireland, pp. 375-382 (1986).
Woyke et al., "In vitro activities and postantifungal effects of the potent dolastatin 10 derivative auristatin PHE" *Antimicrob Agents Chemother* 45(12):3580-3584 (Dec. 2001).
Yaniv, "Enhancing Elements for Activation of Eukaryotic Promoters" *Nature* 297:17-18 (May 6, 1982).
Zamyatnin, "Protein Volumes in Solution" *Prog.Biophys Mol. Biol.* 24:107-123 (1972).
Arie et al., "Chaperone function of FkpA, a heat shock prolyl isomerase, in the periplasm of *Escherichia coli*" Mol Microbiol 39(1):199-210 (2001).

(56) References Cited

OTHER PUBLICATIONS

Berg et al., "Bispecific antibodies that mediate killing of cells infected with human immunodeficiency virus of any strain" P Natl Acad Sci USA 88:4723-4727 (Jun. 1991).
Bloom et al., "Intrachain disulfide bond in the core hinge region of human IgG4" Protein Sci 6:407-415 ( 1997).
Bostrom et al., "Variants of the antibody herceptin that interact with HER2 and VEGF at the anitgen binding site" Science 323:1610-1614 (Mar. 2009).
Burton, D., "Immunoglobulin G: Functional sites" Mol Immunol 22(3):161-206 ( 1985).
Capel et al., "Heterogeneity of human IgG Fc receptors" Immunomethods 4:25-34 ( 1994).
Chamow et al., "A humanized, bispecific immunoadhesin-antibody that retargets CD3+ effectors to kill HIV-1-infected cells" J Hematotherapy 4:439-446 ( 1995).
Clackson et al., "Making antibody fragments using phage display libraries" Nature 352(6336):624-628 (Aug. 15, 1991).
Daeron, "Fc receptor biology" Annu Rev Immunol 15:203-234 ( 1997).
Davies and Riechmann, "'Camelising' human antibody fragments: NMR studies on VH domains" FEBS Lett 339:285-290 ( 1994).
De Haas et al., "Fcγ receptors of phagocytes" J Lab Clin Med 126:330-341 (Oct. 1995).
Dooley and Flajnik, "Antibody repertoire development in cartilaginous fish" Developmental and Comparative Immunol 30:43-56 ( 2006).
Fischer and Leger, "Bispecific antibodies: Molecules that enable novel therapeutic strategies" Pathobiology 74:3-14 ( 2007).
Gronwall et al., "Generation of Affibody® ligands binding interleukin-2 receptor α/CD25" Biotechnol Appl Biochem 50:97-112 ( 2008).
Guss et al., "Structure of the IgG-binding regions of streptococcal protein G" EMBO J 5(7):1567-1575 ( 1986).
Guyer et al., "Immunoglobulin binding by mouse intestinal epithelial cell receptors" J Immunol 117(2):587-593 (Aug. 1976).
Hirota et al., "On the process of cellular division in *Escherichia coli*: A mutant of *E. coli* lacking a murein-lipoprotein" P Natl Acad Sci USA 74(4):1417-1420 (Apr. 1977).
Holliger et al., "'Diabodies': Small bivalent and bispecific antibody fragments" P Natl Acad Sci USA 90:6444-6448 (Jul. 1993).
Holt et al., "Domain antibodies: proteins for therapy" Trends Biotechnol 21(11):484-490 (Nov. 2003).
Humphreys et al., "F(ab') $_2$ molecules made from *Escherichia coli* produced Fab' with hinge sequences conferring increased serum survival in an animal model" J Immunol Methods 217:1-10 ( 1998).
Humphreys et al., "Formation of dimeric Fabs in *Escherichia coli*: effect of hinge size and isotype, presence of interchain disulfide bond, Fab' expression levels, tail piece sequences and growth conditions" J Immunol Methods 209(2):193-202 (Dec. 1, 1997).
Jin et al., "MetMab, the One-armed 5D5 anti-c-Met antibody, inhibits orthotopic pancreatic tumor growth and improves survival" Cancer Res 68(11):4360 (Jun. 2008).
Jones et al., "Replacing the complementarity-determining regions in a human antibody with those from a mouse" Nature 321:522-525 (May 29, 1986).
Kikuchi et al., "The nucleotide sequence of the promoter and the amino-terminal region of alkaline phosphatase structural gene (phoA) of *Escherichia coli*" Nucleic Acids Res 9(21):5671-5678 ( 1981).
Kim et al., "Localization of the site of the murine IgG1 molecule that is involved in binding to the murine intestinal Fc receptor" Eur J Immunol 24:2429-2434 ( 1994).
Kontermann, R., "Recombinant bispecific antibodies for cancer therapy" Acta Pharmacologica Sinica 26(1):1-9 (Jan. 2005).
Lee and Kwak, "Expression and functional reconstitution of a recombinant antibody (Fab') specific for human apolipoprotein B-100" J Biotechnol 101:189-198 ( 2003).
Lee et al., "Characterization of the gene encoding heat-stable toxin II and preliminary molecular epidemiological studies of enterotoxigenic *Escherichia coli* heat-stable toxins II producers" Infect Immun 42:264-268 (Oct. 1983).
Lindmark et al., "Binding of immunoglobulins to protein A and immunoglobulin levels in mammalian sera" J Immunol Methods 62:1-13 ( 1983).
Malmborg and Borrebaeck, "BIAcore as a tool in antibody engineering" J Immunol Methods 183:7-13 ( 1995).
Martens et al., "A novel one-armed anti-c met antibody inhibits glioblastoma growth in vivo" Clin Cancer Res 12(20):6144-6152 (Oct. 2006).
Marvin and Zhu, "Recombinant approaches to IgG-like bispecific antibodies" Acta Pharmacologica Sinica 26(6):649-658 (Jun. 2005).
Morrison, S. et al., "Chimeric human antibody molecules: Mouse antigen-binding human constant region domains" P Natl Acad Sci USA 81:6851-6855 ( 1984).
Muyldermans et al., "Recognition of antigens by single-domain antibody fragments: the superfluous luxury of paired domains" Trends Biochem Sci 26(4):230-235 (Apr. 2001).
Nilsson et al., "A synthetic IgG-binding domain based on staphylococcal protein A" Protein Eng 1:107-113 ( 1987).
Nord et al., "A combinational library of an alpha-helical bacterial receptor domain" Protein Eng 8(6):601-608 ( 1995).
Nord et al., "Binding proteins selected from combinatorial libraries of an α-helical bacterial receptor domain" Nature Biotechnol 15:772-777 (Aug. 1997).
Pack et al., "Improved bivalent miniantibodies, with identical avidity as whole antibodies, produced by high cell density fermentation of *Escherichia coli*" Bio/Technology 11:1271-1277 (Nov. 1993).
Pack et al., "Miniantibodies: Use of amphipathic helices to produce functional, flexibly linked dimeric F $_v$ fragments with high avidity in *Escherichia coli*" Biochemistry 31(6):1579-1584 ( 1992).
Papadea and Check, "Human immunoglobulin G and immunoglobulin G subclasses: Biochemical, genetic, and clinical aspects" Critical Reviews in Clinical Laboratory Sciences 27(1):27-58 ( 1989).
Picken et al., "Nucleotide sequence of the gene for heat-stable enterotoxin II of *Escherichia coli*" Infect Immun 42(1):269-275 (Oct. 1983).
Portolano et al., "Lack of promiscuity in autoantigen-specific H and L chain combinations as revealed by human H and L chain 'Roulette'" J Immunol 150(3):880-887 (Feb. 1993).
Presta, L., "Antibody engineering" Curr Opin Struc Biol 2:593-596 ( 1992).
Ravetch and Kinet, "Fc receptors" Annu Rev Immunol 9:457-492 ( 1991).
Ridgway et al., "Identification of a human anti-CD55 single-chain Fv by subtractive panning of a phage library using tumor and nontumor cell lines" Cancer Res 59(11):2718-2723 (Jun. 1, 1999).
Riechmann et al., "Reshaping human antibodies for aherapy" Nature 332:323-327 (Mar. 1988).
Scheer, J., Abstract 2010 Empowered Antibody Therapies Conference, Burlingame, CA.
Simmons and Yansura, "Translational level is a critical factor for the secretion of heterologous proteins in *Escherichia coli*" Nat Biotechnol 14:629-634 (May 1996).
Ward et al., "Binding activities of a repertoire of single immunoglobulin variable domains secreted from *Escherichia coli*" Nature 341:544-546 (Oct. 12, 1989).
Wibbenmeyer et al., "Cloning, expression, and characterization of the Fab fragment of the anti-lysozyme antibody HyHEL-5" Biochimica et Biophysica Acta 1430:191-202 (1999).
Wong et al., "DNA internalized via caveolae requires microtubule-dependent, Rab7-independent transport to the late endocytic pathway for delivery to the nucleus" J Biol Chem 282(31):22953-22963 (Aug. 2007).
Ye et al., "High-level protein expression in scalable CHO transient transfection" Biotechnol Bioeng 103:542-551 ( 2009).
Zapata et al., "Engineering linear F(ab') $_2$ fragments for efficient production in *Escherichia coli* and enhanced antiproliferative activity" Protein Eng 8(10):1057-1062 ( 1995).
Zhu et al., "Remodeling domain interfaces to enhance heterodimer formation" Protein Sci 6(4):781-788 (Apr. 1997).

(56) References Cited

OTHER PUBLICATIONS

Zhu et al., "Tumor localization and therapeutic potential of an antitumor-anti-CD3 heteroconjugate antibody in human renal cell carcinoma xenograft models" Cancer Letters 86:127-134 (1994).
Pan et al. "Blocking neuropilin-1 function has an additive effect with anti-VEGF to inhibit tumor growth," *Cancer Cell* 11(1):53-57, (Jan. 2007).

\* cited by examiner

Lane 1) Pool of Elution 36.6-37.6 Minutes for Co-culture with -lpp Mutation
Lane 2) Pool of Elution 36.6-37.6 Minutes for Co-culture with -lpp Mutation and EDTA
Lane 3) Pool of Elution 36.6-37.6 Minutes for Co-culture with -lpp Mutation and EDTA and Mg2+

Lane 1) Pool of Elution 36.6-37.6 Minutes for IL-4/IL-13 Co-culture with -lpp Mutation Lane 3) Pool of Elution 36.6-37.6 Minutes for IL-4/IL-13 Co-culture with -lpp Mutation and EDTA and $Mg^{2+}$ 1: Knob
2: Hole
3: Mark 12 MW Markers
4. Knob + 20mM DTT
5. Hole + 20mM DTT

Gel of HIC Purified Material

1: Final Material
2: Mark12
3. Final Material + 20mM DTT

| | Theorectical Mass (Da) | Measured Mass (Da) |
|---|---|---|
| Knob/Knob | 148,819.02 | N/A |
| Hole/Hole | 146,910.40 | N/A |
| Knob/Hole | 147,864.71 | 147,870.38 |

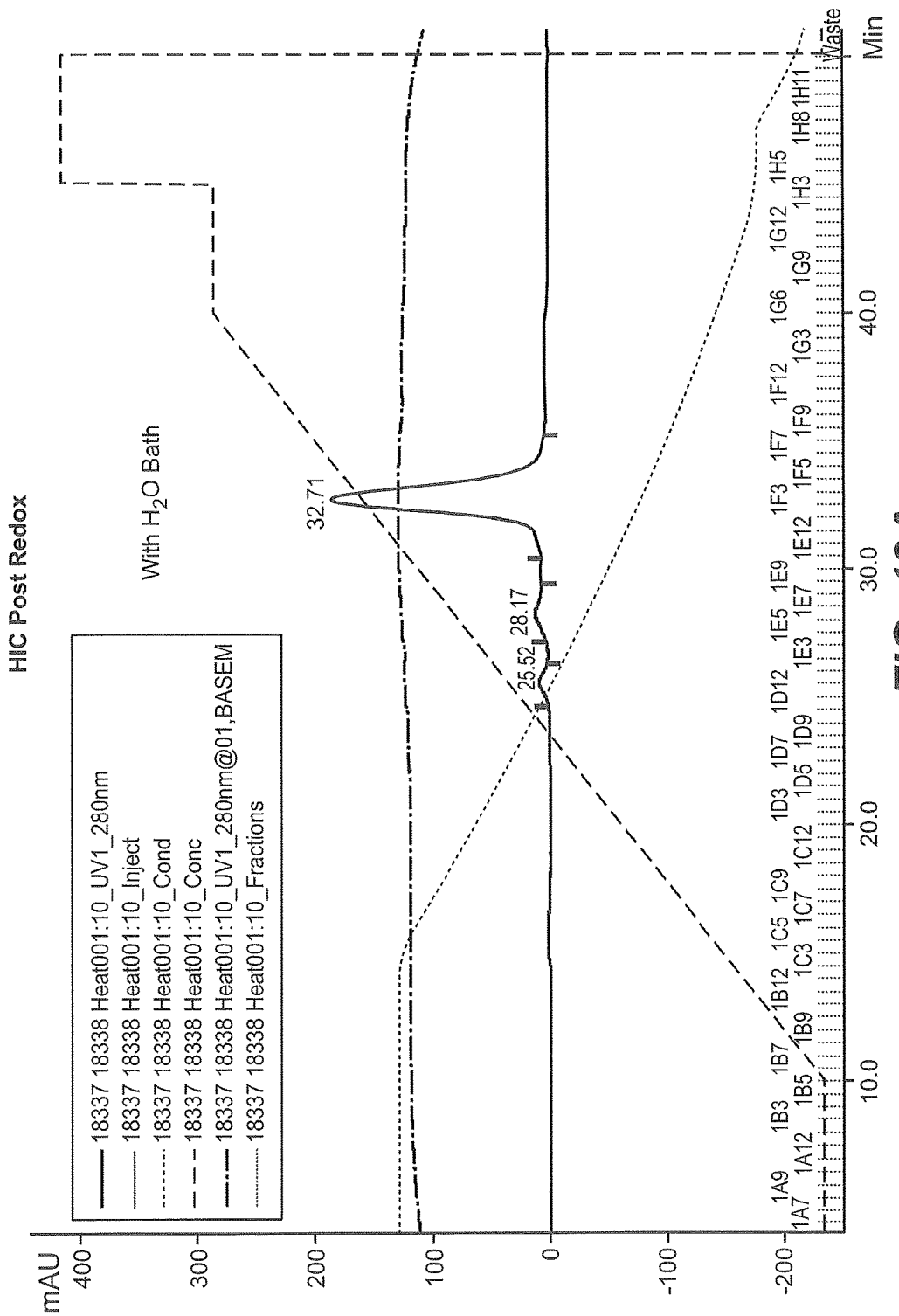

PRODUCTION OF HETEROMULTIMERIC PROTEINS

CROSS-REFERENCE TO RELATED APPLICATIONS

The present application claims priority to U.S. Provisional Patent Application Ser. No. 61/327,302, entitled "Production of Heteromultimeric Proteins," filed 23 Apr. 2010, the entire contents of which are incorporated herein by reference.

TECHNICAL FIELD

This invention relates to methods for the production of heteromultimeric proteins.

BACKGROUND

Monoclonal antibodies of the IgG type contain two identical antigen-binding arms and a constant domain (Fc). Antibodies with a differing specificity in their binding arms usually do not occur in nature and, therefore, have to be crafted with the help of chemical engineering (e.g., chemical cross-linking, etc), recombinant DNA and/or cell-fusion technology.

Bispecific antibodies can bind simultaneously two different antigens. This property enables the development of therapeutic strategies that are not possible with conventional monoclonal antibodies. The large panel of imaginative bispecific antibody formats that has been developed reflects the strong interest for these molecules. See Berg J, Lotscher E, Steimer K S, et al., "Bispecific antibodies that mediate killing of cells infected with human immunodeficiency virus of any strain," Proc Natl Acad Sci USA (1991) 88(11): 4723-4727 and Fischer N and Leger O., "Biospecific Antibodies: Molecules That Enable Novel Therapeutic Strategies," Pathobiology (2007) 74:3-14.

Another class of multispecific molecules is recombinant fusion proteins. Recombinant fusion proteins consisting of the extracellular domain of immunoregulatory proteins and the constant (Fc) domain of immunoglobulin (Ig) represent a growing class of human therapeutics. Immunoadhesins combine the binding region of a protein sequence, with a desired specificity, with the effector domain of an antibody. Immunoadhesins have two important properties that are significant to their potential as therapeutic agents: the target specificity, and the pharmacokinetic stability (half-life in vivo that is comparable to that of antibodies). Immunoadhesins can be used as antagonist to inhibit or block deleterious interactions or as agonist to mimic or enhance physiological responses. See Chamow S M, Zhang D Z, Tan X Y, et al., "A humanized, bispecific immunoadhesin-antibody that retargets CD3+ effectors to kill HIV-1-infected cells," J Hematother 1995; 4(5): 439-446.

Other multispecific molecules have been discussed elsewhere. Examples include but are not limited to: Fisher et al., Pathobiology (2007) 74:3-14 (review of various bispecific formats); U.S. Pat. No. 6,660,843, issued Dec. 9, 2003 to Feige et (peptibodies); US Pat. Publ. No. 2002-004587 published Jan. 10, 2002 (multispecific antibodies); U.S. Pat. No. 7,612,181 issued Nov. 3, 2009 to Wu et al. (Dual Variable Domain format); U.S. Pat. No. 6,534,628, Nord K et al., Prot Eng (1995) 8:601-608, Nord K et al., Nat Biotech (1997) 15:772-777, and Grönwall et al., Biotechnol Appl Biochem. (2008) June; 50(Pt 2): 97-112 (Affibodies); Martens et al., Clin Cancer Res (2006), 12: 6144-6152 and Jin et al., Cancer Res (2008) 68(11):4360-4368 (one armed antibodies); Bostrom et al., Science (2009) 323:1610-1614 (Dual Action Fab, aka mixed valency antibodies). Other formats are known to those skilled in the art.

The manufacturing of clinical grade material remains challenging for the multispecific molecules described above. As noted above, there are many paths to the production of molecules with mixed binding arms, i.e., binding arms that are not identical to each other. Each of these methods has its drawbacks.

Chemical cross-linking is labor intensive as the relevant species may yet need to be purified from homodimers and other undesired by-products. In addition, the chemical modification steps can alter the integrity of the proteins thus leading to poor stability. Thus, this method is often inefficient and can lead to loss of antibody activity.

Cell-fusion technology (e.g., hybrid hybridomas) express two heavy and two light chains that assemble randomly leading to the generation of 10 antibody combinations. The desired heteromultimeric antibodies are only a small fraction of the antibodies thus produced. Purification of the desired heteromultimeric proteins dramatically reduces production yields and increases manufacturing costs.

Recombinant DNA techniques have been used to generate various heteromultimeric formats, e.g., single chain Fv, diabodies, etc., that do not comprise an Fc domain. A major drawback for this type of antibody molecule is the lack of the Fc domain and thus the ability of the antibody to trigger an effector function (e.g., complement activation, Fc-receptor binding etc.). Thus, a bispecific antibody comprising a functional Fc domain is desired.

Recombinant DNA techniques have also been used to generate 'knob into hole' bispecific antibodies. See US Patent Application 20030078385 (Arathoon et al.—Genentech). One constraint of this strategy is that the light chains of the two parent antibodies have to be identical to prevent mispairing and formation of undesired and/or inactive molecules due to being expressed in the same cell.

Thus, there remains a need for alternative methods of producing heteromultimeric proteins. The invention described herein provides such methods. These and other aspects and advantages of the invention will be apparent from the description of the invention provided herein.

BRIEF SUMMARY OF THE INVENTION

Production of heteromultimeric proteins, e.g., multispecific antibodies, using current techniques has drawbacks including the production of a mixture of products, reduced yield and decreased/elimination of effector function among others. Thus, it is desirable to produce heteromultimeric proteins efficiently and at high levels.

The production of antibody molecules, by various means, is generally well understood. U.S. Pat. No. 6,331,415 (Cabilly et al.), for example, describes a method for the recombinant production of immunoglobulin where the heavy and light chains are expressed simultaneously from a single vector or from two separate vectors in a single cell. Wibbenmeyer et al., (1999, Biochim Biophys Acta 1430(2): 191-202) and Lee and Kwak (2003, J. Biotechnology 101: 189-198) describe the production of monoclonal antibodies from separately produced heavy and light chains, using plasmids expressed in separate cultures of E. coli. Various other techniques relevant to the production of antibodies are described in, e.g., Harlow, et al., ANTIBODIES: A LABORATORY MANUAL, Cold Spring Harbor Laboratory Press, Cold Spring Harbor, N.Y., (1988) and WO2006028936. Yet each of these have draw backs such as low yield, use of chemicals The inventive methods provide for the expression of each component, e.g., one arm of an antibody, of a hinge-containing heteromultimeric protein in a separate host cell and the assembly of the hinge-containing heteromultimeric protein, e.g., a multispecific antibody, without the addition of a reductant.

This invention provides an easy and efficient production process/method that allows for the economical production of heteromultimeric proteins, e.g., multispecific antibodies.

The invention provides efficient and novel methods of producing multispecific immunoglobulin complexes (e.g., multispecific antibodies) and other multimeric proteins (collectively referred to herein as heteromultimeric proteins) that overcome limitations of traditional methods. Heteromultimeric proteins, such as bispecific antibodies, can be provided as a highly homogeneous heteromultimer polypeptide according to methods of the invention. In addition, the methods provided for herein do not rely on the addition of a reductant to achieve the formation of at least one, at least two, at least three, at least four interchain disulfide bonds in the heteromultimeric protein.

In a first aspect, the method described herein allows for the preparation of a heteromultimeric protein comprising a first hinge-containing polypeptide having a first heterodimerization domain and a second hinge-containing polypeptide having a second heterodimerization domain, wherein the second heterodimerization domain interacts with the first heterodimerization domain, and wherein the first and second hinge-containing polypeptides are linked by at least one interchain disulfide bond, the method comprising the steps of:
  (a) culturing a first host cell comprising a first nucleic acid encoding the first hinge-containing polypeptide under conditions where the hinge-containing polypeptide is expressed;
  (b) culturing a second host cell comprising a nucleic acid encoding the second hinge-containing polypeptide under conditions where the hinge-containing polypeptide is expressed;
  (c) disrupting the cell membranes so that the first and second hinge-containing polypeptides are released into the extracellular milieu, wherein the first and second host cells have been combined together in a single suspension; and
  (d) recovering the heteromultimeric protein,
wherein said method does not require the addition of a reductant.

In a second aspect, the method of preparing a heteromultimeric protein comprising heteromultimeric protein comprising a first hinge-containing polypeptide having a first heterodimerization domain and a second hinge-containing polypeptide having a second heterodimerization domain, wherein the second heterodimerization domain interacts with the first heterodimerization domain, and wherein the first and second hinge-containing polypeptides are linked by at least one interchain disulfide bond, the method comprising the steps of:
  (a) providing a purified first hinge-containing polypeptide having a first heterodimerization domain;
  (b) providing a purified second hinge-containing polypeptide having a second heterodimerization domain;
  (c) combining the first and second hinge-containing polypeptides;
  (d) refolding the first hinge-containing polypeptide with the second hinge-containing polypeptide; and
  (e) recovering the heteromultimeric protein complex.

In a third aspect, the methods provided for herein are directed to a method of preparing a heteromultimeric protein comprising incubating a first pair of immunoglobulin heavy and light chain polypeptides, and a second pair of immunoglobulin heavy and light chain polypeptides, under conditions permitting multimerization of the first and second pair of polypeptides to form a substantially homogeneous population of antibodies, wherein the conditions do not comprise the addition of a reductant; wherein the first pair of polypeptides is capable of binding a first target; wherein the second pair of polypeptides is capable of binding a second target molecule; and wherein Fc polypeptide of the first heavy chain polypeptide and Fc polypeptide of the second heavy chain polypeptide meet at an interface, and the interface of the second Fc polypeptide comprises a protuberance which is positionable in a cavity in the interface of the first Fc polypeptide.

In a fourth aspect, there is a method of generating a combinatorial library of heteromultimeric proteins, said method comprising a first hinge-containing polypeptide having a first heterodimerization domain and a second hinge-containing polypeptide having a second heterodimerization domain, wherein the second heterodimerization domain interacts with the first heterodimerization domain, and wherein the first and second hinge-containing polypeptides are linked by at least one interchain disulfide bond, the method comprising the steps of:
  (a) culturing a first host cell and at least two additional host cells, wherein
    a. said first host cell comprises a first nucleic acid encoding a first heterodimerization domain-containing polypeptide; and
    b. said additional host cells comprise a nucleic acid comprising a second heterodimerization domain-containing polypeptide,
  (b) combining the first and at least two additional host cells;
  (c) treating the cells so that the first and second heterodimerization domain-containing polypeptides are released into the extracellular milieu; and
  (d) recovering the heteromultimeric proteins,
wherein said method does not require the addition of a reductant.

In a fifth aspect, there are provided the heteromultimeric proteins produced by the methods described herein.

It is to be understood that methods of the invention can include other steps which generally are routine steps evident for initiating and/or completing the process encompassed by methods of the invention as described herein. For example, in one embodiment, step (a) of a method of the invention is preceded by a step wherein a nucleic acid encoding a first hinge-containing polypeptide is introduced into a first host cell, and a nucleic acid encoding a second hinge-containing polypeptide is introduced into a second host cell. In one embodiment, methods of the invention further comprise a step of purifying heteromultirneric proteins having binding specificity to at least two distinct targets. In one embodiment, no more than about 10%, 15%, or 20% of isolated polypeptides are present as monomers or heavy-light chain dimers prior to the step of purifying the heteromultimeric proteins.

In an embodiment, the first and/or second hinge-containing polypeptide is an antibody heavy chain. In a further embodiment, the antibody heavy chain is paired with an antibody light chain to provide a heavy-light chain pair. In some embodiments, the heavy-light chain pair are covalently linked. In another embodiment, the heavy-light chain pair defines a target binding arm. In some embodiments, the target binding arms are identical. In some embodiments, the target binding arms each recognize two distinct targets.

In some embodiments, the first and/or second hinge-containing polypeptide comprises an Fc region. In another embodiment the first and/or second hinge-containing polypeptide comprises at least one constant heavy domain. In another embodiment, the first and/or second hinge-containing polypeptide comprises a variable heavy chain domain. In another embodiment, the first and/or second hinge-containing polypeptide comprises a receptor binding domain. In some embodiments, the first and/or second hinge-containing polypeptide are substantially identical (i.e., the heterodimerization domain may not be identical with the regions outside of the heterodimerization domain being identical). In some embodiments, the first and/or second hinge-containing polypeptide are not identical.

In some embodiments, the heteromultimeric protein is selected from the group consisting of an antibody, a bispecific antibody, a multispecific antibody, one-armed antibody, monospecific monovalent antibody, a multispecific monovalent antibody, a bispecific maxibody, a monobody, an immunoadhesin, a peptibody, a bispecific peptibody, a monovalent peptibody, an affibody and a receptor fusion protein.

In some embodiments, said heteromultimeric proteins comprise a hinge region that has at least one, at least two, at least three, at least four, or any integer number up to all, of the cysteine residues that are normally capable of forming an inter-heavy chain disulfide linkage. In some embodiments, additional cysteines have been introduced into the hinge region.

A heteromultimeric protein of the invention may also be an antibody fragment, such as, for example, an Fc or Fc fusion polypeptide, so long as it comprises the hinge region of an immunoglobulin. An Fc fusion polypeptide generally comprises an Fc polypeptide (or fragment thereof) fused to a heterologous polypeptide sequence (such as an antigen binding domain), such as a receptor extracellular domain (ECD) fused to an immunoglobulin Fc polypeptide (e.g., Flt receptor ECD fused to a IgG2 Fc). For example, in one embodiment, an Fc fusion polypeptide comprises a VEGF binding domain, which may be a VEGF receptor, which includes flt, flk, etc. A heteromultimeric protein of the invention generally comprises a heavy chain constant domain and a light chain constant domain. In one embodiment, a heteromultimeric protein of the invention comprises a modification (for example, but not limited to, insertion of one or more amino acids, e.g., to form a dimerization sequence such as leucine zipper) for formation of inter-heavy chain dimerization or multimerization. In some embodiments, a portion (but not all) of the Fc polypeptide is missing in a heteromultimer of the invention, so long as it retains the hinge region of an immunoglobulin. In some of these embodiments, the missing sequence of the Fc polypeptide is a portion or all of the $C_H2$ and/or $C_H3$ domain. In some of these embodiments, the heteromultimeric protein comprises a dimerization domain (such as a leucine zipper sequence), for example fused to the C-terminus of the heavy chain fragment. In some of these embodiments, the heteromultimeric protein comprises a dimerization domain comprising mutations to provide for a "knob into hole" dimerization domain (as further defined below).

In some embodiments of the methods and heteromultimeric proteins of the invention, the hinge-containing polypeptides comprise at least one characteristic that promotes heterodimerization, while minimizing homodimerization, of the first and second hinge-containing polypeptides (e.g., between Fc polypeptides of the heavy chains). Such characteristic(s) improves yield and/or purity and/or homogeneity of the heteromultimeric protein populations obtainable by methods of the invention as described herein. In one embodiment, the Fc polypeptides of a first hinge-containing polypeptide and a second hinge-containing polypeptide meet/interact at an interface. In some embodiments wherein the Fc polypeptides of the first and second hinge-containing polypeptides meet at an interface, the interface of the second Fc polypeptide comprises a protuberance which is positionable in a cavity in the interface of the first Fc polypeptide. In one embodiment, the first Fc polypeptide has been altered from a template/original polypeptide to encode the cavity or the second Fc polypeptide has been altered from a template/original polypeptide to encode the protuberance, or both. In one embodiment, the first Fc polypeptide has been altered from a template/original polypeptide to encode the cavity and the second Fc polypeptide has been altered from a template/original polypeptide to encode the protuberance, or both. In one embodiment, the interface of the second Fc polypeptide comprises a protuberance which is positionable in a cavity in the interface of the first Fc polypeptide, wherein the cavity or protuberance, or both, have been introduced into the interface of the first and second Fc polypeptides, respectively. In some embodiments wherein the first and second Fc polypeptides meet at an interface, the interface of the first Fc polypeptide comprises a protuberance which is positionable in a cavity in the interface of the second Fc polypeptide. In one embodiment, the second Fc polypeptide has been altered from a template/original polypeptide to encode the cavity or the first Fc polypeptide has been altered from a template/original polypeptide to encode the protuberance, or both. In one embodiment, the second Fc polypeptide has been altered from a template/original polypeptide to encode the cavity and the first Fc polypeptide has been altered from a template/original polypeptide to encode the protuberance, or both. In one embodiment, the interface of the first Fc polypeptide comprises a protuberance which is positionable in a cavity in the interface of the second Fc polypeptide, wherein the protuberance or cavity, or both, have been introduced into the interface of the first and second Fc polypeptides, respectively.

In one embodiment, the protuberance and cavity each comprises a naturally occurring amino acid residue. In one embodiment, the Fc polypeptide comprising the protuberance is generated by replacing an original residue from the interface of a template/original polypeptide with an import residue having a larger side chain volume than the original residue. In one embodiment, the Fc polypeptide comprising the protuberance is generated by a method comprising a step wherein nucleic acid encoding an original residue from the interface of said polypeptide is replaced with nucleic acid encoding an import residue having a larger side chain volume than the original. In one embodiment, the original residue is threonine. In one embodiment, the import residue is arginine (R). In one embodiment, the import residue is phenylalanine (F). In one embodiment, the import residue is tyrosine (Y). In one embodiment, the import residue is tryptophan (W). In one embodiment, the import residue is R, F, Y or W. In one embodiment, a protuberance is generated by replacing two or more residues in a template/original polypeptide. In one embodiment, the Fc polypeptide comprising a protuberance comprises replacement of threonine at position 366 with tryptophan, amino acid numbering according to the EU numbering scheme of Kabat et al. (pp. 688-696 in Sequences of proteins of immunological interest, 5th ed., Vol. 1 (1991; NIH, Bethesda, Md.)).

In some embodiments, the Fc polypeptide comprising a cavity is generated by replacing an original residue in the interface of a template/original polypeptide with an import residue having a smaller side chain volume than the original residue. For example, the Fc polypeptide comprising the cavity may be generated by a method comprising a step wherein nucleic acid encoding an original residue from the interface of said polypeptide is replaced with nucleic acid encoding an import residue having a smaller side chain volume than the original. In one embodiment, the original residue is threonine. In one embodiment, the original residue is leucine. In one embodiment, the original residue is tyrosine. In one embodiment, the import residue is not cysteine (C). In one embodiment, the import residue is alanine (A). In one embodiment, the import residue is serine (S). In one embodiment, the import residue is threonine (T). In one embodiment, the import residue is valine (V). A cavity can be generated by replacing one or more original residues of a template/original polypeptide. For example, in one embodiment, the Fc polypeptide comprising a cavity comprises replacement of two or more original amino acids selected from the group consisting of threonine, leucine and tyrosine. In one embodiment, the Fc polypeptide comprising a cavity comprises two or more import residues selected from the group consisting of alanine, serine, threonine and valine. In some embodiments, the Fc polypeptide comprising a cavity comprises replacement of two or more original amino acids selected from the group consisting of threonine, leucine and tyrosine, and wherein said original amino acids are replaced with import residues selected from the group consisting of alanine, serine, threonine and valine. In one embodiment, the Fc polypeptide comprising a cavity comprises replacement of threonine at position 366 with serine, amino acid numbering according to the EU numbering scheme of Kabat et al., supra. In one embodiment, the Fc polypeptide comprising a cavity comprises replacement of leucine at position 368 with alanine, amino acid numbering according to the EU numbering scheme of Kabat et al., supra. In one embodiment, the Fc polypeptide comprising a cavity comprises replacement of tyrosine at position 407 with valine, amino acid numbering according to the EU numbering scheme of Kabat et al., supra. In one embodiment, the Fc polypeptide comprising a cavity comprises two or more amino acid replacements selected from the group consisting of T366S, L368A and Y407V, amino acid numbering according to the EU numbering scheme of Kabat et al., supra. In some embodiments of these antibody fragments, the Fc polypeptide comprising the protuberance comprises replacement of threonine at position 366 with tryptophan, amino acid numbering according to the EU numbering scheme of Kabat et al., supra.

In various embodiments, the Fc polypeptide of the first and second heavy chain polypeptides may or may not be identical, provided they are capable of dimerizing to form an Fc region (as defined herein). A first Fc polypeptide is generally contiguously linked to one or more domains of an immunoglobulin heavy chain in a single polypeptide, for example with hinge, constant and/or variable domain sequences. In one embodiment, the first Fc polypeptide comprises at least a portion (including all) of a hinge sequence, at least a portion (including all) of a $C_H2$ domain and/or at least a portion (including all) of a $C_H3$ domain. In one embodiment, the first Fc polypeptide comprises the hinge sequence and the $C_H2$ and $C_H3$ domains of an immunoglobulin. In one embodiment, the second Fc polypeptide comprises at least a portion (including all) of a hinge sequence, at least a portion (including all) of a $C_H2$ domain and/or at least a portion (including all) of a $C_H3$ domain. In one embodiment, the second Fc polypeptide comprises the hinge sequence and the $C_H2$ and $C_H3$ domains of an immunoglobulin. In one embodiment, an antibody of the invention comprises first and second Fc polypeptides each of which comprising at least a portion of at least one antibody constant domain. In one embodiment, the antibody constant domain is a $C_H2$ and/or $C_H3$ domain. In any of the embodiments of an antibody of the invention that comprises a constant domain, the antibody constant domain can be from any immunoglobulin class, for example an IgG. The immunoglobulin source can be of any suitable species of origin (e.g., an IgG may be human $IgG_1$) or of synthetic form.

In one embodiment, a first light chain polypeptide and a second light chain polypeptide in a first and second target molecule binding arm, respectively, of an antibody of the invention comprise different/distinct antigen binding determinants (e.g., different/distinct variable domain sequences). In one embodiment, a first light chain polypeptide and a second light chain polypeptide in a first and second target molecule binding arm, respectively, of an antibody of the invention comprise the same (i.e., a common) antigen binding determinant e.g., the same variable domain sequence).

Methods of the invention are capable of generating heteromultimeric molecules at high homogeneity. Accordingly, the invention provides methods wherein at least about 40%, 45%, 50%, 55%, 60%, 65%, 70%, 75%, 80%, 85%, 90%, 95%, 96%, 97%, 98%, 99% of polypeptides are in a complex comprising a first heavy and light chain polypeptide pair and a second heavy and light chain polypeptide pair. In one embodiment, the invention provides methods wherein between about 60 and 99%, 70 and 98%, 75 and 97%, 80 and 96%, 85 and 96%, or 90 and 95% of polypeptides are in a complex comprising a first heavy and light chain polypeptide pair and a second heavy and light chain polypeptide pair.

In one embodiment, an antibody of the invention is selected from the group consisting of IgG, IgE, IgA, IgM and IgD. In some embodiments, the hinge region of an antibody of the invention is preferably of an immunoglobulin selected from the group consisting of IgG, IgA and IgD. For example, in some embodiments, an antibody or hinge region of an antibody is of IgG, which in some embodiments is IgG1 or IgG2 (e.g., IgG2a or IgG2b). In some embodiments, an antibody of the invention is selected from the group consisting of IgG, IgA and IgD. In one embodiment, the antibody is of human, humanized, chimeric or non-human (e.g., murine) origin.

Heteromultimeric proteins of the invention generally are capable of binding, preferably specifically, to antigens. Such antigens include, for example, tumor antigens, cell survival regulatory factors, cell proliferation regulatory factors, molecules associated with (e.g., known or suspected to contribute functionally to) tissue development or differentiation, cell surface molecules, lymphokines, cytokines, molecules involved in cell cycle regulation, molecules involved in vasculogenesis and molecules associated with (e.g., known or suspected to contribute functionally to) angiogenesis. An antigen to which a heteromultimeric protein of the invention is capable of binding may be a member of a subset of one of the above-mentioned categories, wherein the other subset(s) of said category comprise other molecules/antigens that have a distinct characteristic (with respect to the antigen of interest). An antigen of interest may also be deemed to belong to two or more categories. In one embodiment, the invention provides a heteromultimeric protein that binds, preferably specifically, a tumor antigen that is not a cell surface molecule. In one embodiment, a tumor antigen is a cell surface molecule, such as a receptor polypeptide. In another example, in some embodiments, a heteromultimeric protein of the invention binds, preferably specifically, a tumor antigen that is not a cluster differentiation factor. In another example, a heteromultimeric protein of the invention is capable of binding, preferably specifically, to a cluster differentiation factor, which in some embodiments is not, for example, CD3 or CD4. In some embodiments, a heteromultimeric protein of the invention is an anti-VEGF antibody. In some embodiments, a heteromultimeric protein of the invention is a bispecific antibody selected from the group consisting of IL-1alpha/IL-1beta, IL-12/IL-18; IL-13/IL-9; IL-13/IL-4; IL-13/IL-5; IL-5/IL-4; IL-13/IL-(beta; IL-13/IL-25; IL-13/TARC; IL-13/MDC; IL-13/MEF; IL-13/TGF-β; IL-13/LHR agonist; IL-12/TWEAK, IL-13/CL25; IL-13/SPRR2a; IL-13/SPRR2b; IL-13/ADAMS, IL-13/PED2, IL17A/IL17F, CD3/CD19, CD138/CD20; CD138/CD40; CD19/CD20; CD20/CD3; CD38/CD138; CD38/CD20; CD38/CD40; CD40/CD20; CD-8/IL-6; CD20/BR3, TNFalpha/TGF-beta, TNFalpha/IL-1 beta; TNFalpha/IL-2, TNFalpha/IL-3, TNFalpha/IL-4, TNFalpha/IL-5, TNFalpha/IL6, TNFalpha/IL8, TNFalpha/IL-9, TNFalpha/IL-10, TNFalpha/IL-11, TNFalpha/IL-12, TNFalpha/IL-13, TNFalpha/IL-14, TNFalpha/IL-15, TNFalpha/IL-16, TNFalpha/IL-17, TNFalpha/IL-18, TNFalpha/IL-19, TNFalpha/IL-20, TNFalpha/IL-23, TNFalpha/IFNalpha, TNFalpha/CD4, TNFalpha/VEGF, TNFalpha/MIF, TNFalpha/ICAM-1, TNFalpha/PGE4, TNFalpha/PEG2, TNFalpha/RANK ligand, TNFalpha/Te38; TNFalpha/BAFF; TNFalpha/CD22; TNFalpha/CTLA-4; TNFalpha/GP130; TNFα/IL-12p40; VEGF/HER2, VEGF-A/HER2, VEGF-A/PDGF, HER1/HER2, VEGF-A/VEGF-C, VEGF-C/VEGF-D, HER2/DR5, VEGF/IL-8, VEGF/MET, VEGFR/MET receptor, VEGFR/EGFR, HER2/CD64, HER2/CD3, HER2/CD16, HER2/HER3; EGFR/HER2, EGFR/HER3, EGFR/HER4, IL-13/CD40L, IL4/CD40L, TNFR1/IL-1R, TNFR1/IL-6R, TNFR1/IL-18R, EpCAM/CD3, MAPG/CD28, EGFR/CD64, CSPGs/RGM A; CTLA-4/BTNO2; IGF1/IGF2; IGF1/2/Erb2B; MAG/RGM A; NgR/RGM A; NogoA/RGM A; OMGp/RGM A; PDL-I/CTLA-4; and RGM A/RGM B, IL1β/IL18, NRP1/VEGFA, VEGFA/NRP2, cMET/EGFR, ALK1/BMP9, VEGFA/α5β1, HER1/HER3-BU, and CMV. In some embodiments, a heteromultimeric protein of the invention binds to at least two target molecules selected from the group consisting of: α5β1, ALK1, BMP9, IL-1 alpha, IL-1 beta, TARC, MDC, MEF, TGF-β, LHR agonist, TWEAK, CL25, SPRR2a, SPRR2b, ADAM8, PED2, CD3, CD4, CD16, CD19, CD20, CD22, CD28, CD40, CD38, CD64, CD138, CD-8, BR3, TNFalpha, TGF-beta, IL-2, IL-3, IL-4, IL-5, IL-6, IL-8, IL-9, IL-10, IL-11, IL-12, IL-13, IL-14, IL-15, IL-16, IL-17, IL-17A, IL-17F, IL-18, IL-19, IL-20, IL-23, IL-25, IFNalpha, MIF, ICAM-1, PGE4, PEG2, RANK ligand, Te38, BAFF, CTLA-4, GP130, IL-12p40, VEGF, VEGF-A, PDGF, HER1, HER2, HER3, HER3—BU, HER4, VEGF-C, VEGF-D, DR5, cMET, MET, MET receptor, VEGFR, EGFR, CD40L, TNFR1, IL-1R, IL-6R, IL-18R, EpCAM, MAPG, CSPGs, BTNO2, IGF1, IGF2, IGF1/2, Erb2B, MAG, NgR, NogoA, NRP1, NRP2, OMGp, PDL-I, RGM A and RGM B. In some embodiments, a heteromultimeric protein of this invention binds to CD3 and at least one additional target molecule selected from BLR1, BR3, CD19, CD20, CD22, CD72, CD79A, CD79B, CD180 (RP105), CR2, FcRH1, FcRH2, FcRH5, FCER2, FCRL4, HLA-DOB, and NAG14.

First and second host cells in methods of the invention can be cultured in any setting that permits expression and isolation of the polypeptides of interest. For example, in one embodiment, the first host cell and the second host cell in a method of the invention are grown as separate cell cultures. In another embodiment, the first host cell and the second host cell in a method of the invention are grown as a mixed culture comprising both host cells.

In some embodiments, at least one, at least two, at least three or more additional hinge-containing polypeptide expressing host cells may be grown either in the same or separate cultures as the first and/or second hinge-containing host cells. In some embodiments, the additional hinge-containing polypeptide(s) comprises the same heterodimerization domain as the first hinge-containing polypeptide. In some embodiments, the additional hinge-containing polypeptide(s) comprises the same heterodimerization domain as the second hinge-containing polypeptide.

Heteromultimeric proteins may be modified to enhance and/or add additional desired characteristics. Such characteristics include biological functions such as immune effector functions, a desirable in vivo half life/clearance, bioavailability, biodistribution or other pharmacokinetic characteristics. Such modifications are well known in the art and can also be determined empirically, and may include modifications by moieties that may or may not be peptide-based. For example, antibodies may be glycosylated or aglycosylated, generally depending at least in part on the nature of the host cell. Preferably, antibodies of the invention are aglycosylated. An aglycosylated antibody produced by a method of the invention can subsequently be glycosylated by, for example, using in vitro glycosylation methods well known in the art. As described above and herein, heteromultimeric proteins of the invention can be produced in a prokaryotic cell, such as, for example, *E. coli*. *E. coli*-produced heteromultimeric proteins are generally aglycosylated and lack the biological functions normally associated with glycosylation profiles found in mammalian host cell (e.g., CHO) produced heteromultimeric proteins.

The invention also provides immunoconjugates comprising a heteromultimeric protein of the invention conjugated with a heterologous moiety. Any heterologous moiety would be suitable so long as its conjugation to the antibody does not substantially reduce a desired function and/or characteristic of the antibody. For example, in some embodiments, an immunoconjugate comprises a heterologous moiety which is a cytotoxic agent. In some embodiments, said cytotoxic agent is selected from the group consisting of a radioactive isotope, a chemotherapeutic agent and a toxin. In some embodiments, said toxin is selected from the group consisting of calichemicin, maytansine and trichothene. In some embodiments, an immunoconjugate comprises a heterologous moiety which is a detectable marker. In some embodiments, said detectable marker is selected from the group consisting of a radioactive isotope, a member of a ligand-receptor pair, a member of an enzyme-substrate pair and a member of a fluorescence resonance energy transfer pair.

In one aspect, the invention provides compositions comprising a heteromultimeric protein of the invention and a carrier, which in some embodiments is pharmaceutically acceptable.

In another aspect, the invention provides compositions comprising an immunoconjugate as described herein and a carrier, which in some embodiments is pharmaceutically acceptable.

In one aspect, the invention provides a composition comprising a population of multispecific heteromultimeric proteins of the invention. As would be evident to one skilled in the art, generally such a composition would not be completely (i.e., 100%) homogeneous. However, as described herein, methods of the invention are capable of producing a substantially homogeneous population of multispecific heteromultimeric proteins. For example, the invention provides a composition comprising heteromultimeric proteins, wherein at least 40%, 45%, 50%, 55%, 60%, 65%, 70%, 80%, 85%, 90%, 95%, 96%, 97%, 98%, 99% of said heteromultimeric proteins are a multispecific antibody (e.g., a bispecific antibody, etc.) of the invention as described herein.

In one aspect, the invention provides a cell culture comprising a mix of a first host cell and a second host cell, wherein the first host cell comprises nucleic acid encoding a first hinge-containing polypeptide, and the second host cell comprises nucleic acid encoding a second hinge-containing polypeptide, and wherein the two pairs have different target binding specificities. In one aspect, the invention provides a cell culture comprising a mix of a first host cell and a second host cell, wherein the first host cell expresses a first pair of heavy and light chain polypeptides, and the second host cell expresses a second pair of heavy and light chain polypeptides, and wherein the two pairs have different target binding specificities.

In another aspect, the invention provides articles of manufacture comprising a container and a composition contained therein, wherein the composition comprises a heteromultimeric protein (e.g., an antibody) of the invention. In another aspect, the invention provides articles of manufacture comprising a container and a composition contained therein, wherein the composition comprises an immunoconjugate as described herein. In some embodiments, these articles of manufacture further comprise instructions for using said composition.

In yet another aspect, the invention provides polynucleotides encoding a heteromultimeric protein of the invention. In still another aspect, the invention provides polynucleotides encoding an immunoconjugate as described herein.

In one aspect, the invention provides recombinant vectors for expressing a molecule (e.g., an antibody) of the invention. In another aspect, the invention provides recombinant vectors for expressing an immunoconjugate of the invention.

Any of a number of host cells can be used in methods of the invention. Such cells are known in the art (some of which are described herein) or can be determined empirically with respect to suitability for use in methods of the invention using routine techniques known in the art. In one embodiment, a host cell is prokaryotic. In some embodiments, a host cell is a gram-negative bacterial cell. In one embodiment, a host cell is *E. coli*. In some embodiments, the *E. coli* is of a strain deficient in lipoprotein (Δlpp). In some embodiments, the genotype of an *E. coli* host cell lacks degP and prc genes and harbors a mutant spr gene. In one embodiment, a host cell is mammalian, for example, a Chinese Hamster Ovary (CHO) cell.

In one aspect, the invention provides host cells comprising a polynucleotide or recombinant vector of the invention. In one embodiment, a host cell is a mammalian cell, for example a Chinese Hamster Ovary (CHO) cell. In one embodiment, a host cell is a prokaryotic cell. In some embodiments, a host cell is a gram-negative bacterial cell, which in some embodiments is *E. coli*. Host cells of the invention may further comprise a polynucleotide or recombinant vector encoding a molecule the expression of which in a host cell enhances yield of a heteromultimeric protein in a method of the invention. For example, such molecule can be a chaperone protein. In one embodiment, said molecule is a prokaryotic polypeptide selected from the group consisting of DsbA, DsbC, DsbG and FkpA. In some embodiments, said polynucleotide or recombinant vector encodes both DsbA and DsbC. In some embodiments, an *E. coli* host cell is of a strain deficient in endogenous protease activities. In some embodiments, the genotype of an *E. coli* host cell is that of an *E. coli* strain that lacks degP and prc genes and harbors a mutant spr gene. In some embodiments, the genotype of an *E. coli* host cell is Δlpp.

Heteromultimeric proteins of the invention find a variety of uses in a variety of settings. In one example, a heteromultimeric protein of the invention is a therapeutic antibody. In another example, a heteromultimeric protein of the invention is an agonist antibody. In another example, a heteromultimeric protein of the invention is an antagonistic antibody. A heteromultimeric protein of the invention may also be a diagnostic antibody. In yet another example, a heteromultimeric protein of the invention is a blocking antibody. In another example, a heteromultimeric protein of the invention is a neutralizing antibody.

In one aspect, the invention provides methods of treating or delaying a disease in a subject, said methods comprising administering a heteromultimeric protein of the invention to said subject. In one embodiment, the disease is cancer. In another embodiment, the disease is associated with dysregulation of angiogenesis. In another embodiment, the disease is an immune disorder, such as rheumatoid arthritis, immune thrombocytopenic purpura, systemic lupus erythematosus, etc.

In one aspect, the invention provides use of a heteromultimeric protein (e.g., an antibody) of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a nucleic acid of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an expression vector of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a host cell of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of an article of manufacture of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

In one aspect, the invention provides use of a kit of the invention in the preparation of a medicament for the therapeutic and/or prophylactic treatment of a disease, such as a cancer, a tumor, a cell proliferative disorder, an immune (such as autoimmune) disorder and/or an angiogenesis-related disorder.

Other objects, features and advantages of the present invention will become apparent from the following detailed description. It should be understood, however, that the detailed description and specific examples, while indicating preferred embodiments of the invention, are given by way of illustration only, since various changes and modifications within the scope and spirit of the invention will become apparent to one skilled in the art from this detailed description.

BRIEF DESCRIPTION OF THE DRAWINGS

FIG. 9E-1 and FIG. 9E-2 show two HIC chromatograms for two co-cultures that had different cell ratios in the initial fermentation inoculum as indicated. A clear difference in the product is observed that reflects the initial inoculum ratio. Using this approach it becomes apparent that the initial inoculum ratio can be altered to achieve optimum production of the heteromultimeric protein.

ABBREVIATIONS

Figure 1B:
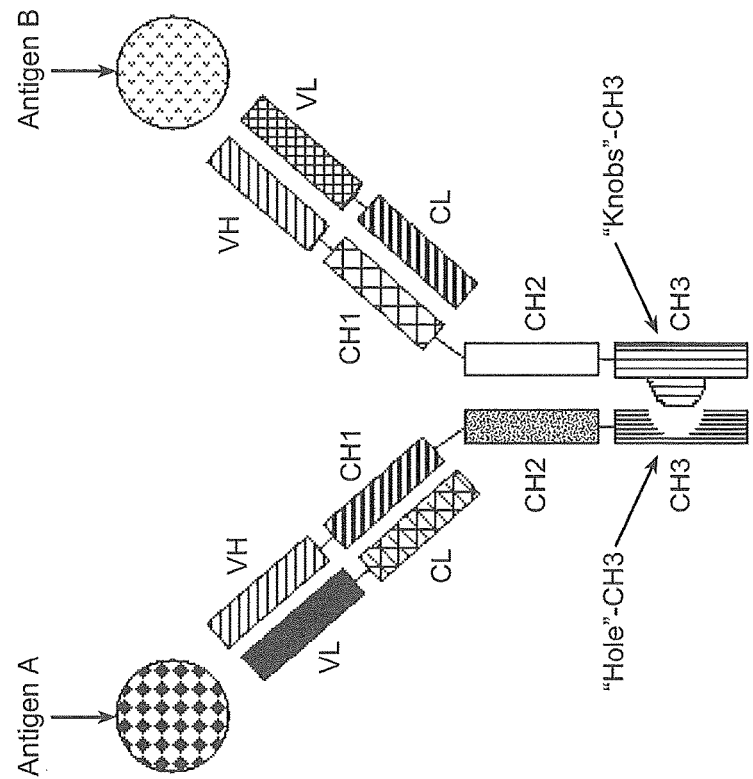
FIG. 1B illustrates a full-length bispecific antibody. Not depicted are the inter-heavy chain disulfide bonds in the hinge region.

ADCC=Antibody-dependent cell-mediated cytotoxicity
API=Anti-pathogen immunoadhesins
BPI=Bactericidal/permeability-increasing protein
C1q=Complement factor 1q
CD=Cluster of Differentiation
CDC=Complement-dependent cytotoxicity
CH1 or $C_H1$=Heavy chain first constant domain
CH2 or $C_H2$=Heavy chain second constant domain
CH3 or $C_H3$=Heavy chain third constant domain
CH4 or $C_H4$=Heavy chain fourth constant domain
CL or $C_L$=Light chain constant domain
CTLA=Cytotoxic T lymphocyte-associated molecule
Fc=Fragment crystallizable
FcγR=Receptor gamma for the Fc portion of IgG
HIV=Human immunodeficiency virus
ICAM=Intercellular adhesion molecule
BsAb=Bispecific antibody
BsDb=Bispecific diabody
dsFv=Disulfide-stabilized Fv
Fc=Constant fragment of an antibody
Fd=$V_H$+$C_H1$ of an antibody
FcR=Fc receptor
Fv=Variable fragment of an antibody
IgG=Immunoglobulin G
mAb=Monoclonal antibody
PBL=Peripheral blood lymphocyte
scDb=Single-chain diabody
scFv=Single-chain Fv
$(scFv)_2$=scFv-scFv tandem
Tandab=Tandem diabody
VH or $V_H$=Variable domain of the heavy chain of an antibody
VL or $V_L$=Variable domain of the light chain of an antibody

DETAILED DESCRIPTION

The invention will now be described in detail by way of reference only using the following definitions and examples.

All patents and publications, including all sequences disclosed within such patents and publications, referred to herein are expressly incorporated by reference.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, N.Y. (1991) provide one of skill with a general dictionary of many of the terms used in this invention. Although any methods and materials similar or equivalent to those described herein can be used in the practice or testing of the present invention, the preferred methods and materials are described. Numeric ranges are inclusive of the numbers defining the range. Unless otherwise indicated, nucleic acids are written left to right in 5' to 3' orientation; amino acid sequences are written left to right in amino to carboxy orientation, respectively. Practitioners are particularly directed to Sambrook et al., 1989, and Ausubel F M et al., 1993, for definitions and terms of the art. It is to be understood that this invention is not limited to the particular methodology, protocols, and reagents described, as these may vary.

Numeric ranges are inclusive of the numbers defining the range.

Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

I. DEFINITIONS

A "heteromultimer", "heteromultimeric complex", or "heteromultimeric protein" refers to a molecule comprising at least a first hinge-containing polypeptide and a second hinge-containing polypeptide, wherein the second hinge-containing polypeptide differs in amino acid sequence from the first hinge-containing polypeptide by at least one amino acid residue. The heteromultimer can comprise a "heterodimer" formed by the first and second hinge-containing polypeptides or can form higher order tertiary structures where polypeptides in addition to the first and second hinge-containing polypeptides are present. The polypeptides of the heteromultimer may interact with each other by a non-peptidic, covalent bond (e.g., disulfide bond) and/or a non-covalent interaction (e.g., hydrogen bonds, ionic bonds, van der Waals forces, and/or hydrophobic interactions).

As used herein, "heteromultimerization domain" refers to alterations or additions to a biological molecule so as to promote heteromultimer formation and hinder homomultimer formation. Any heterodimerization domain having a strong preference for forming heterodimers over homodimers is within the scope of the invention. Illustrative examples include but are not limited to, for example, US Patent Application 20030078385 (Arathoon et al.—Genentech; describing knob into holes); WO2007147901 (Kjærgaard et al.—Novo Nordisk: describing ionic interactions); WO 2009089004 (Kannan et al.—Amgen: describing electrostatic steering effects); U.S. Provisional Patent Application 61/243,105 (Christensen et al.—Genentech; describing coiled coils). See also, for example, Pack, P. & Plueckthun, A., Biochemistry 31, 1579-1584 (1992) describing leucine zipper or Pack et al., Bio/Technology 11, 1271-1277 (1993) describing the helix-turn-helix motif. The phrase "heteromultimerization domain" and "heterodimerization domain" are used interchangeably herein.

The phrase "hinge-containing polypeptide" as used herein refers to a polypeptide that comprises a region corresponding to the hinge region of an immunoglobulin as understood in the art, e.g., the region between the $C_H1$ and $C_H2$ domains of the heavy chain. The "hinge region," "hinge sequence", and variations thereof, as used herein, includes the meaning known in the art, which is illustrated in, for example, Janeway's Immunobiology, (Garland Science, Taylor & Francis Group, LLC, NY) (7th ed., 2008); Bloom et al., *Protein Science* (1997), 6:407-415; Humphreys et al., *J. Immunol. Methods* (1997), 209:193-202. See also, for example, Burton, Molec. Immunol. 22:161-206 (1985) and Papadea, C. and I. J. Check (1989) "Human immunoglobulin G and immunoglobulin G subclasses: biochemical, genetic, and clinical aspects." Crit. Rev Clin Lab Sci 27(1): 27-58. It will be appreciated by one skilled in the art that the number of amino acids as well as the number of cysteine residues available for interchain disulfide bond formation varies between the classes and isotypes of immunoglobulins. All such hinge regions may be in the hinge-containing polypeptides and are within the scope of the invention.

The term "antibody" herein is used in the broadest sense and refers to any immunoglobulin (Ig) molecule comprising two heavy chains and two light chains, and any fragment, mutant, variant or derivation thereof so long as they exhibit the desired biological activity (e.g., epitope binding activity). Examples of antibodies include monoclonal antibodies, polyclonal antibodies, multispecific antibodies (e.g., bispecific antibodies) and antibody fragments as described herein. An antibody can be human, humanized and/or affinity matured.

As a frame of reference, as used herein an antibody will refer to the structure of an immunoglobulin G (IgG). However, one skilled in the art would understand/recognize that an antibody of any immunoglobulin class may be utilized in the inventive method described herein. For clarity, an IgG molecule contains a pair of identical heavy chains (HCs) and a pair of identical light chains (LCs). Each LC has one variable domain ($V_L$) and one constant domain ($C_L$), while each HC has one variable ($V_H$) and three constant domains ($C_H1$, $C_H2$, and $C_H3$). The $C_H1$ and $C_H2$ domains are connected by a hinge region. This structure is well known in the art. Reference is made to FIG. 1B.

Figure 1A:
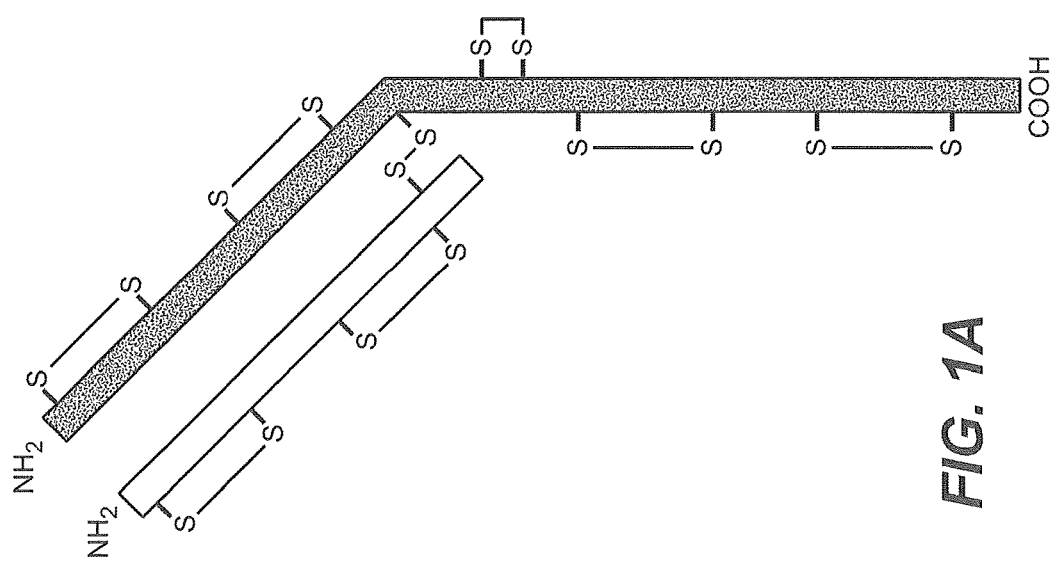
FIG. 1A illustrates a fully oxidized half-antibody. Not shown are the "knob" or "hole" or other heterodimerization domains. The half-antibody depicted in this figure is an IgG1 isotype. One skilled in the art will appreciate that the other immunoglobulin isotypes can be envisioned as half-antibodies with the corresponding inter- and intra-chain bonds. In an intact Ab the hinge cysteines will form inter-chain disulfide bonds.

As used herein, "half-antibody" refers to one immunoglobulin heavy chain associated with one immunoglobulin light chain. An exemplary half-antibody is depicted in FIG. 1A. One skilled in the art will readily appreciate that a half-antibody may also have an antigen binding domain consisting of a single variable domain.

Figure 8A:
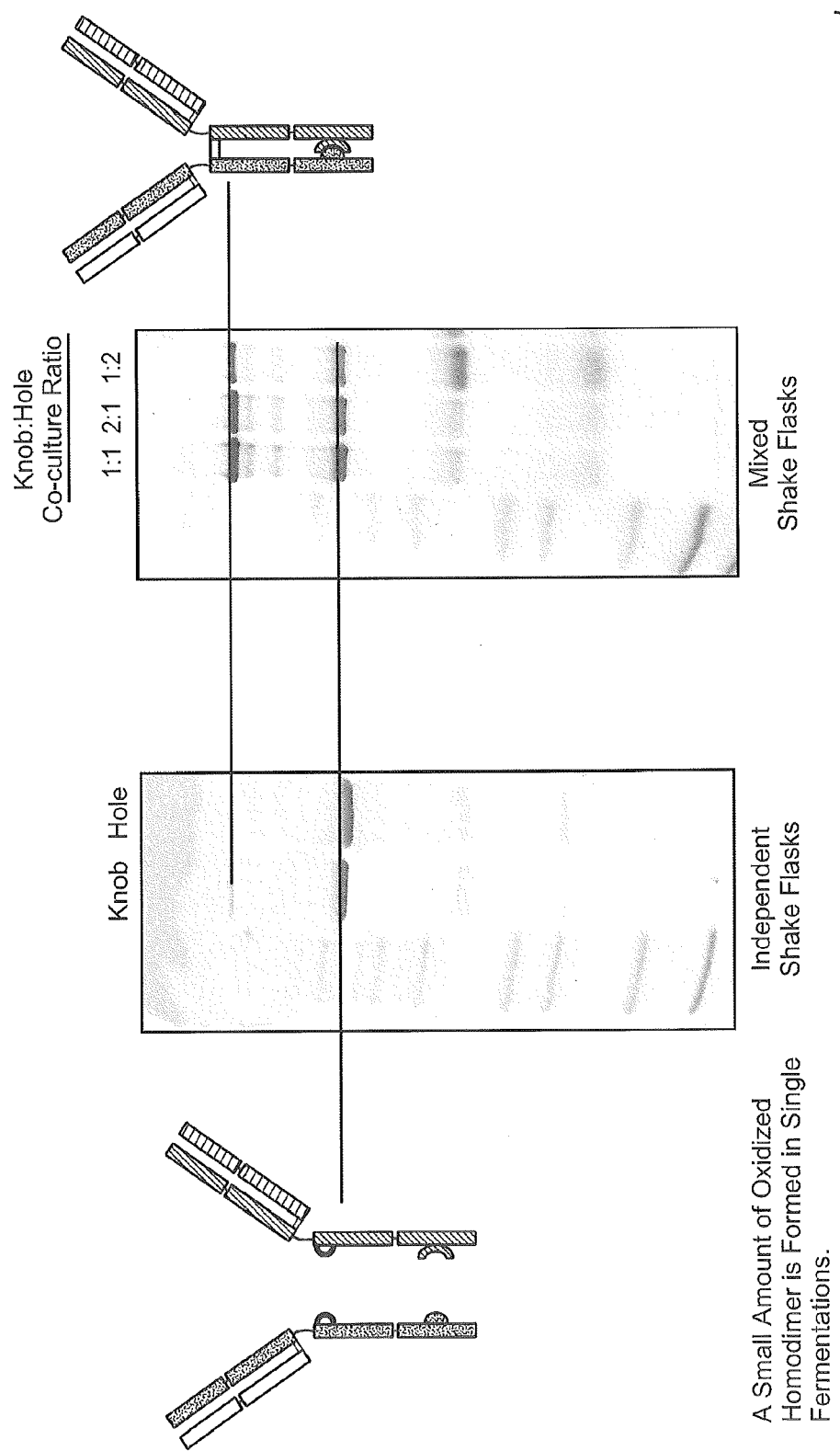
FIG. 8A is a photograph of two polyacrylamide gels comparing the bispecific antibody production when the cells are cultured separately to a co-culture of the cells expressing the half-antibodies. The intact bispecific forms to a much higher level under co-culture conditions. When half-antibodies are expressed and purified independently then mixed, the half-antibodies form less than 5% of the intact bispecific. Under co-culture conditions, greater than 40% is an intact bispecific as determined by 150 kD/(150 kD+75 kD) using L1-Core protein determinations.
Figure 9A:
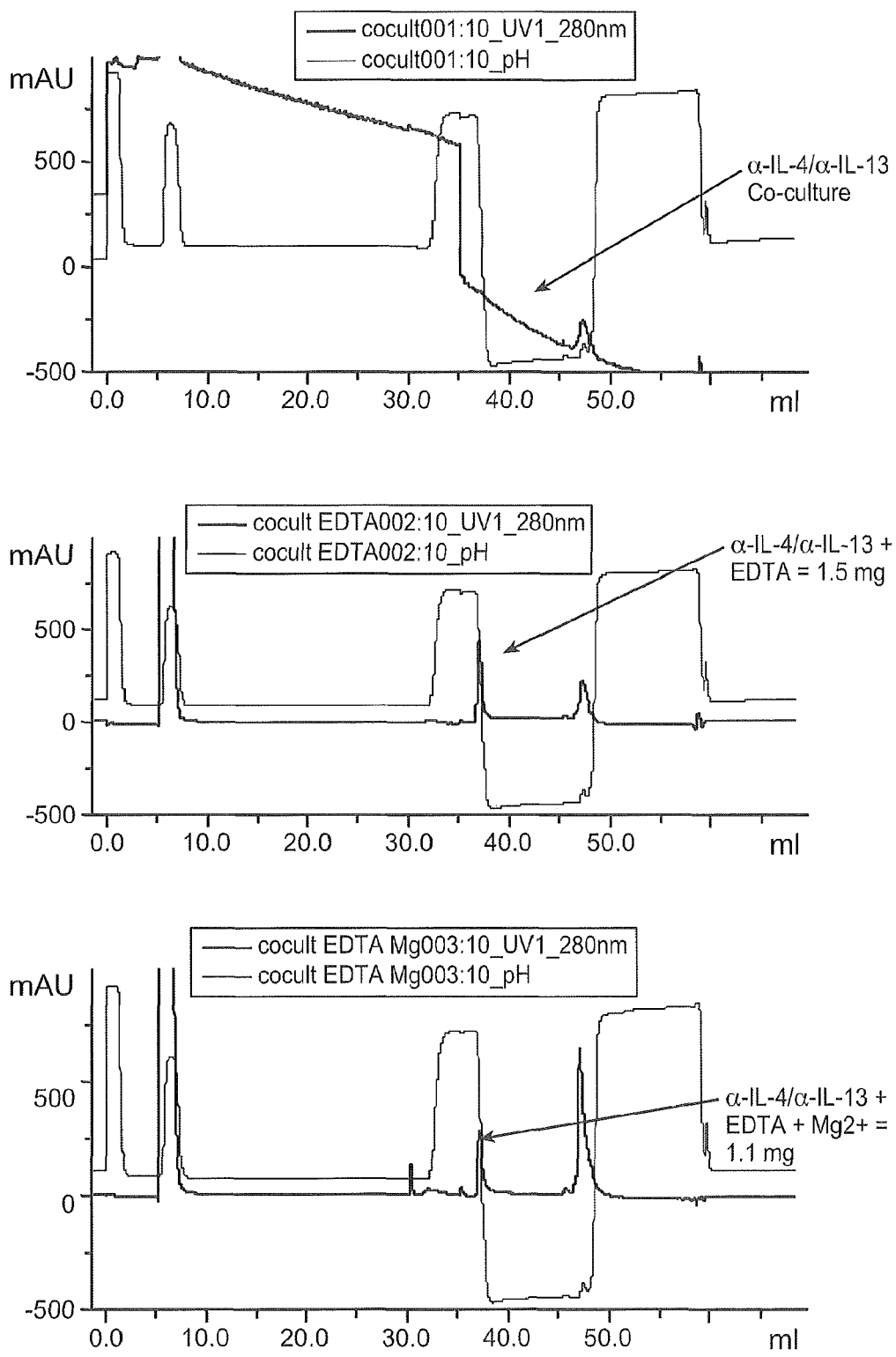
FIG. 9A show three chromatograms. The top chromatogram shows no absorbance peak during the elution for the sample without EDTA. The middle chromatogram shows the sample with EDTA has a distinct elution peak from which we recovered approximately 1.5 mg protein. The lower chromatogram shows the sample treated with EDTA and Mg also showed a similar elution peak from which we recovered 1.1 mg protein. Recovered proteins from the EDTA sample, EDTA plus Mg sample, and a pool of fractions from the same retention time from the untreated EDTA sample were analyzed by SDS-PAGE under reducing and non-reducing conditions.
Figure 9B:
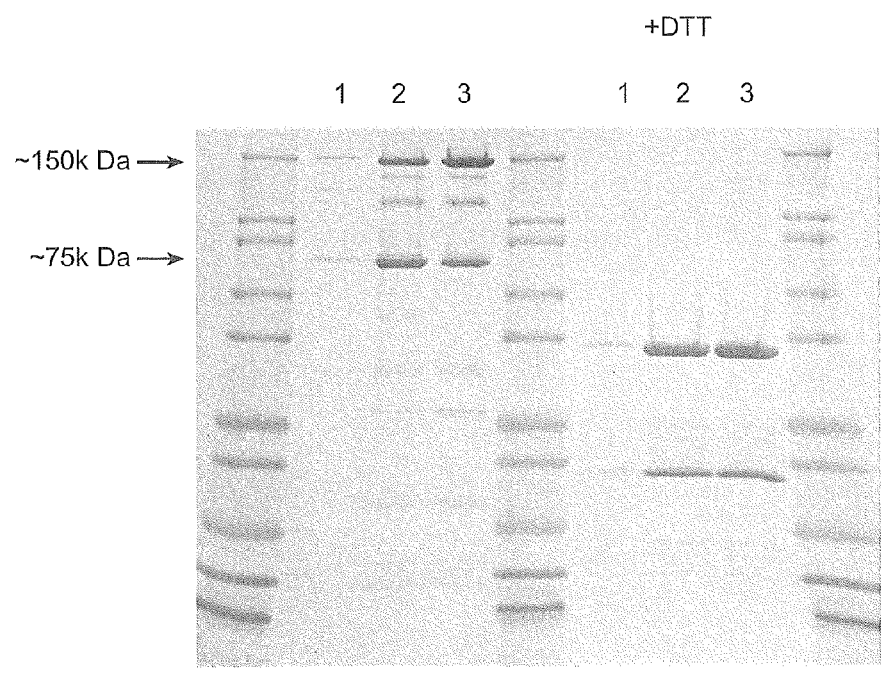
FIG. 9B is a photograph of the SDS-PAGE gel described in FIG. 9A. The samples treated with EDTA have produced intact bispecific antibody that has been released into the culture media.
Figures 1, 9C:
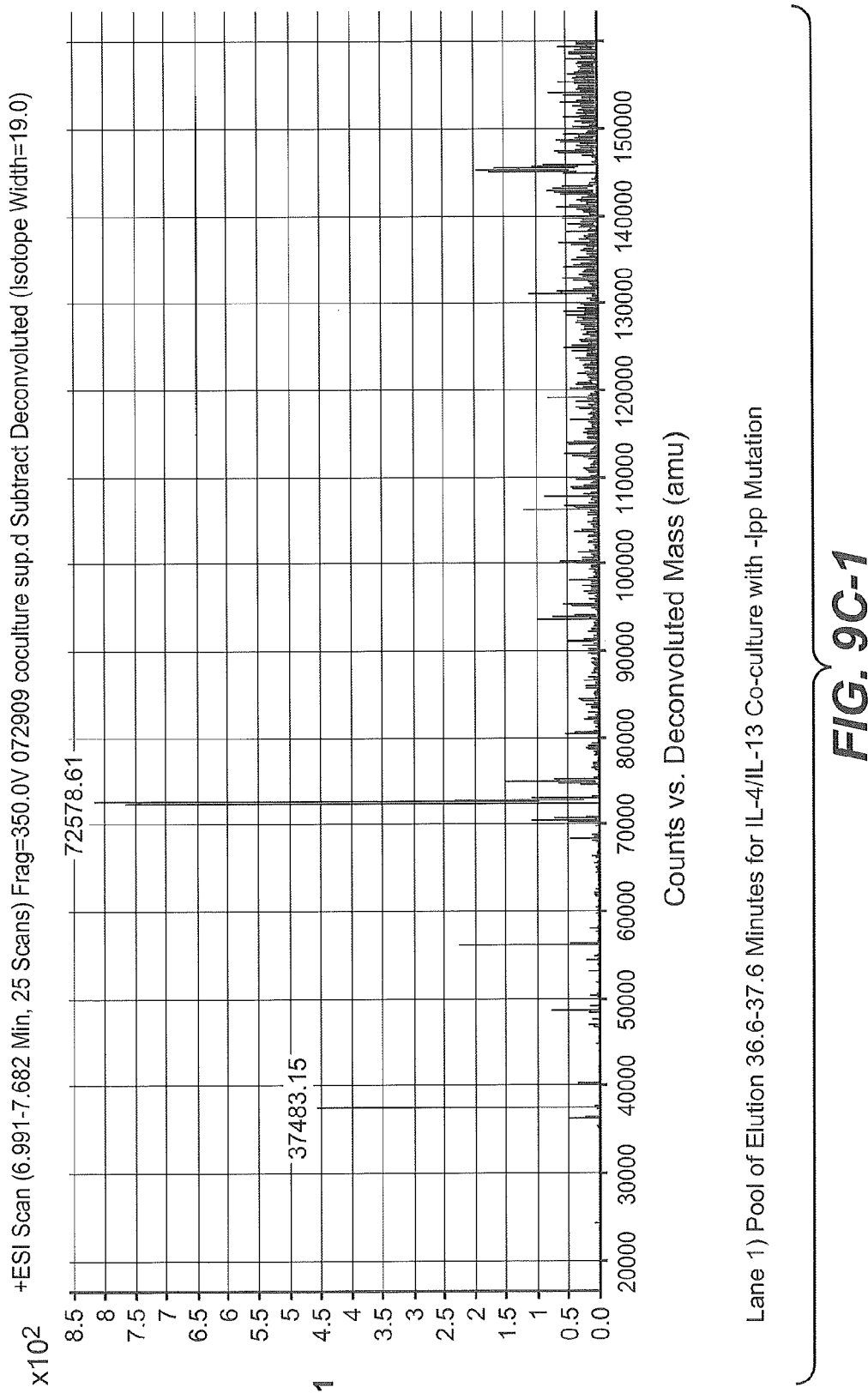
Figures 2, 9C:
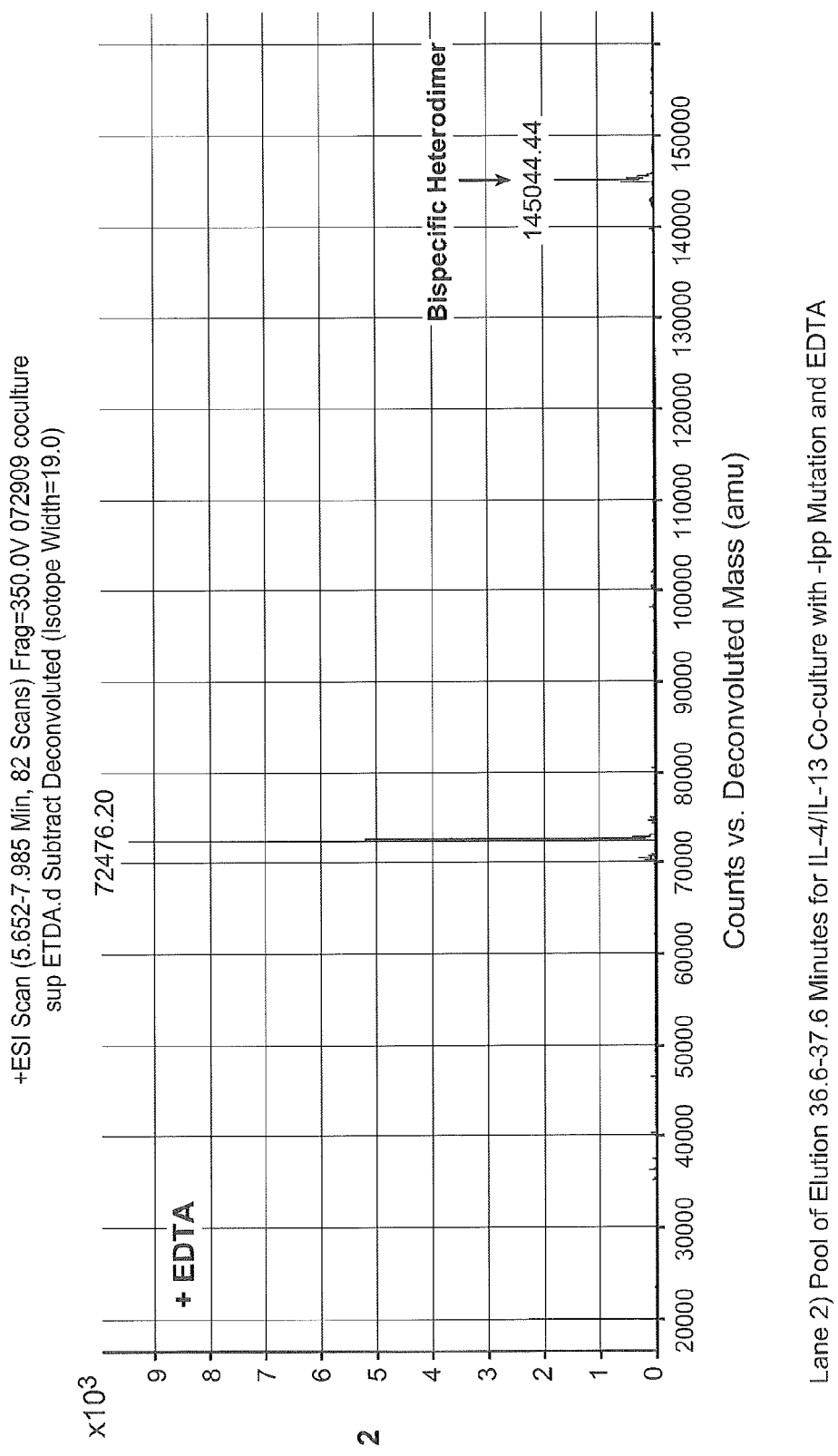
Figures 3, 9C:
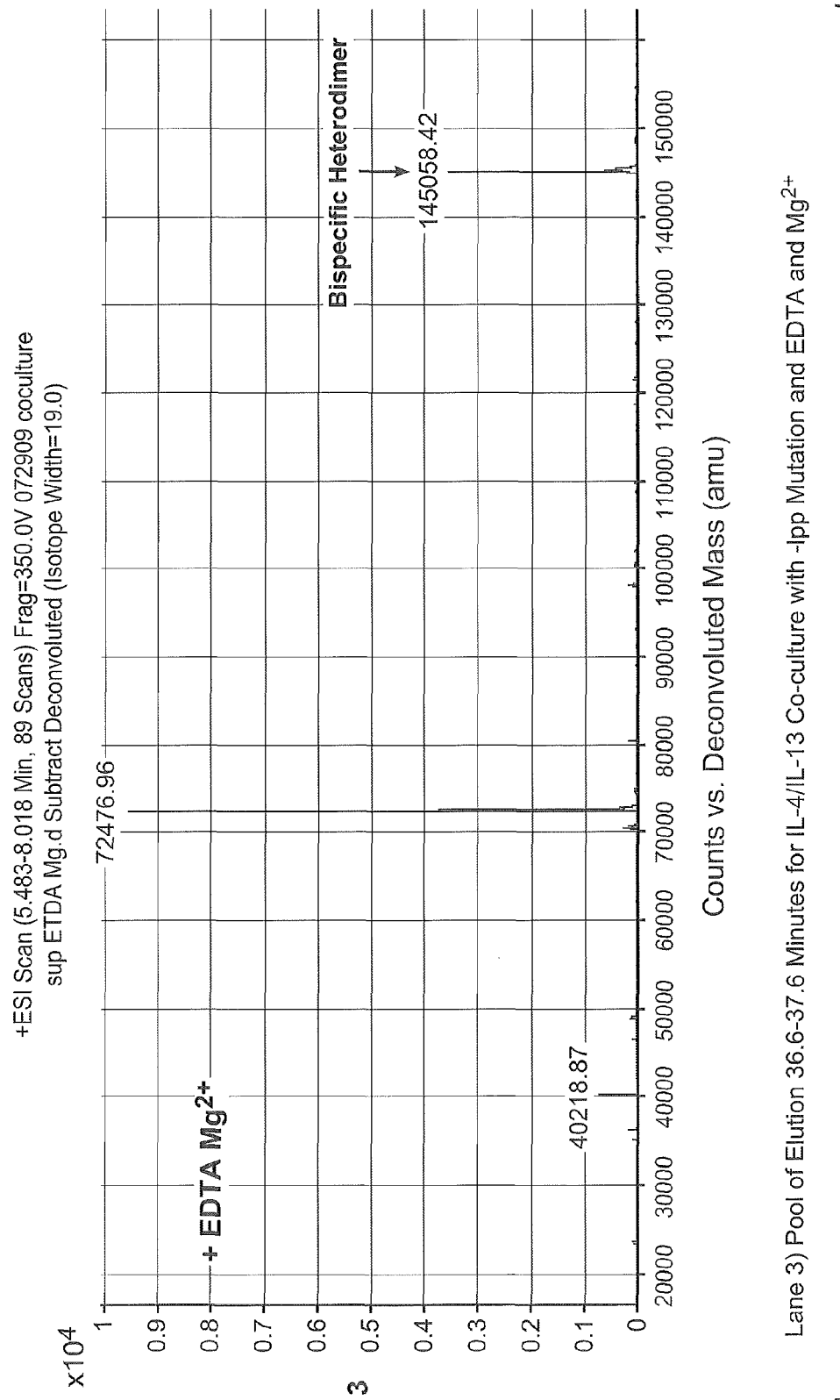
Figure 9D:
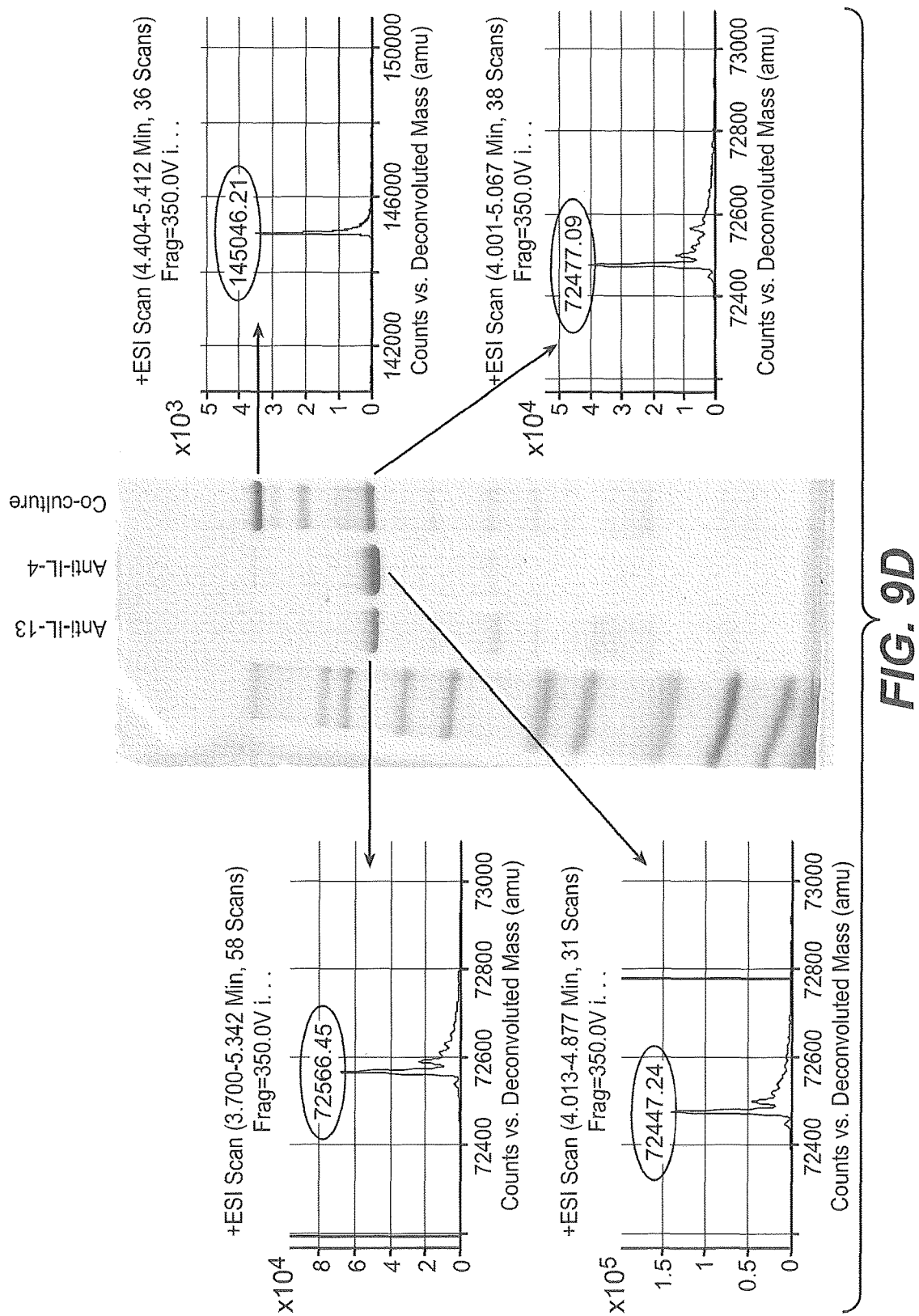
FIG. 9D is a photograph of a SDS-PAGE gel and mass chromatograms of the indicated bands. Lane is MW markers, Lane 2 is anti-IL-13 independently expressed, Lane 3 is antiI-IL-4 independently expressed and Lane 4 is a co-culture of the two cells. Mass spec analysis of all three samples shows that the co-culture produces the intact bispecific and an excess of one half-antibody, anti-IL-4. This indicates the anti-IL-13 half-antibody is stoichiometrically limiting. When half-antibodies are expressed and purified independently then mixed, the half-antibodies form approximately 2% (anti-IL-13) and 3% (anti-IL-4) of the intact bispecific. Under co-culture conditions, approximately 60% is an intact bispecific as determined by 150 kD/(150 kD+75 kD) using L1-Core protein determinations.

The term "maxibody" refers to a fusion protein comprising a scFv fused to an Fc polypeptide. Reference is made to FIG. 8a of WO 2009089004. Reference is made to FIG. 2 of WO 2009089004 for a bispecific maxibody.

The term "$C_H2$ domain" of a human IgG Fc region usually extends from about residues 231 to about 340 of the IgG according to the EU numbering system. The $C_H2$ domain is unique in that it is not closely paired with another domain. Rather, two N-linked branched carbohydrate chains are interposed between the two $C_H2$ domains of an intact native IgG molecule. It has been speculated that the carbohydrate may provide a substitute for the domain-domain pairing and help stabilize the $C_H2$ domain. Burton, Molec. Immunol. 22:161-206 (1985).

The term "$C_H3$ domain" comprises the stretch of residues C-terminal to a $C_H2$ domain in an Fc region (i.e., from about amino acid residue 341 to about amino acid residue 447 of an IgG according to the EU numbering system).

The term "Fc region", as used herein, generally refers to a dimer complex comprising the C-terminal polypeptide sequences of an immunoglobulin heavy chain, wherein a C-terminal polypeptide sequence is that which is obtainable by papain digestion of an intact antibody. The Fc region may comprise native or variant Fc sequences. Although the boundaries of the Fc sequence of an immunoglobulin heavy chain might vary, the human IgG heavy chain Fc sequence is usually defined to stretch from an amino acid residue at about position Cys226, or from about position Pro230, to the carboxyl terminus of the Fc sequence. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991. The Fc sequence of an immunoglobulin generally comprises two constant domains, a $C_H2$ domain and a $C_H3$ domain, and optionally comprises a $C_H4$ domain. By "Fc polypeptide" herein is meant one of the polypeptides that make up an Fc region, e.g., a monomeric Fc. An Fc polypeptide may be obtained from any suitable immunoglobulin, such as $IgG_1$, $IgG_2$, $IgG_3$, or $IgG_4$ subtypes, IgA, IgE, IgD or IgM. The Fc region comprises the carboxy-terminal portions of both H chains held together by disulfides. The effector functions of antibodies are determined by sequences in the Fc region; this region is also the part recognized by Fc receptors (FcR) found on certain types of cells. In some embodiments, an Fc polypeptide comprises part or all of a wild type hinge sequence (generally at its N terminus). In some embodiments, an Fc polypeptide does not comprise a functional or wild type hinge sequence.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g., B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human $IgG_1$ Fc region (non-A and A allotypes); native sequence human $IgG_2$ Fc region; native sequence human $IgG_3$ Fc region; and native sequence human $IgG_4$ Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g., from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95%, at least about 96%, at least about 97%, at least about 98% or at least about 99% homology therewith.

"Fc component" as used herein refers to a hinge region, a $C_H2$ domain or a $C_H3$ domain of an Fc region.

In certain embodiments, the hinge-containing polypeptide comprises an IgG Fc region, preferably derived from a wild-type human IgG Fc region. By "wild-type" human IgG Fc it is meant a sequence of amino acids that occurs naturally within the human population. Of course, just as the Fc sequence may vary slightly between individuals, one or more alterations may be made to a wildtype sequence and still remain within the scope of the invention. For example, the Fc region may contain additional alterations that are not related to the present invention, such as a mutation in a glycosylation site or inclusion of an unnatural amino acid.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., *J. Immunol.* 150:880-887 (1993); Clarkson et al., *Nature* 352: 624-628 (1991).

The term "Fab" as used herein refers to an antigen-binding fragment of an antibody. As noted above, papain may be used to digest an intact antibody. Papain digestion of antibodies produces two identical antigen-binding fragments, i.e., "Fab" fragments, and a residual "Fc" fragment (i.e., the Fc region, supra). The Fab fragment consists of an entire L chain along with the variable region domain of the H chain ($V_H$), and the first constant domain of one heavy chain ($C_H1$).

The phrase "antigen binding arm", "target molecule binding arm", "target binding arm" and variations thereof, as used herein, refers to a component part of a heteromultimeric protein of the invention that has an ability to specifically bind a target of interest. Generally and preferably, the antigen binding arm is a complex of immunoglobulin polypeptide sequences, e.g., CDR and/or variable domain sequences of an immunoglobulin light and heavy chain.

A "target" or "target molecule" refers to a moiety recognized by a binding arm of the heteromultimeric protein. For example, if the heteromultimeric protein is an antibody, then the target may be epitopes on a single molecule or on different molecules, or a pathogen or a tumor cell, depending on the context. Similarly, if the heteromultimeric protein is a receptor-Fc fusion protein the target would be the cognate binding partner for the receptor. One skilled in the art will appreciate that the target is determined by the binding specificity of the target binding arm and that different target binding arms may recognize different targets. A target preferably binds to a heteromultimeric protein of this invention with affinity higher than 1 uM Kd (according to scatchard analysis). Examples of target molecules include, but are not limited to, serum soluble proteins and/or their receptors, such as cytokines and/or cytokine receptors, adhesins, growth factors and/or their receptors, hormones, viral particles (e.g., RSV F protein, CMV, StaphA, influenza, hepatitis C virus), micoorganisms (e.g., bacterial cell proteins, fungal cells), adhesins, CD proteins and their receptors.

One example of an "intact" or "full-length" antibody is one that comprises an antigen-binding arm as well as a $C_L$ and at least heavy chain constant domains, $C_H1$, $C_H2$, and $C_H3$. The constant domains can be native sequence constant domains (e.g., human native sequence constant domains) or amino acid sequence variants thereof.

The term "coupling" as used herein refers to the steps necessary to link the first and second hinge-containing polypeptides to each other, e.g., formation of a covalent bond. Such steps comprise the reducing, annealing and/or oxidizing of cysteine residues in the first and second hinge-containing polypeptides to form an inter-chain disulfide bond. The coupling may be achieved by chemical cross-linking or the use of a redox system. See, e.g., Humphreys et al., J. Immunol. Methods (1998) 217:1-10 and Zhu et al., Cancer Lett., (1994) 86: 127-134.

The term "multispecific antibody" is used in the broadest sense and specifically covers an antibody that has poly-epitopic specificity. Such multispecific antibodies include, but are not limited to, an antibody comprising a heavy chain variable domain ($V_H$) and a light chain variable domain ($V_L$), wherein the $V_HV_L$ unit has polyepitopic specificity, antibodies having two or more $V_L$ and $V_H$ domains with each $V_HV_L$ unit binding to a different epitope, antibodies having two or more single variable domains with each single variable domain binding to a different epitope, full length antibodies, antibody fragments such as Fab, Fv, dsFv, scFv, diabodies, bispecific diabodies and triabodies, antibody fragments that have been linked covalently or non-covalently. "Polyepitopic specificity" refers to the ability to specifically bind to two or more different epitopes on the same or different target(s). "Monospecific" refers to the ability to bind only one epitope. According to one embodiment the multispecific antibody is an IgG antibody that binds to each epitope with an affinity of 5 μM to 0.001 pM, 3 μM to 0.001 pM, 1 μM to 0.001 pM, 0.5 μM to 0.001 pM, or 0.1 μM to 0.001 pM. An illustrative drawing of a bispecific is provided in FIG. 1B.

"Antibody fragments" comprise a portion of an intact antibody, preferably the antigen binding or a variable region of the intact antibody. Examples of antibody fragments include Fab, Fab', F(ab')$_2$, and Fv fragments; diabodies (Db); tandem diabodies (taDb), linear antibodies (e.g., U.S. Pat. No. 5,641,870; Zapata et al., Protein Eng. 8(10):1057-1062 (1995)); one-armed antibodies, single variable domain antibodies, minibodies, single-chain antibody molecules; and multispecific antibodies formed from antibody fragments (e.g., including but not limited to, Db-Fc, taDb-Fc, taDb-$C_H3$ and (scFV)4-Fc).

The expression "single domain antibodies" (sdAbs) or "single variable domain (SVD) antibodies" generally refers to antibodies in which a single variable domain ($V_H$ or $V_L$) can confer antigen binding. In other words, the single variable domain does not need to interact with another variable domain in order to recognize the target antigen. Single domain antibodies consist of a single monomeric variable antibody domain ($V_H$ or $V_L$) on each antigen binding arm. Examples of single domain antibodies include those derived from camelids (llamas and camels) and cartilaginous fish (e.g., nurse sharks) and those derived from recombinant methods from humans and mouse antibodies (Ward et al., Nature (1989) 341:544-546; Dooley and Flajnik, Dev Comp Immunol (2006) 30:43-56; Muyldermans et al., Trend Biochem Sci (2001) 26:230-235; Holt et al., Trends Biotechnol (2003):21:484-490; WO 2005/035572; WO 03/035694; Davies and Riechmann, Febs Lett (1994) 339:285-290; WO00/29004; WO 02/051870). A single variable domain antibody can be present in an antigen binding arm (e.g., homo- or hetero-multimer) with other variable regions or variable domains, in which case it is not a single domain antibody.

The expression "linear antibodies" generally refers to the antibodies described in Zapata et al., Protein Eng. 8(10):1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

The term "knob-into-hole" or "KnH" technology as mentioned herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, $C_L$:$C_H1$ interfaces or $V_H$/$V_L$ interfaces of antibodies (e.g., US2007/0178552, WO 96/027011, WO 98/050431 and Zhu et al. (1997) Protein Science 6:781-788). This is especially useful in driving the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

"Fv" consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although often at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains, which enables the sFv to form the desired structure for antigen binding. For a review of sFv, see Pluckthun, The Pharmacology of Monoclonal Antibodies, vol. 113, Rosenburg and Moore eds., Springer-Verlag, New York, pp. 269-315 (1994); Malmborg et al., J. Immunol. Methods 183:7-13, 1995.

The term "diabodies" refers to small antibody fragments prepared by constructing sFv fragments (see preceding paragraph) with short linkers (about 5-10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "cross-over" sFv fragments in which the $V_H$ and $V_L$ domains of the two antibodies are present on different polypeptide chains. Diabodies are described more fully in, for example, EP 404,097; WO 93/11161; and Hollinger et al., Proc. Natl. Acad. Sci. USA 90:6444-6448 (1993).

The term "one-armed antibody" or "one-armed antibodies" refers to an antibody that comprises (1) a variable domain joined by a peptide bond to polypeptide comprising a $C_H2$ domain, a $C_H3$ domain or a $C_H2$-$C_H3$ domain and (2) a second $C_H2$, $C_H3$ or $C_H2$-$C_H3$ domain, wherein a variable domain is not joined by a peptide bond to a polypeptide comprising the second $C_H2$, $C_H3$ or $C_H2$-$C_H3$ domain. In one embodiment, the one-armed antibody comprises 3 polypeptides (1) a first polypeptide comprising a variable domain (e.g., $V_H$), $C_H1$, $C_H2$ and $C_H3$, (2) a second polypeptide comprising a variable domain (e.g., $V_L$) and a $C_L$ domain, and (3) a third polypeptide comprising a $C_H2$ and $C_H3$ domain. In another embodiment, the one-armed antibody has a partial hinge region containing the two cysteine residues which form disulphide bonds linking the constant heavy chains. In one embodiment, the variable domains of the one armed antibody form an antigen binding region. In another embodiment, the variable domains of the one armed antibody are single variable domains, wherein each single variable domain is an antigen binding region. In an embodiment, the one-armed antibody is a single variable domain antibody.

Antibodies of the invention can be "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, provided that they exhibit the desired biological activity (U.S. Pat. No. 4,816,567; and Morrison et al., Proc. Natl. Acad. Sci. USA 81:6851-6855 (1984)). Chimeric antibodies of interest herein include primatized antibodies comprising variable domain antigen-binding sequences derived from a non-human primate (e.g., Old World Monkey, Ape, etc.) and human constant region sequences.

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

"Peptibody" or "peptibodies" refers to a fusion of randomly generated peptides with an Fc domain. See U.S. Pat. No. 6,660,843, issued Dec. 9, 2003 to Feige et al. (incorporated by reference in its entirety). They include one or more peptides linked to the N-terminus, C-terminus, amino acid sidechains, or to more than one of these sites. Peptibody technology enables design of therapeutic agents that incorporate peptides that target one or more ligands or receptors, tumor-homing peptides, membrane-transporting peptides, and the like. Peptibody technology has proven useful in design of a number of such molecules, including linear and disulfide-constrained peptides, "tandem peptide multimers" (i.e., more than one peptide on a single chain of an Fc domain). See, for example, U.S. Pat. No. 6,660,843; U.S. Pat. App. No. 2003/0195156, published Oct. 16, 2003 (corresponding to WO 02/092620, published Nov. 21, 2002); U.S. Pat. App. No. 2003/0176352, published Sep. 18, 2003 (corresponding to WO 03/031589, published Apr. 17, 2003); U.S. Ser. No. 09/422,838, filed Oct. 22, 1999 (corresponding to WO 00/24770, published May 4, 2000); U.S. Pat. App. No. 2003/0229023, published Dec. 11, 2003; WO 03/057134, published Jul. 17, 2003; U.S. Pat. App. No. 2003/0236193, published Dec. 25, 2003 (corresponding to PCT/US04/010989, filed Apr. 8, 2004); U.S. Ser. No. 10/666,480, filed Sep. 18, 2003 (corresponding to WO 04/026329, published Apr. 1, 2004), each of which is hereby incorporated by reference in its entirety.

"Affibodies" or "Affibody" refers to the use of a protein liked by peptide bond to an Fc region, wherein the protein is used as a scaffold to provide a binding surface for a target molecule. The protein is often a naturally occurring protein such as staphylococcal protein A or IgG-binding B domain, or the Z protein derived therefrom (see Nilsson et al (1987), Prot Eng 1, 107-133, and U.S. Pat. No. 5,143,844) or a fragment or derivative thereof. For example, affibodies can be created from Z proteins variants having altered binding affinity to target molecule(s), wherein a segment of the Z protein has been mutated by random mutagenesis to create a library of variants capable of binding a target molecule. Examples of affibodies include U.S. Pat. No. 6,534,628, Nord K et al, Prot Eng 8:601-608 (1995) and Nord K et al, Nat Biotech 15:772-777 (1997). Biotechnol Appl Biochem. 2008 June; 50(Pt 2):97-112.

As used herein, the term "immunoadhesin" designates molecules which combine the binding specificity of a heterologous protein (an "adhesin") with the effector functions of immunoglobulin constant domains. Structurally, the immunoadhesins comprise a fusion of an amino acid sequence with a desired binding specificity, which amino acid sequence is other than the antigen recognition and binding site of an antibody (i.e., is "heterologous" compared to a constant region of an antibody), and an immunoglobulin constant domain sequence (e.g., $C_H2$ and/or $C_H3$ sequence of an IgG). Exemplary adhesin sequences include contiguous amino acid sequences that comprise a portion of a receptor or a ligand that binds to a protein of interest. Adhesin sequences can also be sequences that bind a protein of interest, but are not receptor or ligand sequences (e.g., adhesin sequences in peptibodies). Such polypeptide sequences can be selected or identified by various methods, include phage display techniques and high throughput sorting methods. The immunoglobulin constant domain sequence in the immunoadhesin can be obtained from any immunoglobulin, such as IgG1, IgG2, IgG3, or IgG4 subtypes, IgA (including IgA1 and IgA2), IgE, IgD, or IgM.

"Complex" or "complexed" as used herein refers to the association of two or more molecules that interact with each other through bonds and/or forces (e.g., van der waals, hydrophobic, hydrophilic forces) that are not peptide bonds. In one embodiment, the complex is heteromultimeric. It should be understood that the term "protein complex" or "polypeptide complex" as used herein includes complexes that have a non-protein entity conjugated to a protein in the protein complex (e.g., including, but not limited to, chemical molecules such as a toxin or a detection agent).

A heteromultimeric protein of this invention "which binds an antigen of interest is one that binds the target with sufficient affinity such that the heteromultimeric protein is useful as a diagnostic and/or therapeutic agent in targeting a protein or a cell or tissue expressing the target, and does not significantly cross-react with other proteins. In such embodiments, the extent of binding of the heteromultimeric protein to a "non-target" protein will be less than about 10% of the binding of the antibody to its particular target protein as determined by fluorescence activated cell sorting (FACS) analysis or radioimmunoprecipitation (RIA) or ELISA. With regard to the binding of a heteromultimeric protein to a target molecule, the term "specific binding" or "specifically binds to" or is "specific for" a particular polypeptide or an epitope on a particular polypeptide target means binding that is measurably different from a non-specific interaction (e.g., a non-specific interaction may be binding to bovine serum albumin or casein). Specific binding can be measured, for example, by determining binding of a molecule compared to binding of a control molecule. For example, specific binding can be determined by competition with a control molecule that is similar to the target, for example, an excess of non-labeled target. In this case, specific binding is indicated if the binding of the labeled target to a probe is competitively inhibited by excess unlabeled target. The term "specific binding" or "specifically binds to" or is "specific for" a particular polypeptide or an epitope on a particular polypeptide target as used herein can be exhibited, for example, by a molecule having a Kd for the target of at least about 200 nM, alternatively at least about 150 nM, alternatively at least about 100 nM, alternatively at least about 60 nM, alternatively at least about 50 nM, alternatively at least about 40 nM, alternatively at least about 30 nM, alternatively at least about 20 nM, alternatively at least about 10 nM, alternatively at least about 8 nM, alternatively at least about 6 nM, alternatively at least about 4 nM, alternatively at least about 2 nM, alternatively at least about 1 nM, or greater. In one embodiment, the term "specific binding" refers to binding where a heteromultimeric protein binds to a particular polypeptide or epitope on a particular polypeptide without substantially binding to any other polypeptide or polypeptide epitope.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). For example, the Kd can be about 200 nM, 150 nM, 100 nM, 60 nM, 50 nM, 40 nM, 30 nM, 20 nM, 10 nM, 8 nM, 6 nM, 4 nM, 2 nM, 1 nM, or stronger. Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention.

In one embodiment, the "Kd" or "Kd value according to this invention is measured by using surface plasmon resonance assays using a BIAcore™-2000 or a BIAcore™-3000 (BIAcore, Inc., Piscataway, N.J.) at 25° C. with immobilized target (e.g., antigen) CM5 chips at ~10 response units (RU). Briefly, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, into 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (e.g., 0.78 nM to 500 nM) are injected in PBS with 0.05% Tween 20 (PBST) at 25° C. at a flow rate of approximately 25 µl/min. Association rates ($k_{on}$) and dissociation rates ($k_{off}$) are calculated using a simple one-to-one Langmuir binding model (BIAcore Evaluation Software version 3.2) by simultaneous fitting the association and dissociation sensorgram. The equilibrium dissociation constant (Kd) is calculated as the ratio $k_{off}/k_{on}$. See, e.g., Chen et al., J. Mol. Biol. 293:865-881 (1999). If the on-rate exceeds $10^6$ $M^{-1}$ the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-Aminco spectrophotometer (ThermoSpectronic) with a stirred cuvette.

"Biologically active" and "biological activity" and "biological characteristics" with respect to a heteromultimeric protein of this invention, such as an antibody, fragment, or derivative thereof, means having the ability to bind to a biological molecule, except where specified otherwise.

"Isolated," when used to describe the various heteromultimer polypeptides means a heteromultimer which has been separated and/or recovered from a cell or cell culture from which it was expressed. Contaminant components of its natural environment are materials which would interfere with diagnostic or therapeutic uses for the heteromultimer, and may include enzymes, hormones, and other proteinaceous or nonproteinaceous solutes. In certain embodiments, the heteromultimer will be purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Ordinarily, however, isolated polypeptide will be prepared by at least one purification step.

The heteromultimers of the present invention are generally purified to substantial homogeneity. The phrases "substantially homogeneous", "substantially homogeneous form" and "substantial homogeneity" are used to indicate that the product is substantially devoid of by-products originated from undesired polypeptide combinations (e.g., homomultimers).

Expressed in terms of purity, substantial homogeneity means that the amount of by-products does not exceed 10%, 9%, 8%, 7%, 6%, 4%, 3%, 2% or 1% by weight or is less than 1% by weight. In one embodiment, the by-product is below 5%.

"Biological molecule" refers to a nucleic acid, a protein, a carbohydrate, a lipid, and combinations thereof. In one embodiment, the biologic molecule exists in nature.

By "linked" or "links as used herein is meant either a direct peptide bond linkage between a first and second amino acid sequence or a linkage that involves a third amino acid sequence that is peptide bonded to and between the first and second amino acid sequences. For example, a linker peptide bonded to the C-terminal end of one amino acid sequence and to the N-terminal end of the other amino acid sequence.

By "linker" as used herein is meant an amino acid sequence of two or more amino acids in length. The linker can consist of neutral polar or nonpolar amino acids. A linker can be, for example, 2 to 100 amino acids in length, such as between 2 and 50 amino acids in length, for example, 3, 5, 10, 15, 20, 25, 30, 35, 40, 45, or 50 amino acids in length. A linker can be "cleavable," for example, by auto-cleavage, or enzymatic or chemical cleavage. Cleavage sites in amino acid sequences and enzymes and chemicals that cleave at such sites are well known in the art and are also described herein.

By a "tether" as used herein is meant an amino acid linker that joins two other amino acid sequences. A tether as described herein can link the N-terminus of an immunoglobulin heavy chain variable domain with the C-terminus of an immunoglobulin light chain constant domain. In particular embodiments, a tether is between about 15 and 50 amino acids in length, for example, between 20 and 26 amino acids in length (e.g., 20, 21, 22, 23, 24, 25, or 26 amino acids in length). A tether may be "cleavable," for example, by auto-cleavage, or enzymatic or chemical cleavage using methods and reagents standard in the art.

Enzymatic cleavage of a "linker" or a "tether" may involve the use of an endopeptidase such as, for example, Lys-C, Asp-N, Arg-C, V8, Glu-C, chymotrypsin, trypsin, pepsin, papain, thrombin, Genenase, Factor Xa, TEV (tobacco etch virus cysteine protease), Enterokinase, HRV C3 (human rhinovirus C3 protease), Kininogenase, as well as subtilisin-like proprotein convertases (e.g., Furin (PC1), PC2, or PC3) or N-arginine dibasic convertase. Chemical cleavage may involve use of, for example, hydroxylamine, N-chlorosuccinimide, N-bromosuccinimide, or cyanogen bromide.

A "Lys-C endopeptidase cleavage site" as used herein is a Lysine residue in an amino acid sequence that can be cleaved at the C-terminal side by Lys-C endopeptidase. Lys-C endopeptidase cleaves at the C-terminal side of a Lysine residue.

By a "chaotropic agent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects). Exemplary chaotropic agents include, but are not limited to, urea, Guanidine-HCl, lithium perchlorate, Histidine, and Arginine.

By a "mild detergent" is meant a water-soluble substance which disrupts the three-dimensional structure of a protein (e.g., an antibody) by interfering with stabilizing intra-molecular interactions (e.g., hydrogen bonds, van der Waals forces, or hydrophobic effects), but which does not permanently disrupt the protein structure as to cause a loss of biological activity (i.e., does not denature the protein). Exemplary mild detergents include, but are not limited to, Tween (e.g., Tween-20), Triton (e.g., Triton X-100), NP-40 (nonyl phenoxylpolyethoxylethanol), Nonidet P-40 (octyl phenoxylpolyethoxylethanol), and Sodium Dodecyl Sulfate (SDS).

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptor); and B cell activation.

"Antibody-dependent cell-mediated cytotoxicity" or "ADCC refers to a form of cytotoxicity in which secreted Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxic agents. The antibodies "arm" the cytotoxic cells and are absolutely required for such killing. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, Annu. Rev. Immunol. 9:457-92 (1991). To assess ADCC activity of a molecule of interest, an in vitro ADCC assay, such as that described in U.S. Pat. No. 5,500,362 or U.S. Pat. No. 5,821,337 can be performed. Useful effector cells for such assays include peripheral blood mononuclear cells (PBMC) and Natural Killer (NK) cells. Alternatively, or additionally, ADCC activity of the molecule of interest can be assessed in vivo, e.g., in a animal model such as that disclosed in Clynes et al., Proc. Natl. Acad. Sci. USA 95:652-656 (1998).

"Fc receptor" or "FcR" describes a receptor that binds to the Fc region of an antibody. The preferred FcR is a human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. Daëron, Annu. Rev. Immunol. 15:203-234 (1997)). FcRs are reviewed in Ravetch and Kinet, Annu. Rev. Immunol. 9:457-492 (1991); Capel et al., Immunomethods 4:25-34 (1994); and de Haas et al., J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., J. Immunol. 117:587 (1976) and Kim et al., J. Immunol. 24:249 (1994)).

"Human effector cells" are leukocytes that express one or more FcRs and perform effector functions. Preferably, the cells express at least FcγRIII and perform ADCC effector function. Examples of human leukocytes that mediate ADCC include peripheral blood mononuclear cells (PBMC), natural killer (NK) cells, monocytes, cytotoxic T cells, and neutrophils; with PBMCs and NK cells being preferred. The effector cells can be isolated from a native source, e.g., from blood.

"Complement dependent cytotoxicity" or "CDC refers to the lysis of a target cell in the presence of complement. Activation of the classical complement pathway is initiated by the binding of the first component of the complement system (C1q) to antibodies (of the appropriate subclass) that are bound to their cognate antigen. To assess complement activation, a CDC assay, e.g., as described in Gazzano-Santoro et al., J. Immunol. Methods 202:163 (1996), can be performed.

The term "therapeutically effective amount" refers to an amount of an antibody, antibody fragment, or derivative to treat a disease or disorder in a subject. In the case of tumor (e.g., a cancerous tumor), the therapeutically effective amount of the antibody or antibody fragment (e.g., a multispecific antibody or antibody fragment) may reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the antibody or antibody fragment may prevent growth and/or kill existing cancer cells, it may be cytostatic and/or cytotoxic. For cancer therapy, efficacy in vivo can, for example, be measured by assessing the duration of survival, time to disease progression (TTP), the response rates (RR), duration of response, and/or quality of life.

By "reduce or inhibit" is meant the ability to cause an overall decrease preferably of 20% or greater, more preferably of 50% or greater, and most preferably of 75%, 85%, 90%, 95%, or greater. Reduce or inhibit can refer to the symptoms of the disorder being treated, the presence or size of metastases, the size of the primary tumor, or the size or number of the blood vessels in angiogenic disorders.

The terms "cancer" and "cancerous" refer to or describe the physiological condition in mammals that is typically characterized by unregulated cell growth/proliferation. Included in this definition are benign and malignant cancers. Examples of cancer include but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastric or stomach cancer including gastrointestinal cancer, pancreatic cancer, glioblastoma, glioma, cervical cancer, ovarian cancer, liver cancer, bladder cancer, hepatoma, breast cancer, colon cancer, colorectal cancer, endometrial or uterine carcinoma, salivary gland carcinoma, kidney cancer (e.g., renal cell carcinoma), liver cancer, prostate cancer, vulval cancer, thyroid cancer, hepatic carcinoma, anal carcinoma, penile carcinoma, melanoma, and various types of head and neck cancer. By "early stage cancer" is meant a cancer that is not invasive or metastatic or is classified as a Stage 0, I, or II cancer. The term "precancerous" refers to a condition or a growth that typically precedes or develops into a cancer. By "non-metastatic" is meant a cancer that is benign or that remains at the primary site and has not penetrated into the lymphatic or blood vessel system or to tissues other than the primary site. Generally, a non-metastatic cancer is any cancer that is a Stage 0, I, or II cancer, and occasionally a Stage III cancer.

An "allergic or inflammatory disorder" herein is a disease or disorder that results from a hyper-activation of the immune system of an individual. Exemplary allergic or inflammatory disorders include, but are not limited to, asthma, psoriasis, rheumatoid arthritis, atopic dermatitis, multiple sclerosis, systemic lupus, erythematosus, eczema, organ transplantation, age-related macular degeneration, Crohn's disease, ulcerative colitis, eosinophilic esophagitis, and autoimmune diseases associated with inflammation.

An "autoimmune disease" herein is a disease or disorder arising from and directed against an individual's own tissues or a co-segregate or manifestation thereof or resulting condition therefrom. Examples of autoimmune diseases or disorders include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brain-stem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia greata, CREST syndrome (calcinosis, Raynaud's phenomenon, esophageal dysmotility, sclerodactyl), and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, *ascariasis*, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antibodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

The term "cytotoxic agent" as used herein refers to a substance that inhibits or prevents the function of a cell and/or causes destruction of a cell. The term is intended to include radioactive isotopes (e.g., $At^{211}$, $I^{131}$, $I_{125}$, $Y^{90}$, $Re^{186}$, $Re^{188}$, $Sm^{153}$, $Bi^{212}$, $Ra^{223}$, $P^{32}$, and radioactive isotopes of Lu), chemotherapeutic agents, e.g., methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor, anticancer, and chemotherapeutic agents disclosed herein. Other cytotoxic agents are described herein. A tumoricidal agent causes destruction of tumor cells.

"chemotherapeutic agent" is a chemical compound useful in the treatment of cancer. Examples of chemotherapeutic agents include alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma 1 (see, e.g., Agnew, Chem. Intl. Ed. Engl. 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholine-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2', 2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell either in vitro or in vivo. Thus, the growth inhibitory agent may be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (e.g., vincristine and vinblastine), taxanes, and topoisomerase II inhibitors such as doxorubicin, epirubicin, daunorubicin, etoposide, and bleomycin. The agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Anti-cancer therapy" as used herein refers to a treatment that reduces or inhibits cancer in a subject. Examples of anti-cancer therapy include cytotoxic radiotherapy as well as the administration of a therapeutically effective amount of a cytotoxic agent, a chemotherapeutic agent, a growth inhibitory agent, a cancer vaccine, an angiogenesis inhibitor, a prodrug, a cytokine, a cytokine antagonist, a corticosteroid, an immunosuppressive agent, an anti-emetic, an antibody or antibody fragment, or an analgesic to the subject.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). Prodrugs include, but are not limited to, phosphate-containing prodrugs, thiophosphate-containing prodrugs, sulfate-containing prodrugs, peptide-containing prodrugs, D-amino acid-modified prodrugs, glycosylated prodrugs, beta-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone (HGH), N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); epidermal growth factor (EGF); hepatic growth factor; fibroblast growth factor (FGF); prolactin; placental lactogen; tumor necrosis factor-alpha and -beta; mullerian-inhibiting substance; mouse gonadotropin-associated peptide; inhibin; activin; vascular endothelial growth factor; integrin; thrombopoietin (TPO); nerve growth factors such as NGF-alpha; platelet-growth factor; transforming growth factors (TGFs) such as TGF-alpha and TGF-beta; insulin-like growth factor-I and -II; erythropoietin (EPO); osteoinductive factors; interferons such as interferon-alpha, -beta and -gamma colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1 alpha, IL-1beta, IL-2, IL-3, IL-4, IL-5, IL-6, IL-7, IL-8, IL-9, IL-10, IL-11, IL-12; IL-18a tumor necrosis factor such as TNF-alpha or TNF-beta; and other polypeptide factors including LIF and kit ligand (KL). As used herein, the term cytokine includes proteins from natural sources or from recombinant cell culture and biologically active equivalents of the native sequence cytokines.

By "cytokine antagonist" is meant a molecule that partially or fully blocks, inhibits, or neutralizes a biological activity of at least one cytokine. For example, the cytokine antagonists may inhibit cytokine activity by inhibiting cytokine expression and/or secretion, or by binding to a cytokine or to a cytokine receptor. Cytokine antagonists include antibodies, synthetic or native-sequence peptides, immunoadhesins, and small-molecule antagonists that bind to a cytokine or cytokine receptor. The cytokine antagonist is optionally conjugated with or fused to a cytotoxic agent. Exemplary TNF antagonists are etanercept (ENBREL®), infliximab (REMICADE®), and adalimumab (HUMIRA™).

The term "immunosuppressive agent" as used herein refers to substances that act to suppress or mask the immune system of the subject being treated. This includes substances that suppress cytokine production, downregulate or suppress self-antigen expression, or mask the MHC antigens. Examples of immunosuppressive agents include 2-amino-6-aryl-5-substituted pyrimidines (see U.S. Pat. No. 4,665,077); mycophenolate mofetil such as CELLCEPT®; azathioprine (IMURAN®, AZASAN®/6-mercaptopurine; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids and glucocorticosteroids, e.g., prednisone, prednisolone such as PEDIAPRED® (prednisolone sodium phosphate) or ORAPRED® (prednisolone sodium phosphate oral solution), methylprednisolone, and dexamethasone; methotrexate (oral or subcutaneous) (RHEUMATREX®, TREXALL™); hydroxycloroquine/chloroquine; sulfasalazine; leflunomide; cytokine or cytokine receptor antagonists including anti-interferon-γ, -β, or -α antibodies, anti-tumor necrosis factor-α antibodies (infliximab or adalimumab), anti-TNFα immunoadhesin (ENBREL®, etanercept), anti-tumor necrosis factor-β antibodies, anti-interleukin-2 antibodies and anti-IL-2 receptor antibodies; anti-LFA-1 antibodies, including anti-CD11a and anti-CD18 antibodies; anti-L3T4 antibodies; heterologous anti-lymphocyte globulin; polyclonal or pan-T antibodies, or monoclonal anti-CD3 or anti-CD4/CD4a antibodies; soluble peptide containing a LFA-3 binding domain (WO 90/08187); streptokinase; TGF-β; streptodornase; RNA or DNA from the host; FK506; RS-61443; deoxyspergualin; rapamycin; T-cell receptor (Cohen et al., U.S. Pat. No. 5,114,721); T-cell receptor fragments (Offner et al. Science 251: 430-432 (1991); WO 90/11294; laneway, Nature 341:482 (1989); and WO 91/01133); T cell receptor antibodies (EP 340,109) such as T10B9; cyclophosphamide (CYTOXAN®); dapsone; penicillamine (CUPRIMINE®); plasma exchange; or intravenous immunoglobulin (IVIG). These may be used alone or in combination with each other, particularly combinations of steroid and another immunosuppressive agent or such combinations followed by a maintenance dose with a non-steroid agent to reduce the need for steroids.

An "analgesic" refers to a drug that acts to inhibit or suppress pain in a subject. Exemplary analgesics include non-steroidal anti-inflammatory drugs (NSAIDs) including ibuprofen (MOTRIN®), naproxen (NAPROSYN®), acetylsalicylic acid, indomethacin, sulindac, and tolmetin, including salts and derivatives thereof, as well as various other medications used to reduce the stabbing pains that may occur, including anticonvulsants (gabapentin, phenyloin, carbamazepine) or tricyclic antidepressants. Specific examples include acetaminophen, aspirin, amitriptyline (ELAVIL®), carbamazepine (TEGRETOL®), phenyltoin (DILANTIN®), gabapentin (NEURONTIN®), (E)-N-Vanillyl-8-methyl-6-noneamid (CAPSAICIN®), or a nerve blocker.

"Corticosteroid" refers to any one of several synthetic or naturally occurring substances with the general chemical structure of steroids that mimic or augment the effects of the naturally occurring corticosteroids. Examples of synthetic corticosteroids include prednisone, prednisolone (including methylprednisolone), dexamethasone triamcinolone, and betamethasone.

A "cancer vaccine," as used herein is a composition that stimulates an immune response in a subject against a cancer. Cancer vaccines typically consist of a source of cancer-associated material or cells (antigen) that may be autologous (from self) or allogenic (from others) to the subject, along with other components (e.g., adjuvants) to further stimulate and boost the immune response against the antigen. Cancer vaccines can result in stimulating the immune system of the subject to produce antibodies to one or several specific antigens, and/or to produce killer T cells to attack cancer cells that have those antigens.

"Cytotoxic radiotherapy" as used herein refers to radiation therapy that inhibits or prevents the function of cells and/or causes destruction of cells. Radiation therapy may include, for example, external beam irradiation or therapy with a radioactive labeled agent, such as an antibody. The term is intended to include use of radioactive isotopes (e.g., $At^{211}$, $I^{131}$, $I^{125}$, $Y^{90}$, $Re^{186}$, $Re^{188}$, $Sm^{153}$, $Bi^{212}$, $Ra^{223}$, $P^{32}$, and radioactive isotopes of Lu).

A "subject" is a vertebrate, such as a mammal, e.g., a human. Mammals include, but are not limited to, farm animals (such as cows), sport animals, pets (such as cats, dogs and horses), primates, mice, and rats.

Except where indicated otherwise by context, the terms "first" polypeptide and "second" polypeptide, and variations thereof, are merely generic identifiers, and are not to be taken as identifying a specific or a particular polypeptide or component of antibodies of the invention.

Commercially available reagents referred to in the Examples were used according to manufacturer's instructions unless otherwise indicated. The source of those cells identified in the following Examples, and throughout the specification, by ATCC accession numbers is the American Type Culture Collection, Manassas, Va. Unless otherwise noted, the present invention uses standard procedures of recombinant DNA technology, such as those described hereinabove and in the following textbooks: Sambrook et al., supra; Ausubel et al., Current Protocols in Molecular Biology (Green Publishing Associates and Wiley Interscience, NY, 1989); Innis et al., PCR Protocols: A Guide to Methods and Applications (Academic Press, Inc., NY, 1990); Harlow et al., Antibodies: A Laboratory Manual (Cold Spring Harbor Press, Cold Spring Harbor, 1988); Gait, Oligonucleotide Synthesis (IRL Press, Oxford, 1984); Freshney, Animal Cell Culture, 1987; Coligan et al., Current Protocols in Immunology, 1991.

Throughout this specification and claims, the word "comprise," or variations such as "comprises" or "comprising," will be understood to imply the inclusion of a stated integer or group of integers but not the exclusion of any other integer or group of integers.

II. CONSTRUCTION OF HETEROMULTIMERIC PROTEINS

Typically, the heteromultimeric proteins described herein will comprise a significant portion of an antibody Fc region. In other aspects, however, the heavy chain comprises only a portion of the $C_H1$, $C_H2$, and/or $C_H3$ domains.

Heteromultimerization Domains

The heteromultimeric proteins comprise a heteromultimerization domain. To generate a substantially homogeneous population of heterodimeric molecule, the heterodimerization domain must have a strong preference for forming heterodimers over homodimers. Although the heteromultimeric proteins exemplified herein use the knobs into holes technology to facilitate heteromultimerization those skilled in the art will appreciate other heteromultimerization domains useful in the instant invention.

Knobs into Holes

The use of knobs into holes as a method of producing multispecific antibodies is well known in the art. See U.S. Pat. No. 5,731,168 granted 24 Mar. 1998 assigned to Genentech, PCT Pub. No. WO2009089004 published 16 Jul. 2009 and assigned to Amgen, and US Pat. Pub. No. 20090182127 published 16 Jul. 2009 and assigned to Novo Nordisk A/S. See also Marvin and Zhu, Acta Pharmacologica Sincia (2005) 26(6):649-658 and Kontermann (2005) Acta Pharacol. Sin., 26:1-9. A brief discussion is provided here.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). Normally, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The upper limit for the number of original residues which are replaced is the total number of residues in the interface of the first polypeptide. The side chain volumes of the various amino residues are shown in the following table.

TABLE 1

Properties of Amino Acid Residues

| Amino Acid | One-Letter Abbreviation | MASS[a] (daltons) | VOLUME[b] (Angstrom$^3$) | Accessible Surface Area[c] (Angstrom$^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalinine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight amino acid minus that of water. Values from *Handbook of Chemistry and Physics*, 43rd ed. Cleveland, Chemical Rubber Publishing Co., 1961.
[b]Values from A. A. Zamyatnin, *Prog. Biophys. Mol. Biol.* 24: 107-123, 1972.
[c]Values from C. Chothia, *J. Mol. Biol.* 105: 1-14, 1975. The accessible surface area is defined in FIG. 6-20 of this reference.

The preferred import residues for the formation of a protuberance are generally naturally occurring amino acid residues and are preferably selected from arginine (R), phenylalanine (F), tyrosine (Y) and tryptophan (W). Most preferred are tryptophan and tyrosine. In one embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). Normally, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. The upper limit for the number of original residues which are replaced is the total number of residues in the interface of the second polypeptide. The side chain volumes of the various amino residues are shown in Table 1 above. The preferred import residues for the formation of a cavity are usually naturally occurring amino acid residues and are preferably selected from alanine (A), serine (S), threonine (T) and valine (V). Most preferred are serine, alanine or threonine. In one embodiment, the original residue for the formation of the cavity has a large side chain volume, such as tyrosine, arginine, phenylalanine or tryptophan.

An "original" amino acid residue is one which is replaced by an "import" residue which can have a smaller or larger side chain volume than the original residue. The import amino acid residue can be a naturally occurring or non-naturally occurring amino acid residue, but preferably is the former. "Naturally occurring" amino acid residues are those residues encoded by the genetic code and listed in Table 1 above. By "non-naturally occurring" amino acid residue is meant a residue which is not encoded by the genetic code, but which is able to covalently bind adjacent amino acid residue(s) in the polypeptide chain. Examples of non-naturally occurring amino acid residues are norleucine, ornithine, norvaline, homoserine and other amino acid residue analogues such as those described in Ellman et al., *Meth. Enzym.* 202:301-336 (1991), for example. To generate such non-naturally occurring amino acid residues, the procedures of Noren et al. *Science* 244: 182 (1989) and Ellman et al., supra can be used. Briefly, this involves chemically activating a suppressor tRNA with a non-naturally occurring amino acid residue followed by in vitro transcription and translation of the RNA. The method of the instant invention involves replacing at least one original amino acid residue, but more than one original residue can be replaced. Normally, no more than the total residues in the interface of the first or second polypeptide will comprise original amino acid residues which are replaced. Typically, original residues for replacement are "buried". By "buried" is meant that the residue is essentially inaccessible to solvent. Generally, the import residue is not cysteine to prevent possible oxidation or mispairing of disulfide bonds.

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity relies on modeling the protuberance/cavity pair based upon a three-dimensional structure such as that obtained by X-ray crystallography or nuclear magnetic resonance (NMR). This can be achieved using widely accepted techniques in the art.

By "original or template nucleic acid" is meant the nucleic acid encoding a polypeptide of interest which can be "altered" (La genetically engineered or mutated) to encode a protuberance or cavity. The original or starting nucleic acid may be a naturally occurring nucleic acid or may comprise a nucleic acid which has been subjected to prior alteration (e.g. a humanized antibody fragment). By "altering" the nucleic acid is meant that the original nucleic acid is mutated by inserting, deleting or replacing at least one codon encoding an amino acid residue of interest. Normally, a codon encoding an original residue is replaced by a codon encoding an import residue. Techniques for genetically modifying a DNA in this manner have been reviewed in *Mutagenesis: a Practical Approach*, M. J. McPherson, Ed., (IRL Press, Oxford, UK. (1991), and include site-directed mutagenesis, cassette mutagenesis and polymerase chain reaction (PCR) mutagenesis, for example. By mutating an original/template nucleic acid, an original/template polypeptide encoded by the original/template nucleic acid is thus correspondingly altered.

The protuberance or cavity can be "introduced" into the interface of a first or second polypeptide by synthetic means, e.g. by recombinant techniques, in vitro peptide synthesis, those techniques for introducing non-naturally occurring amino acid residues previously described, by enzymatic or chemical coupling of peptides or some combination of these techniques. Accordingly, the protuberance or cavity which is "introduced" is "non-naturally occurring" or "non-native", which means that it does not exist in nature or in the original polypeptide (e.g. a humanized monoclonal antibody).

Generally, the import amino acid residue for forming the protuberance has a relatively small number of "rotomers" (e.g. about 3-6). A "rotomer" is an energetically favorable conformation of an amino acid side chain. The number of rotomers of the various amino acid residues are reviewed in Ponders and Richards, *J. Mol. Biol.* 193: 775-791 (1987).

III. VECTORS, HOST CELLS AND RECOMBINANT METHODS

For recombinant production of a heteromultimeric protein (e.g., an antibody) of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian, but also including fungi (e.g., yeast), insect, plant, and nucleated cells from other multicellular organisms) origin. It will be appreciated that constant regions of any isotype can be used for this purpose, including IgG, IgM, IgA, IgD, and IgE constant regions, and that such constant regions can be obtained from any human or animal species.

a. Generating Heteromultimeric Proteins Using Prokaryotic Host Cells i. Vector Construction Polynucleotide sequences encoding polypeptide components of the heteromultimeric proteins (e.g., an antibody) of the invention can be obtained using standard recombinant techniques. Desired polynucleotide sequences may be isolated and sequenced from, for example, antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM™-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. An inducible promoter is a promoter that initiates increased levels of transcription of the cistron under its control in response to changes in the culture condition, e.g., the presence or absence of a nutrient or a change in temperature.

A large number of promoters recognized by a variety of potential host cells are well known. The selected promoter can be operably linked to cistron DNA encoding, for example, the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of the expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker to operably ligate them to cistrons encoding the genes of the heteromultimeric protein, e.g., the target light and heavy chains (Siebenlist et al., (1980) Cell 20: 269), using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e., cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the *E. coli* trxff strains) provide cytoplasm conditions that are favorable for disulfide bond formation, thereby permitting proper folding and assembly of expressed protein subunits. See Proba and Pluckthun *Gene*, 159:203 (1995).

Prokaryotic host cells suitable for expressing heteromultimeric proteins (e.g., antibodies) of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla,* or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (Δton) ptr3 lac Iq lacL8 ΔompTΔ(nmpc-fepE) degP41 kan$^R$ (U.S. Pat. No. 5,639,635). Other strains and derivatives thereof, such as *E. coli* 294 (ATCC 31,446), *E. coli* B, *E. coli*$_\lambda$ 1776 (ATCC 31,537) and *E. coli* RV308 (ATCC 31,608) are also suitable. In one embodiment, *E. coli* Δlpp finds particular use. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli, Serratia,* or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

ii. Polypeptide Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include Luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the first and second hinge-containing host cells are cultured separately and the expressed polypeptides of the present invention are secreted into and recovered from the periplasm of the host cells separately. In a second embodiment, the first and second hinge-containing host cells are cultured separately and prior to the isolation of the hinge-containing polypeptides, the two host cell cultures are mixed together and the cells pelleted. In a third embodiment, the first and second hinge-containing host cells are cultured separately, centrifuged and resuspended separately and then mixed together prior to isolation of the hinge-containing polypeptides. In fourth embodiment, the first and second hinge-containing host cells are cultured together in the same culture vessel. Protein recovery typically involves disrupting the microorganism cell membrane, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay. The isolated polypeptides will be used to produce the heteromultimeric proteins at In one aspect of the invention, heteromultimeric protein (e.g., antibody) production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted heteromultimeric proteins (e.g., antibodies), additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), *Proc. Natl. Acad. Sci. USA* 95:2773-2777; Georgiou et al., U.S. Pat. No. 5,264,365; Georgiou et al., U.S. Pat. No. 5,508,192; Nara et al., *Microbial Drug Resistance,* 2:63-72 (1996).

In one embodiment, *E. coli* strains deficient for proteolytic enzymes and transformed with plasmids overexpressing one or more chaperone proteins are used as host cells in the expression system of the invention. In a second embodiment, the *E. coli* strain is deficient for a lipoprotein of the outer membrane (Δlpp).

iii. Heteromultimeric Protein Purification

In one embodiment, the heteromultimeric protein produced herein is further purified to obtain preparations that are substantially homogeneous for further assays and uses. Standard protein purification methods known in the art can be employed.

The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of, for example, full length antibody products of the invention. Protein A is a 41 kD cell wall protein from *Staphylococcus aureus* which binds with a high affinity to the Fc region of antibodies. Lindmark et al. (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. The heteromultimeric protein (e.g., antibody) is recovered from the solid phase by elution.

b. Generating Heteromultimeric Proteins Using Eukaryotic Host Cells:

The vector components generally include, but are not limited to, one or more of the following: a signal sequence, an origin of replication, one or more marker genes, an enhancer element, a promoter, and a transcription termination sequence.

i. Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available. The DNA for such precursor region is ligated in reading frame to DNA encoding the desired heteromultimeric protein(s) (e.g., antibodies).

ii. Origin of Replication

Generally, an origin of replication component is not needed for mammalian expression vectors. For example, the SV40 origin may typically be used, but only because it contains the early promoter.

iii. Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See, for example, U.S. Pat. No. 4,965,199.

iv. Promoter Component

Expression and cloning vectors usually contain a promoter that is recognized by the host organism and is operably linked to the desired hinge-containing polypeptide(s) (e.g., antibody) nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Desired hinge-containing polypeptide(s) (e.g., antibody) transcription from vectors in mammalian host cells is controlled, for example, by promoters obtained from the genomes of viruses such as, for example, polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

v. Enhancer Element Component

Transcription of DNA encoding the desired hinge-containing polypeptide(s) (e.g., antibody) by higher eukaryotes can be increased by inserting an enhancer sequence into the vector. Many enhancer sequences are now known from mammalian genes (e.g., globin, elastase, albumin, α-fetoprotein, and insulin genes). Also, one may use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) for a description of elements for enhancing activation of eukaryotic promoters. The enhancer may be spliced into the vector at a position 5' or 3' to the antibody polypeptide-encoding sequence, provided that enhancement is achieved, but is generally located at a site 5' from the promoter.

vi. Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

vii. Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for desired hinge-containing polypeptide(s) (e.g., antibody) production and cultured in conventional nutrient media modified as appropriate for inducing promoters, selecting transformants, or amplifying the genes encoding the desired sequences.

viii. Culturing the Host Cells

The host cells used to produce a desired hinge-containing polypeptide(s) (e.g., antibody) of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

ix. Purification of Heteromultimeric Proteins

When using recombinant techniques, the hinge-containing polypeptides can be produced intracellularly, or directly secreted into the medium. If the hinge-containing polypeptide is produced intracellularly, as a first step, the particulate debris, either host cells or lysed fragments, are removed, for example, by centrifugation or ultrafiltration. Where the hinge-containing polypeptide is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The heteromultimer composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25 M salt). The production of the heteromultimeric proteins can alternatively or additionally (to any of the foregoing particular methods) comprise dialyzing a solution comprising a mixture of the polypeptides.

x. Antibody Production Using Baculovirus

Recombinant baculovirus may be generated by co-transfecting a plasmid encoding an antibody or antibody fragment and BaculoGold™ virus DNA (Pharmingen) into an insect cell such as a *Spodoptera frugiperda* cell (e.g., Sf9 cells; ATCC CRL 1711) or a *Drosophila melanogaster* S2 cell using, for example, lipofectin (commercially available from GIBCO-BRL). In a particular example, an antibody sequence is fused upstream of an epitope tag contained within a baculovirus expression vector. Such epitope tags include poly-His tags. A variety of plasmids may be employed, including plasmids derived from commercially available plasmids such as pVL1393 (Novagen) or pAcGP67B (Pharmingen). Briefly, the sequence encoding an antibody or a fragment thereof may be amplified by PCR with primers complementary to the 5' and 3' regions. The 5' primer may incorporate flanking (selected) restriction enzyme sites. The product may then be digested with the selected restriction enzymes and subcloned into the expression vector.

After transfection with the expression vector, the host cells (e.g., Sf9 cells) are incubated for 4-5 days at 28° C. and the released virus is harvested and used for further amplifications. Viral infection and protein expression may be performed as described, for example, by O'Reilley et al. (Baculovirus expression vectors: A Laboratory Manual. Oxford: Oxford University Press (1994)).

Expressed poly-His tagged antibody can then be purified, for example, by Ni2+-chelate affinity chromatography as follows. Extracts can be prepared from recombinant virus-infected Sf9 cells as described by Rupert et al. (Nature 362:175-179 (1993)). Briefly, Sf9 cells are washed, resuspended in sonication buffer (25 mL HEPES pH 7.9; 12.5 mM $MgCl_2$; 0.1 mM EDTA; 10% glycerol; 0.1% NP-40; 0.4 M KCl), and sonicated twice for 20 seconds on ice. The sonicates are cleared by centrifugation, and the supernatant is diluted 50-fold in loading buffer (50 mM phosphate; 300 mM NaCl; 10% glycerol pH 7.8) and filtered through a 0.45 μm filter. A Ni2+-NTA agarose column (commercially available from Qiagen) is prepared with a bed volume of 5 mL, washed with 25 mL of water, and equilibrated with 25 mL of loading buffer. The filtered cell extract is loaded onto the column at 0.5 mL per minute. The column is washed to baseline A280 with loading buffer, at which point fraction collection is started. Next, the column is washed with a secondary wash buffer (50 mM phosphate; 300 mM NaCl; 10% glycerol pH 6.0), which elutes nonspecifically bound protein. After reaching A280 baseline again, the column is developed with a 0 to 500 mM Imidazole gradient in the secondary wash buffer. One mL fractions are collected and analyzed by SDS-PAGE and silver staining or Western blot with Ni2+-NTA-conjugated to alkaline phosphatase (Qiagen). Fractions containing the eluted His10-tagged antibody are pooled and dialyzed against loading buffer.

Alternatively, purification of the antibody can be performed using known chromatography techniques, including for instance, Protein A or protein G column chromatography. In one embodiment, the antibody of interest may be recovered from the solid phase of the column by elution into a solution containing a chaotropic agent or mild detergent. Exemplary chaotropic agents and mild detergents include, but are not limited to, Guanidine-HCl, urea, lithium perclorate, Arginine, Histidine, SDS (sodium dodecyl sulfate), Tween, Triton, and NP-40, all of which are commercially available.

IV. HETEROMULTIMERIC PROTEIN FORMATION/ASSEMBLY

The formation of the complete heteromultimeric protein involves the reassembly of the first and second hinge-containing polypeptides by disulfide bond formation which in the present invention is referred to as refolding. Refolding includes the association of the first hinge-containing polypeptide with the second hinge-containing polypeptide and the formation of the interchain disulfide bonds. Refolding, also termed renaturating, in the present invention is done in vitro without the addition of reductant.

The host cells may be cultured using the above described methods either as separate cultures or as a single culture. In one method, the first host cells and second host cells are grown in the same culture vessel (sometimes referred to herein as co-cultured or a mixed culture). In another method, the first and second host cells are grown in separate culture vessels. In one method, the separate cultures are processed separately then mixed/combined prior to disruption of the cellular membrane. In another method, the separate cultures are mixed then processed prior to disruption of the cellular membrane. In one method, the separate cultures are mixed without further processing prior to disruption of the cellular membrane. In one method, the single culture comprising the first and second host cells is processed prior to disruption of the cellular membrane. In another method, the co-cultured cells are not processed prior to disruption of the cellular membrane. Processing of the cells comprises centrifugation and resuspension in an appropriate buffer (e.g., extraction buffer).

Extraction buffers are known in the art and the skilled artisan will be able to determine which buffer to use without undue experimentation.

The host cell membranes are disrupted using methods known in the art. Such methods include cell membrane permeablization and cell membrane disintegration. Permeablizing the cell membrane refers to rendering the membrane "leaky", e.g., by introducing holes, without destroying the overall integrity of the membrane such that the cell remains viable. In other words, permeabilization provides macromolecular movement across the cellular membrane and preserves cellular structure sufficiently to allow continued cell viability. In contrast, cell membrane disintegration results in the cellular contents being released into the extracellular milieu and cell death.

Methods for disrupting cell membranes include but are not limited to enzymatic lysis. sonication, osmotic shock, passage through a microfluidizer, addition of EDTA, use various detergents, solvents (such as toluene, dimethyl sulfoxide, etc), surfactants (such as Triton-X 100, Tween 20, etc), hypotonic buffers, use of freeze/thaw techniques, electroporation, and passage through a stainless steel ball homogenizer.

Once the hinge-containing polypeptides are released from the cell (either by permeabilization or disintegration) the heteromultimerization domains will drive the association of the heteromultimeric proteins. Inter-chain disulfide formation of the associated hinge-containing polypeptides proceeds without the addition of reducing agents. The resultant disulfide linked heteromultimeric protein is then purified. Optionally, it may be formulated for research, diagnostic, therapeutic or other purposes.

V. TARGET MOLECULES

Examples of molecules that may be targeted by a heteromultimeric protein of this invention include, but are not limited to, soluble serum proteins and their receptors and other membrane bound proteins (e.g., adhesins).

In another embodiment the heteromultimeric protein of the invention is capable of binding one, two or more cytokines, cytokine-related proteins, and cytokine receptors selected from the group consisting of BMPI, BMP2, BMP3B (GDFIO), BMP4, BMP6, BMP8, CSFI (M-CSF), CSF2 (GM-CSF), CSF3 (G-CSF), EPO, FGFI (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNAI, IFNA2, IFNA4, IFNA5, IFNA6, IFNA7, IFNBI, IFNG, IFNWI, FELI, FELI (EPSELON), FELI (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSFI0 (TRAIL), TNFSF11 (TRANCE), TNFSF12 (APO3L), TNFSF13 (April), TNFSF13B, TNFSF14 (HVEM-L), TNFSF15 (VEGI), TNFSF18, HGF (VEGFD), VEGF, VEGFB, VEGFC, ILIR1, IL1R2, IL1RL1, LL1RL2, IL2RA, IL2RB, IL2RG, IL3RA, IL4R, IL5RA, IL6R, IL7R, IL8RA, IL8RB, IL9R, ILI0RA, ILI0RB, IL1IRA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIFI, HGF, LEP (leptin), PTN, and THPO.

In another embodiment, a target molecule is a chemokine, chemokine receptor, or a chemokine-related protein selected from the group consisting of CCLI (I-309), CCL2 (MCP-1/MCAF), CCL3 (MIP-Ia), CCL4 (MIP-Ib), CCL5 (RANTES), CCL7 (MCP-3), CCL8 (mcp-2), CCLH (eotaxin), CCL13 (MCP-4), CCL15 (MIP-Id), CCL16 (HCC-4), CCL17 (TARC), CCL18 (PARC), CCL19 (MDP-3b), CCL20 (MIP-3a), CCL21 (SLC/exodus-2), CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CXCLI (GROI), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDFI), CXCL13, CXCL14, CXCL16, PF4 (CXCL4), PPBP (CXCL7), CX3CL1 (SCYDI), SCYEI, XCLI (lymphotactin), XCL2 (SCM-Ib), BLRI (MDR15), CCBP2 (D6/JAB61), CCRI (CKRI/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBII), CCR8 (CMKBR8/TERI/CKR-LI), CCR9 (GPR-9-6), CCRLI (VSHKI), CCRL2 (L-CCR), XCRI (GPR5/CCXCRI), CMKLRI, CMKORI (RDCI), CX3CR1 (V28), CXCR4, GPR2 (CCRI0), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TOPIO, CKLFSF2, CKLFSF3, CKLFSF4, CKLFSF5, CKLFSF6, CKLFSF7, CKLFSF8, BDNF, C5R1, CSF3, GRCCIO (CIO), EPO, FY (DARC), GDF5, HDFIA, DL8, PRL, RGS3, RGS13, SDF2, SLIT2, TLR2, TLR4, TREMI, TREM2, and VHL.

In another embodiment the heteromultimeric proteins of the invention are capable of binding one or more targets selected from the group consisting of ABCFI; ACVRI; ACVRIB; ACVR2; ACVR2B; ACVRLI; AD0RA2A; Aggrecan; AGR2; AICDA; AIFI; AIGI; AKAPI; AKAP2; AMH; AMHR2; ANGPTI; ANGPT2; ANGPTL3; ANGPTL4; ANPEP; APC; APOCI; AR; AZGPI (zinc-a-glycoprotein); B7.1; B7.2; BAD; BAFF (BLys); BAGI; BAII; BCL2; BCL6; BDNF; BLNK; BLRI (MDR15); BMPI; BMP2; BMP3B (GDFIO); BMP4; BMP6; BMP8; BMPRIA; BMPRIB; BMPR2; BPAGI (plectin); BRCAI; C19orfIO (IL27w); C3; C4A; C5; C5R1; CANTI; CASP1; CASP4; CAVI; CCBP2 (D6/JAB61); CCLI (1-309); CCLII (eotaxin); CCL13 (MCP-4); CCL15 (MIP-Id); CCL16 (HCC-4); CCL17 (TARC); CCL18 (PARC); CCL19 (MIP-3b); CCL2 (MCP-1); MCAF; CCL20 (MIP-3a); CCL21 (MTP-2); SLC; exodus-2; CCL22 (MDC/STC-I); CCL23 (MPIF-1); CCL24 (MPIF-2/eotaxin-2); CCL25 (TECK); CCL26 (eotaxin-3); CCL27 (CTACK/ILC); CCL28; CCL3 (MTP-1a); CCL4 (MDP-Ib); CCL5 (RANTES); CCL7 (MCP-3); CCL8 (mcp-2); CCNAI; CCNA2; CCNDI; CCNEI; CCNE2; CCRI (CKRI/HM145); CCR2 (mcp-IRB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBII); CCR8 (CMKBR8/TERI/CKR-LI); CCR9 (GPR-9-6); CCRLI (VSHKI); CCRL2 (L-CCR); CD164; CD19; CDIC; CD20; CD200; CD22; CD24; CD28; CD3; CD37; CD38; CD3E; CD3G; CD3Z; CD4; CD40; CD40L; CD44; CD45RB; CD52; CD69; CD72; CD74; CD79A; CD79B; CD8; CD80; CD81; CD83; CD86; CDHI (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKNIA (p21Wapl/Cipl); CDKNIB (p27Kipl); CDKNIC; CDKN2A (P16INK4a); CDKN2B; CDKN2C; CDKN3; CEBPB; CERI; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); CMKLRI; CMKORI (RDCI); CNRI; COL18A1; COLIAI; COL4A3; COL6A1; CR2; CRP; CSFI (M-CSF); CSF2 (GM-CSF); CSF3 (GCSF); CTLA4; CTNNBI (b-catenin); CTSB (cathepsin B); CX3CL1 (SCYDI); CX3CR1 (V28); CXCLI (GROI); CXCL10 (IP-10); CXCLII (1-TAC/IP-9); CXCL12 (SDFI); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYCI; CYSLTRI; DAB2IP; DES; DKFZp451J0118; DNCLI; DPP4; E2F1; ECGFI; EDGI; EFNAI; EFNA3; EFNB2; EGF; EGFR; ELAC2; ENG; ENO1; ENO2; ENO3; EPHB4; EPO; ERBB2 (Her-2); EREG; ERK8; ESRI; ESR2; F3 (TF); FADD; FasL; FASN; FCERIA; FCER2; FCGR3A; FGF; FGFI (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FELI (EPSILON); FILI (ZETA); FLJ12584; FLJ25530; FLRTI (fibronectin); FLTI; FOS; FOSLI (FRA-I); FY (DARC); GABRP (GABAa); GAGEBI; GAGECI; GALNAC4S-6ST; GATA3; GDF5; GFI1; GGT1; GM-CSF; GNASI; GNRHI; GPR2 (CCRIO); GPR31; GPR44; GPR81 (FKSG80); GRCCIO (CIO); GRP; GSN (Gelsolin); GSTPI; HAVCR2; HDAC4; HDAC5; HDAC7A; HDAC9; HGF; HIFIA; HDPI; histamine and histamine receptors; HLA-A; HLA-DRA; HM74; HMOXI; HUMCYT2A; ICEBERG; ICOSL; ID2; IFN-a; IFNAI; IFNA2; IFNA4; IFNA5; IFNA6; IFNA7; IFNB1; IFNgamma; DFNWI; IGBPI; IGFI; IGFIR; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A, IL1B; ILIF10; IL1F5; IL1F6; IL1F7; IL1F8; IL1F9; IL1HYI; IL1RI; IL1R2; IL1RAP; IL1RAPL1; IL1RAPL2; IL1RL1, IL1RL2, ILIRN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); EL7; EL7R; EL8; IL8RA; DL8RB; IL8RB; DL9; DL9R; DLK; INHA; INHBA; INSL3; INSL4; IRAKI; ERAK2; ITGAI; ITGA2; ITGA3; ITGA6 (a6 integrin); ITGAV; ITGB3; ITGB4 (b 4 integrin); JAGI; JAK1; JAK3; JUN; K6HF; KAII; KDR; KITLG; KLF5 (GC Box BP); KLF6; KLKIO; KLK12; KLK13; KLK14; KLK15; KLK3; KLK4; KLK5; KLK6; KLK9; KRT1; KRT19 (Keratin 19); KRT2A; KHTHB6 (hair-specific type H keratin); LAMAS; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIBI; midkine; MEF; MIP-2; MKI67; (Ki-67); MMP2; MMP9; MS4A1; MSMB; MT3 (metallothionectin-III); MTSSI; MUCI (mucin); MYC; MYD88; NCK2; neurocan; NFKBI; NFKB2; NGFB (NGF); NGFR; NgR-Lingo; NgR-Nogo66 (Nogo); NgR-p75; NgR-Troy; NMEI (NM23A); N0X5; NPPB; NROBI; NR0B2; NRIDI; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRPI; NRP2; NT5E; NTN4; ODZI; OPRDI; P2RX7; PAP; PARTI; PATE; PAWR; PCA3; PCNA; PDGFA; PDGFB; PECAMI; PF4 (CXCL4); PGF; PGR; phosphacan; PIAS2; PIK3CG; PLAU (uPA); PLG; PLXDCI; PPBP (CXCL7); PPID; PRI; PRKCQ; PRKDI; PRL; PROC; PROK2; PSAP; PSCA; PTAFR; PTEN; PTGS2 (COX-2); PTN; RAC2 (p21Rac2); RARB; RGSI; RGS13; RGS3; RNFIIO (ZNF144); ROBO2; S100A2; SCGB1D2 (lipophilin B); SCGB2A1 (mammaglobin2); SCGB2A2 (mammaglobin 1); SCYEI (endothelial Monocyte-activating cytokine); SDF2; SERPINAI; SERPINA3; SERP1NB5 (maspin); SERPINEI (PAI-I); SERPDMF1; SHBG; SLA2; SLC2A2; SLC33A1; SLC43A1; SLIT2; SPPI; SPRRIB (Sprl); ST6GAL1; STABI; STAT6; STEAP; STEAP2; TB4R2; TBX21; TCPIO; TDGFI; TEK; TGFA; TGFBI; TGFBIII; TGFB2; TGFB3; TGFBI; TGFBRI; TGFBR2; TGFBR3; THIL; THBSI (thrombospondin-1); THBS2; THBS4; THPO; TIE (Tie-1); TMP3; tissue factor; TLRIO; TLR2; TLR3; TLR4; TLR5; TLR6; TLR7; TLR8; TLR9; TNF; TNF-a; TNFAEP2 (B94); TNFAIP3; TNFRSFIIA; TNFRSFIA; TNFRSFIB; TNFRSF21; TNFRSF5; TNFRSF6 (Fas); TNFRSF7; TNFRSF8; TNFRSF9; TNFSFIO (TRAIL); TNFSFI 1 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-1 BB ligand); TOLLIP; Toll-like receptors; TOP2A (topoisomerase Ea); TP53; TPMI; TPM2; TRADD; TRAFI; TRAF2; TRAF3; TRAF4; TRAF5; TRAF6; TREMI; TREM2; TRPC6; TSLP; TWEAK; VEGF; VEGFB; VEGFC; versican; VHL C5; VLA-4; XCLI (lymphotactin); XCL2 (SCM-Ib); XCRI (GPR5/CCXCRI); YYI; and ZFPM2.

Preferred molecular target molecules for antibodies encompassed by the present invention include CD proteins such as CD3, CD4, CD8, CD16, CD19, CD20, CD34; CD64, CD200 members of the ErbB receptor family such as the EGF receptor, HER2, HER3 or HER4 receptor; cell adhesion molecules such as LFA-1, Mac1, p150.95, VLA-4, ICAM-1, VCAM, alpha4/beta7 integrin, and alphav/beta3 integrin including either alpha or beta subunits thereof (e.g., anti-CD11a, anti-CD18 or anti-CD11b antibodies); growth factors such as VEGF-A, VEGF-C; tissue factor (TF); alpha interferon alphaIFN); TNFalpha, an interleukin, such as IL-1beta, IL-3, IL-4, IL-5, IL-8, IL-9, IL-13, IL17A/F, IL-18, IL-13Ralpha1, IL13Ralpha2, IL-4R, IL-5R, IL-9R, IgE; blood group antigens; flk2/flt3 receptor; obesity (OB) receptor; mpl receptor; CTLA-4; RANKL, RANK, RSV F protein, protein C etc.

In one embodiment, the heteromultimeric proteins of this invention bind low-density lipoprotein receptor-related protein (LRP)-1 or LRP-8 or transferrin receptor, and at least one target selected from the group consisting of 1) beta-secretase (BACE1 or BACE2), 2) alpha-secretase, 3) gamma-secretase, 4) tau-secretase, 5) amyloid precursor protein (APP), 6) death receptor 6 (DR6), 7) amyloid beta peptide, 8) alpha-synuclein, 9) Parkin, 10) Huntingtin, 11) p75 NTR, and 12) caspase-6.

In one embodiment, the heteromultimeric proteins of this invention binds to at least two target molecules selected from the group consisting of: IL-1alpha and IL-1beta, IL-12 and IL-18; IL-13 and IL-9; IL-13 and IL-4; IL-13 and IL-5; IL-5 and IL-4; IL-13 and IL-1beta; IL-13 and IL-25; IL-13 and TARC; IL-13 and MDC; IL-13 and MEF; IL-13 and TGF-β; IL-13 and LHR agonist; IL-12 and TWEAK, IL-13 and CL25; IL-13 and SPRR2a; IL-13 and SPRR2b; IL-13 and ADAM8, IL-13 and PED2, IL17A and IL17F, CD3 and CD19, CD138 and CD20; CD138 and CD40; CD19 and CD20; CD20 and CD3; CD38 and CD138; CD38 and CD20; CD38 and CD40; CD40 and CD20; CD-8 and IL-6; CD20 and BR3, TNFalpha and TGF-beta, TNFalpha and IL-1beta; TNFalpha and IL-2, TNF alpha and IL-3, TNFalpha and IL-4, TNFalpha and IL-5, TNFalpha and IL6, TNFalpha and IL8, TNFalpha and IL-9, TNFalpha and IL-10, TNFalpha and IL-11, TNFalpha and IL-12, TNFalpha and IL-13, TNFalpha and IL-14, TNFalpha and IL-15, TNFalpha and IL-16, TNFalpha and IL-17, TNFalpha and IL-18, TNFalpha and IL-19, TNFalpha and IL-20, TNFalpha and IL-23, TNFalpha and IFNalpha, TNFalpha and CD4, TNFalpha and VEGF, TNFalpha and MIF, TNFalpha and ICAM-1, TNFalpha and PGE4, TNFalpha and PEG2, TNFalpha and RANK ligand, TNFalpha and Te38; TNFalpha and BAFF; TNFalpha and CD22; TNFalpha and CTLA-4; TNFalpha and GP130; TNFα and IL-12p40; VEGF and HER2, VEGF-A and HER2, VEGF-A and PDGF, HER1 and HER2, VEGF-A and VEGF-C, VEGF-C and VEGF-D, HER2 and DR5, VEGF and IL-8, VEGF and MET, VEGFR and MET receptor, VEGFR and EGFR, HER2 and CD64, HER2 and CD3, HER2 and CD16, HER2 and HER3; EGFR(HER1) and HER2, EGFR and HER3, EGFR and HER4, IL-13 and CD40L, IL4 and CD40L, TNFR1 and IL-1R, TNFR1 and IL-6R and TNFR1 and IL-18R, EpCAM and CD3, MAPG and CD28, EGFR and CD64, CSPGs and RGM A; CTLA-4 and BTNO2; IGF1 and IGF2; IGF1/2 and Erb2B; MAG and RGM A; NgR and RGM A; NogoA and RGM A; OMGp and RGM A; PDL-I and CTLA-4; and RGM A and RGM B.

Soluble antigens or fragments thereof, optionally conjugated to other molecules, can be used as immunogens for generating antibodies. For transmembrane molecules, such as receptors, fragments of these (e.g., the extracellular domain of a receptor) can be used as the immunogen. Alternatively, cells expressing the transmembrane molecule can be used as the immunogen. Such cells can be derived from a natural source (e.g., cancer cell lines) or may be cells which have been transformed by recombinant techniques to express the transmembrane molecule. Other antigens and forms thereof useful for preparing antibodies will be apparent to those in the art.

VI. ACTIVITY ASSAYS

The heteromultimeric proteins of the present invention can be characterized for their physical/chemical properties and biological functions by various assays known in the art.

The purified heteromultimeric proteins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include, without limitation, any direct or competitive binding assays using techniques such as western blots, radioimmunoassays, ELISA (enzyme linked immunosorbent assay), "sandwich" immunoassays, immunoprecipitation assays, fluorescent immunoassays, and protein A immunoassays. An illustrative antigen binding assay is provided below in the Examples section.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced heteromultimeric protein are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the heteromultimeric protein lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or U.S. Pat. No. 5,821,337. Useful effector cells for such assays include peripheral blood mononuclear cells (PBMC) and natural killer (NK) cells. Alternatively, or additionally, ADCC activity of the molecule of interest may be assessed in vivo, e.g., in a animal model such as that disclosed in Clynes et al. *PNAS (USA)* 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art.

VII. CONJUGATED PROTEINS

The invention also provides conjugated proteins such as conjugated antibodies or immunoconjugates (for example, "antibody-drug conjugates" or "ADC"), comprising any of the heteromultimeric proteins described herein (e.g., an antibody made according to the methods described herein) where one of the constant regions of the light chain or the heavy chain is conjugated to a chemical molecule such as a dye or cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In particular, as described herein, the use of heteromultimerization domains enables the construction of antibodies containing two different heavy chains (HC1 and HC2) as well as two different light chains (LC1 and LC2). An immunoconjugate constructed using the methods described herein may contain the cytotoxic agent conjugated to a constant region of only one of the heavy chains (HC1 or HC2) or only one of the light chains (LC1 or LC2). Also, because the immunoconjugate can have the cytotoxic agent attached to only one heavy or light chain, the amount of the cytotoxic agent being administered to a subject is reduced relative to administration of an antibody having the cytotoxic agent attached to both heavy or light chains. Reducing the amount of cytotoxic agent being administered to a subject limits adverse side effects associated with the cytotoxic agent.

The use of antibody-drug conjugates for the local delivery of cytotoxic or cytostatic agents, i.e., drugs to kill or inhibit tumor cells in the treatment of cancer (Syrigos and Epenetos, Anticancer Research 19:605-614 (1999); Niculescu-Duvaz and Springer, Adv. Drg. Del. Rev. 26:151-172 (1997); U.S. Pat. No. 4,975,278) allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., Lancet (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby. Both polyclonal antibodies and monoclonal antibodies have been reported as useful in these strategies (Rowland et al., Cancer Immunol. Immunother. 21:183-187 (1986)). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al., Jour. of the Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Chemotherapeutic agents useful in the generation of immunoconjugates are described herein (e.g., above). Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin, and the tricothecenes. See, e.g., WO 93/21232 published Oct. 28, 1993. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026.

Conjugates of an antibody and one or more small molecule toxins, such as a calicheamicin, maytansinoids, dolastatins, aurostatins, a trichothecene, and CC1065, and the derivatives of these toxins that have toxin activity, are also contemplated herein.

i. Maytansine and Maytansinoids

In some embodiments, the immunoconjugate comprises an antibody (full length or fragments) of the invention conjugated to one or more maytansinoid molecules.

Maytansinoids are mitototic inhibitors which act by inhibiting tubulin polymerization. Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines.

Immunoconjugates containing maytansinoids, methods of making same, and their therapeutic use are disclosed, for example, in U.S. Pat. Nos. 5,208,020, 5,416,064 and European Patent EP 0 425 235 B1, the disclosures of which are hereby expressly incorporated by reference. Liu et al., Proc. Natl. Acad. Sci. USA 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., Cancer Research 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansinoid conjugate was tested in vitro on the human breast cancer cell line SK-BR-3, which expresses $3\times10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020 (the disclosure of which is hereby expressly incorporated by reference). An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, Chari et al., Cancer Research 52:127-131 (1992), and U.S. Patent Application Publication No. 2005/0169933, the disclosures of which are hereby expressly incorporated by reference. Antibody-maytansinoid conjugates comprising the linker component SMCC may be prepared as disclosed in U.S. Patent Application Publication No. 2005/0169933. The linking groups include disulfide groups, thioether groups, acid labile groups, photolabile groups, peptidase labile groups, or esterase labile groups, as disclosed in the above-identified patents, disulfide and thioether groups being preferred. Additional linking groups are described and exemplified herein.

Conjugates of the antibody and maytansinoid may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene). Particularly preferred coupling agents include N-succinimidyl-3-(2-pyridyldithio) propionate (SPDP) (Carlsson et al., Biochem. J. 173:723-737 (1978)) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

ii. Auristatins and Dolastatins

In some embodiments, the immunoconjugate comprises an antibody of the invention conjugated to dolastatins or dolostatin peptidic analogs and derivatives, the auristatins (U.S. Pat. Nos. 5,635,483 and 5,780,588). Dolastatins and auristatins have been shown to interfere with microtubule dynamics, GTP hydrolysis, and nuclear and cellular division (Woyke et al., Antimicrob. Agents and Chemother. 45(12): 3580-3584 (2001)) and have anticancer (U.S. Pat. No. 5,663,149) and antifungal activity (Pettit et al., Antimicrob. Agents Chemother. 42:2961-2965 (1998)). The dolastatin or auristatin drug moiety may be attached to the antibody through the N-(amino) terminus or the C-(carboxyl) terminus of the peptidic drug moiety (WO 02/088172).

Exemplary auristatin embodiments include the N-terminus linked monomethylauristatin drug moieties DE and DF, disclosed in "Monomethylvaline Compounds Capable of Conjugation to Ligands," U.S. Application Publication No. 2005/0238649, the disclosure of which is expressly incorporated by reference in its entirety.

Typically, peptide-based drug moieties can be prepared by forming a peptide bond between two or more amino acids and/or peptide fragments. Such peptide bonds can be prepared, for example, according to the liquid phase synthesis method (see E. Schröder and K. Lübke, "The Peptides," volume 1, pp. 76-136, 1965, Academic Press) that is well known in the field of peptide chemistry. The auristatin/dolastatin drug moieties may be prepared according to the methods of: U.S. Pat. Nos. 5,635,483 and 5,780,588; Pettit et al., J. Nat. Prod. 44:482-485 (1981); Pettit et al., Anti-Cancer Drug Design 13:47-66 (1998); Poncet, Curr. Pharm. Des. 5:139-162 (1999); and Pettit, Fortschr. Chem. Org. Naturst. 70:1-79 (1997). See also Doronina, Nat. Biotechnol. 21(7):778-784 (2003); and "Monomethylvaline Compounds Capable of Conjugation to Ligands," U.S. Application Publication No. 2005/0238649, hereby incorporated by reference in its entirety (disclosing, e.g., linkers and methods of preparing monomethylvaline compounds such as MMAE and MMAF conjugated to linkers).

iii. Calicheamicin

In other embodiments, the immunoconjugate comprises an antibody of the invention conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, and 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., Cancer Research 53:3336-3342 (1993), Lode et al., Cancer Research 58:2925-2928 (1998) and the aforementioned U.S. patents to American Cyanamid). Another anti-tumor drug that the antibody can be conjugated to is QFA, which is an antifolate. Both calicheamicin and QFA have intracellular sites of action and do not readily cross the plasma membrane. Therefore, cellular uptake of these agents through antibody mediated internalization greatly enhances their cytotoxic effects.

iv. Other Cytotoxic Agents

Other antitumor agents that can be conjugated to the antibodies of the invention or made according to the methods described herein include BCNU, streptozoicin, vincristine and 5-fluorouracil, the family of agents known collectively LL-E33288 complex described in U.S. Pat. Nos. 5,053,394 and 5,770,710, as well as esperamicins (U.S. Pat. No. 5,877,296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes (see, for example, WO 93/21232, published Oct. 28, 1993).

The present invention further contemplates an immunoconjugate formed between an antibody and a compound with nucleolytic activity (e.g., a ribonuclease or a DNA endonuclease such as a deoxyribonuclease; DNase).

For selective destruction of a tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio- or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al., Biochem. Biophys. Res. Commun. 80:49-57 (1978)) can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., Cancer Research 52:127-131 (1992); U.S. Pat. No. 5,208,020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

v. Preparation of Conjugated Antibodies

In the conjugated antibodies of the invention, an antibody is conjugated to one or more moieties (for example, drug moieties), e.g., about 1 to about 20 moieties per antibody, optionally through a linker. The conjugated antibodies may be prepared by several routes, employing organic chemistry reactions, conditions, and reagents known to those skilled in the art, including: (1) reaction of a nucleophilic group of an antibody with a bivalent linker reagent via a covalent bond, followed by reaction with a moiety of interest; and (2) reaction of a nucleophilic group of a moiety with a bivalent linker reagent via a covalent bond, followed by reaction with the nucleophilic group of an antibody. Additional methods for preparing conjugated antibodies are described herein.

The linker reagent may be composed of one or more linker components. Exemplary linker components include 6-maleimidocaproyl ("MC"), maleimidopropanoyl ("MP"), valine-citrulline ("val-cit"), alanine-phenylalanine ("ala-phe"), p-aminobenzyloxycarbonyl ("PAB"), N-Succinimidyl 4-(2-pyridylthio) pentanoate ("SPP"), N-Succinimidyl 4-(N-maleimidomethyl)cyclohexane-1 carboxylate ("SMCC'), and N-Succinimidyl (4-iodo-acetyl)aminobenzoate ("SIAB"). Additional linker components are known in the art and some are described herein. See also "Monomethylvaline Compounds Capable of Conjugation to Ligands," U.S. Application Publication No. 2005/0238649, the contents of which are hereby incorporated by reference in its entirety.

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, or a plasmin protease.

Nucleophilic groups on antibodies include, but are not limited to: (i) N-terminal amine groups, (ii) side chain amine groups, e.g., lysine, (iii) side chain thiol groups, e.g., cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e., cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugated antibodies of the invention may also be produced by modification of the antibody to introduce electrophilic moieties, which can react with nucleophilic substituents on the linker reagent or drug or other moiety. The sugars of glycosylated antibodies may be oxidized, e.g., with periodate oxidizing reagents, to form aldehyde or ketone groups which may react with the amine group of linker reagents or drug or other moieties. The resulting imine Schiff base groups may form a stable linkage, or may be reduced, e.g., by borohydride reagents to form stable amine linkages. In one embodiment, reaction of the carbohydrate portion of a glycosylated antibody with either glactose oxidase or sodium meta-periodate may yield carbonyl (aldehyde and ketone) groups in the protein that can react with appropriate groups on the drug or other moiety (Hermanson, Bioconjugate Techniques). In another embodiment, proteins containing N-terminal serine or threonine residues can react with sodium meta-periodate, resulting in production of an aldehyde in place of the first amino acid (Geoghegan and Stroh, Bioconjugate Chem. 3:138-146 (1992); U.S. Pat. No. 5,362,852). Such aldehyde can be reacted with a drug moiety or linker nucleophile.

Likewise, nucleophilic groups on a moiety (such as a drug moiety) include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; and (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate. In yet another embodiment, the antibody may be conjugated to a "receptor" (such streptavidin) for utilization in tumor pre-targeting wherein the antibody-receptor conjugate is administered to the individual, followed by removal of unbound conjugate from the circulation using a clearing agent and then administration of a "ligand" (e.g., avidin) which is conjugated to a cytotoxic agent (e.g., a radionucleotide).

VIII. UTILITY

The present methods provided for herein find industrial applicability in the production of heteromultimeric proteins. The inventive methods reduce the amount of work involved in two separate fermentation and isolations as are technical difficulties inherent in two separate fermentations. Furthermore, elimination of the annealment and redox steps of the prior methods procedures can increase yields and decrease processing complexity and costs.

The heteromultimeric proteins described herein find use in, for example, in vitro, ex vivo and in vivo therapeutic methods. The invention provides various methods based on using one or more of these molecules. In certain pathological conditions, it is necessary and/or desirable to utilize heteromultimeric proteins, e.g., multispecific antibodies. The invention provides these heteromultimeric proteins, which can be used for a variety of purposes, for example as therapeutics, prophylactics and diagnostics. For example, the invention provides methods of treating a disease, said methods comprising administering to a subject in need of treatment a heteromultimeric protein of the invention, whereby the disease is treated. Any of the heteromultimeric proteins of the invention described herein can be used in therapeutic (or prophylactic or diagnostic) methods described herein.

For example, when the heteromultimeric protein is multivalent, a valuable benefit is the enhanced avidity they pose for their antigen. In addition to having intrinsic high affinity on a binding unit (ie, a Fab) to antigen basis, normal IgG antibodies also exploit the avidity effect to increase their association with antigens as a result of their bivalent binding towards the targets.

A heteromultimeric protein directed against two separate epitopes on the same antigen molecule may not only provide the benefit of enhanced binding avidity (because of bivalent binding), but may also acquire novel properties that are not associated with either of the parent antibodies. Thus, the heteromultimeric proteins of the invention find use in, for example, the blocking of receptor-ligand interactions.

The heteromultimeric proteins described herein also find use in the application of simultaneously blocking the signaling pathways of two targets with one molecule.

IX. THERAPEUTIC USES

The heteromultimeric proteins such as antibodies and antibody fragments described herein (e.g., an antibody and/or fragment thereof made according to the methods described herein) may be used for therapeutic applications. For example, such heteromultimeric proteins can be used for the treatment of tumors, including pre-cancerous, non-metastatic, metastatic, and cancerous tumors (e.g., early stage cancer), for the treatment of allergic or inflammatory disorders, or for the treatment of autoimmune disease, or for the treatment of a subject at risk for developing cancer (for example, breast cancer, colorectal cancer, lung cancer, renal cell carcinoma, glioma, or ovarian cancer), an allergic or inflammatory disorder, or an autoimmune disease.

The term cancer embraces a collection of proliferative disorders, including but not limited to pre-cancerous growths, benign tumors, and malignant tumors. Benign tumors remain localized at the site of origin and do not have the capacity to infiltrate, invade, or metastasize to distant sites. Malignant tumors will invade and damage other tissues around them. They can also gain the ability to break off from where they started and spread to other parts of the body (metastasize), usually through the bloodstream or through the lymphatic system where the lymph nodes are located. Primary tumors are classified by the type of tissue from which they arise; metastatic tumors are classified by the tissue type from which the cancer cells are derived. Over time, the cells of a malignant tumor become more abnormal and appear less like normal cells. This change in the appearance of cancer cells is called the tumor grade and cancer cells are described as being well-differentiated, moderately-differentiated, poorly-differentiated, or undifferentiated. Well-differentiated cells are quite normal appearing and resemble the normal cells from which they originated. Undifferentiated cells are cells that have become so abnormal that it is no longer possible to determine the origin of the cells.

The tumor can be a solid tumor or a non-solid or soft tissue tumor. Examples of soft tissue tumors include leukemia (e.g., chronic myelogenous leukemia, acute myelogenous leukemia, adult acute lymphoblastic leukemia, acute myelogenous leukemia, mature B-cell acute lymphoblastic leukemia, chronic lymphocytic leukemia, polymphocytic leukemia, or hairy cell leukemia), or lymphoma (e.g., non-Hodgkin's lymphoma, cutaneous T-cell lymphoma, or Hodgkin's disease). A solid tumor includes any cancer of body tissues other than blood, bone marrow, or the lymphatic system. Solid tumors can be further separated into those of epithelial cell origin and those of non-epithelial cell origin. Examples of epithelial cell solid tumors include tumors of the gastrointestinal tract, colon, breast, prostate, lung, kidney, liver, pancreas, ovary, head and neck, oral cavity, stomach, duodenum, small intestine, large intestine, anus, gall bladder, labium, nasopharynx, skin, uterus, male genital organ, urinary organs, bladder, and skin. Solid tumors of non-epithelial origin include sarcomas, brain tumors, and bone tumors.

Epithelial cancers generally evolve from a benign tumor to a preinvasive stage (e.g., carcinoma in situ), to a malignant cancer, which has penetrated the basement membrane and invaded the subepithelial stroma.

Multispecific protein complexes can also be used in these therapeutic applications, and antibodies that bind HER2 can in particular be used to treat breast cancer, colorectal cancer, lung cancer, renal cell carcinoma, glioma, or ovarian cancer.

Other subjects that are candidates for receiving compositions of this invention have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, Mycobacteria infections other than leprosy, myopia, ocular neovascular disease, optic pits, Osler-Weber syndrome (Osler-Weber-Rendu), osteoarthritis, Paget's disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogren's syndrome, solid tumors, Stargart's disease, Steven's Johnson disease, superior limbic keratitis, syphilis, systemic lupus, Terrien's marginal degeneration, toxoplasmosis, tumors of Ewing sarcoma, tumors of neuroblastoma, tumors of osteosarcoma, tumors of retinoblastoma, tumors of rhabdomyosarcoma, ulcerative colitis, vein occlusion, Vitamin A deficiency, Wegener's sarcoidosis, undesired angiogenesis associated with diabetes, parasitic diseases, abnormal wound healing, hypertrophy following surgery, injury or trauma (e.g., acute lung injury/ARDS), inhibition of hair growth, inhibition of ovulation and corpus luteum formation, inhibition of implantation, and inhibition of embryo development in the uterus.

Examples of allergic or inflammatory disorders or autoimmune diseases or disorders that may be treated using an antibody made according to the methods described herein include, but are not limited to arthritis (rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, atherosclerosis, arteriosclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis), respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, nongranulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and autoimmune asthma, conditions involving infiltration of T-cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, anti-glomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, chorioiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to antispermatozoan antobodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T-cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis.

In addition to therapeutic uses, the antibodies of the invention can be used for other purposes, including diagnostic methods, such as diagnostic methods for the diseases and conditions described herein.

X. DOSAGES, FORMULATIONS, AND DURATION

The proteins of this invention will be formulated, dosed, and administered in a fashion consistent with good medical practice. Factors for consideration in this context include the particular disorder being treated, the particular mammal being treated, the clinical condition of the individual subject, the cause of the disorder, the site of delivery of the agent, the method of administration, the scheduling of administration, and other factors known to medical practitioners. The "therapeutically effective amount" of the proteins to be administered will be governed by such considerations, and is the minimum amount necessary to prevent, ameliorate, or treat a particular disorder (for example, a cancer, allergic or inflammatory disorder, or autoimmune disorder). The proteins need not be, but are optionally, formulated with one or more agents currently used to prevent or treat the disorder. The effective amount of such other agents depends on the amount of proteins present in the formulation, the type of disorder or treatment, and other factors discussed above. These are generally used in the same dosages and with administration routes as used hereinbefore or about from 1 to 99% of the heretofore employed dosages. Generally, alleviation or treatment of a cancer involves the lessening of one or more symptoms or medical problems associated with the cancer. The therapeutically effective amount of the drug can accomplish one or a combination of the following: reduce (by at least 10%, 20%, 30%, 40%, 50%, 60%, 70%, 80%, 90%, 100% or more) the number of cancer cells; reduce or inhibit the tumor size or tumor burden; inhibit (i.e., to decrease to some extent and/or stop) cancer cell infiltration into peripheral organs; reduce hormonal secretion in the case of adenomas; reduce vessel density; inhibit tumor metastasis; reduce or inhibit tumor growth; and/or relieve to some extent one or more of the symptoms associated with the cancer. In some embodiments, the proteins are used to prevent the occurrence or reoccurrence of cancer or an autoimmune disorder in the subject.

In one embodiment, the present invention can be used for increasing the duration of survival of a human subject susceptible to or diagnosed with a cancer or autoimmune disorder. Duration of survival is defined as the time from first administration of the drug to death. Duration of survival can also be measured by stratified hazard ratio (HR) of the treatment group versus control group, which represents the risk of death for a subject during the treatment.

In yet another embodiment, the treatment of the present invention significantly increases response rate in a group of human subjects susceptible to or diagnosed with a cancer who are treated with various anti-cancer therapies. Response rate is defined as the percentage of treated subjects who responded to the treatment. In one aspect, the combination treatment of the invention using proteins of this invention and surgery, radiation therapy, or one or more chemotherapeutic agents significantly increases response rate in the treated subject group compared to the group treated with surgery, radiation therapy, or chemotherapy alone, the increase having a Chi-square p-value of less than 0.005. Additional measurements of therapeutic efficacy in the treatment of cancers are described in U.S. Patent Application Publication No. 20050186208.

Therapeutic formulations are prepared using standard methods known in the art by mixing the active ingredient having the desired degree of purity with optional physiologically acceptable carriers, excipients or stabilizers (Remington's Pharmaceutical Sciences ($20^{th}$ edition), ed. A. Gennaro, 2000, Lippincott, Williams & Wilkins, Philadelphia, Pa.). Acceptable carriers, include saline, or buffers such as phosphate, citrate and other organic acids; antioxidants including ascorbic acid; low molecular weight (less than about 10 residues) polypeptides; proteins, such as serum albumin, gelatin or immunoglobulins; hydrophilic polymers such as polyvinylpyrrolidone, amino acids such as glycine, glutamine, asparagines, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, PLURONICS™, or PEG.

Optionally, but preferably, the formulation contains a pharmaceutically acceptable salt, preferably sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are preferred preservatives. Optionally, the formulations of the invention can include a pharmaceutically acceptable surfactant at a concentration of 0.005 to 0.02%.

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsule and poly-(methyl-methacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences, supra.

Sustained-release preparations may be prepared. Suitable examples of sustained-release preparations include semipermeable matrices of solid hydrophobic polymers containing the heteromultimeric protein, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated heteromultimeric protein(s) remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The proteins described herein (e.g., a heteromultimeric protein such as a multispecific antibody made according to the methods described herein) are administered to a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration may be particularly desired if extensive side effects or toxicity is associated with antagonism to the target molecule recognized by the proteins. An ex vivo strategy can also be used for therapeutic applications. Ex vivo strategies involve transfecting or transducing cells obtained from the subject with a polynucleotide encoding a protein of this invention. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

In one example, the protein complex is (e.g., a heteromultimeric protein such as a multispecific antibody made according to the methods described herein) is administered locally, e.g., by direct injections, when the disorder or location of the tumor permits, and the injections can be repeated periodically. The protein complex can also be delivered systemically to the subject or directly to the tumor cells, e.g., to a tumor or a tumor bed following surgical excision of the tumor, in order to prevent or reduce local recurrence or metastasis.

XI. ARTICLES OF MANUFACTURE

Another embodiment of the invention is an article of manufacture containing one or more protein complexes described herein, and materials useful for the treatment or diagnosis of a disorder (for example, an autoimmune disease or cancer). The article of manufacture comprises a container and a label or package insert on or associated with the container. Suitable containers include, for example, bottles, vials, syringes, etc. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). At least one active agent in the composition is a heteromultimeric protein (e.g., an antibody or antibody fragment) of the invention. The label or package insert indicates that the composition is used for treating the particular condition. The label or package insert will further comprise instructions for administering the heteromultimeric protein composition to the subject. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In certain embodiments, the package insert indicates that the composition is used for treating breast cancer, colorectal cancer, lung cancer, renal cell carcinoma, glioma, or ovarian cancer.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials considered from a commercial and user standpoint, including other buffers, diluents, filters, needles, and syringes.

Kits are also provided that are useful for various purposes, e.g., for purification or immunoprecipitation of an antigen (e.g., HER2 or EGFR) from cells. For isolation and purification of an antigen (e.g., HER2 or EGFR) the kit can contain a heteromultimeric protein (e.g., an EGFR/HER2 antibody) coupled to beads (e.g., sepharose beads). Kits can be provided which contain the heteromultimeric protein(s) for detection and quantitation of the antigen in vitro, e.g., in an ELISA or a Western blot. As with the article of manufacture, the kit comprises a container and a label or package insert on or associated with the container. The container holds a composition comprising at least one heteromultimeric protein (e.g., multispecific antibody or antibody fragment) of the invention. Additional containers may be included that contain, e.g., diluents and buffers or control antibodies. The label or package insert may provide a description of the composition as well as instructions for the intended in vitro or diagnostic use.

The foregoing written description is considered to be sufficient to enable one skilled in the art to practice the invention. The following Examples are offered for illustrative purposes only, and are not intended to limit the scope of the present invention in any way. Indeed, various modifications of the invention in addition to those shown and described herein will become apparent to those skilled in the art from the foregoing description and fall within the scope of the appended claims.

In the experimental disclosure which follows, the following abbreviations apply: eq (equivalents); M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); ° C. (degrees Centigrade); h (hours); min (minutes); sec (seconds); msec (milliseconds); ADCC (antibody-dependent cellular cytotoxicity)); BsAb (bispecific antibody); $C_L$ (constant domain of light chain); $C_H$ (constant domain of heavy chain); CMC (complement-mediated cytotoxicity); Fab (antigen binding fragment); Fc (crystallized fragment); Fv (variable fragment ($V_L+V_H$)); EGFR (epidermal growth factor receptor); HC (heavy chain); IGFR (insulin-like growth factor receptor); LC (light chain); scFv (singlechain variable fragment ($V_L$ and $V_H$ tethered by an amino acid linker); VEGF (vascular endothelial growth factor); VEGFR2 (vascular endothelial growth factor receptor 2); $V_H$ (variable heavy domain); $V_L$ (variable light domain).

EXAMPLES

The present invention is described in further detain in the following examples which are not in any way intended to limit the scope of the invention as claimed. The attached Figures are meant to be considered as integral parts of the specification and description of the invention. All references cited are herein specifically incorporated by reference for all that is described therein. The following examples are offered to illustrate, but not to limit the claimed invention.

Example 1

Construction of Expression Vectors

This example illustrates the nucleic acid construct used to transform host cells.

Figure 2A:
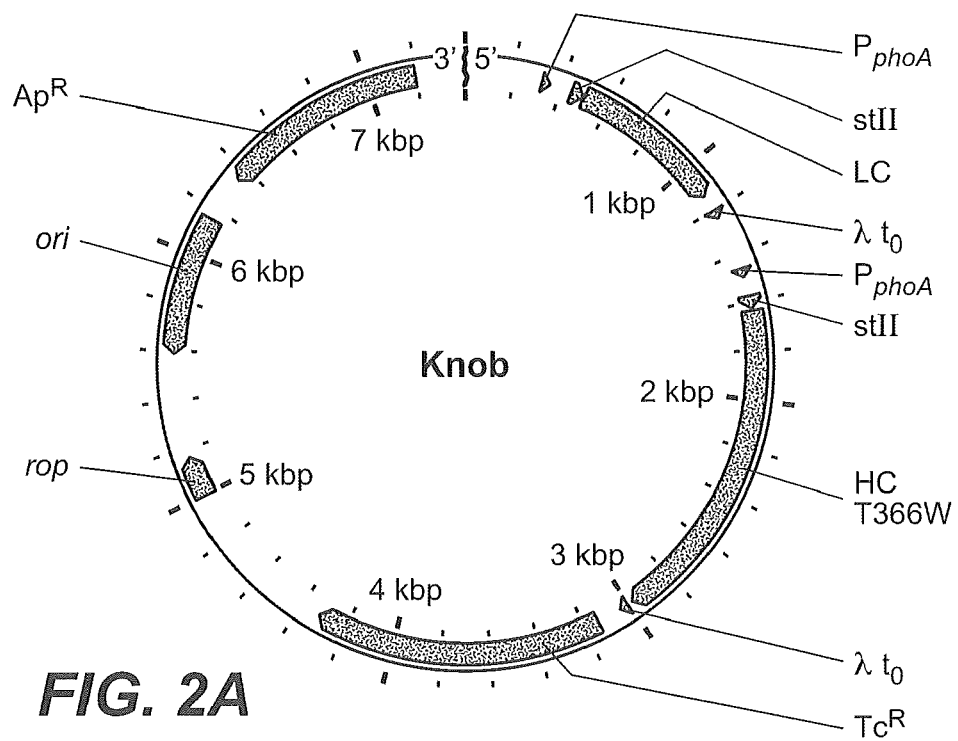
FIGS. 2A & B illustrates plasmids encoding the knob and hole half-antibodies, respectively.
Figure 2B:
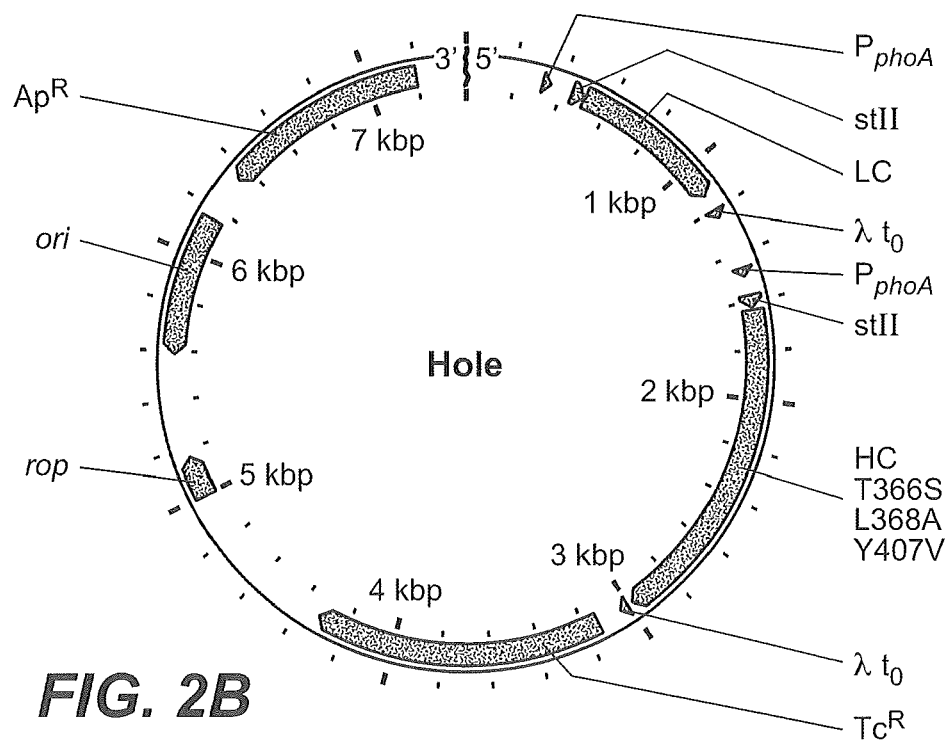
FIG. 9C-1, FIG. 9C-2 and FIG. 9C-3 show the mass spec chromatograms for the samples recovered and described in FIG. 9A. The samples with the EDTA showed the expected mass for the bispecific antibody and a mass for the excess half-antibody.

Generally, both the heavy and light chain DNA coding sequences were cloned into an expression plasmid that contained separate promoter elements for each of the sequences and antibiotic resistance for selection of bacterial cells that contain the expression plasmid. The vector constructs also encode the heat-stable enterotoxin II (STII) secretion signal (Picken et al., 1983, Infect. Immun. 42:269-275, and Lee et al., 1983, Infect. Immun. 42:264-268) for the export of the antibody polypeptides into the periplasmic space of the bacterial cell. Transcription of each chain is controlled by the phoA promoter (Kikuchi et al., 1981, Nucleic Acids Res., 9:5671-5678) and translational control is provided by previously described STII signal sequence variants of measured relative translational strength, which contain silent codon changes in the translation initiation region (TIR) (Simmons and Yansura, 1996, Nature Biotechnol. 14:629-634 and Simmons et al., 2002, J. Immunol. Methods, 263:133-147). A schematic drawing of the knob and hole plasmids is shown in FIGS. 2A and 2B, respectively.

While the present invention does not rely on specific antibody binding sequences, and is applicable to any half-antibody combinations, the Examples herein are directed to heteromultimeric antibodies directed to c-met, EGFR, IL-4 and IL-13. Examples of anti-c-met antibodies are given in U.S. Pat. No. 7,472,724, and U.S. Pat. No. 7,498,420. Examples of anti-EGFR antibodies are given in US Provisional Application 61/210,562 (filed 20 Mar. 2009), US Pat. Appln. Pub. No. 20080274114 (published 6 Nov. 2008) and U.S. Pat. No. 5,844,093 (granted 1 Dec. 1998). Examples of anti-IL-13 antibodies are described in U.S. Pat. No. 7,501,121 (granted 10 Mar. 2009), U.S. Pat. No. 7,615,213 (granted 10 Nov. 2009), WO 2006/085938 (published 17 Aug. 2006), US Pat Appln. Pub. No. 20090214523 (published 27 Aug. 2009), and U.S. Pat. No. 7,674,459 (granted 9 Mar. 2010). Examples of anti-IL-4 antibodies are described in US Pat. Appln. Pub. No. US 20080241160 (published 2 Oct. 2008), and U.S. Pat. No. 6,358,509 (granted 19 Mar. 2002).

Each half-antibody had either a knob (protuberance) or a hole (cavity) engineered into the heavy chain as described in U.S. Pat. No. 7,642,228. Briefly, a $C_H3$ knob mutant was generated first. A library of $C_H3$ hole mutants was then created by randomizing residues 366, 368 and 407 that are in proximity to the knob on the partner $C_H3$ domain. In the following examples, the knob mutation is T366W, and the hole has mutations T366S, L368A and Y407V in an IgG1 backbone. Equivalent mutations in other immunoglobulin isotypes is easily determined by one skilled in the art. Further, the skilled artisan will readily appreciate that it is preferred that the two half-antibodies used for the bispecific be the same isotype. Half-antibodies of different isotypes may be used but may need further mutations.

Although the vector described in this Example is for either the anti-c-Met or anti-EGFR half-antibody, one skilled in the art will readily appreciate that any antibody can be encoded in the plasmid. The starting plasmid for all constructs used herein is the previously described anti-tissue factor separate cistron plasmid, paTF50, with relative TIRs of 1 for heavy and 1 for light (Simmons et al., 2002, J. Immunol Methods, 263:133-147, and U.S. Pat. No. 6,979,556). An increase in the relative TIR strengths was used to increase the expression titers of these half-antibodies.

Example 2

Heteromultimeric Protein Production Using Separate Cell Cultures

The following example shows the production of heteromultimeric proteins when the cells expressing the monomeric components are grown in separate cultures. In this method the cells are grown and induced to express the half-antibody in separate cultures. In one method, the host cell cultures may be combined before protein purification. In another method the components may be purified first and then combined to form the heteromultimeric protein.

In both methods, a nucleic acid encoding the first hinge-containing polypeptide (e.g., a half-antibody (knob)) is introduced into a first host cell and a nucleic acid encoding the second hinge-containing polypeptide (e.g., a half-antibody (hole)) is introduced into a second host cell. Although this example illustrates the formation of a BsAb one skilled in the art will readily appreciate that the methods described are applicable to any heteromultimeric protein comprising a hinge region, e.g., affibodies, etc.

Method #1—Independent Production of Knob Half-Antibody and Hole Half-Antibody in Separate Cultures, Separate Purification of the Half-Antibodies, Mixing and Redox to Form Intact BsAb.

Figure 3A:
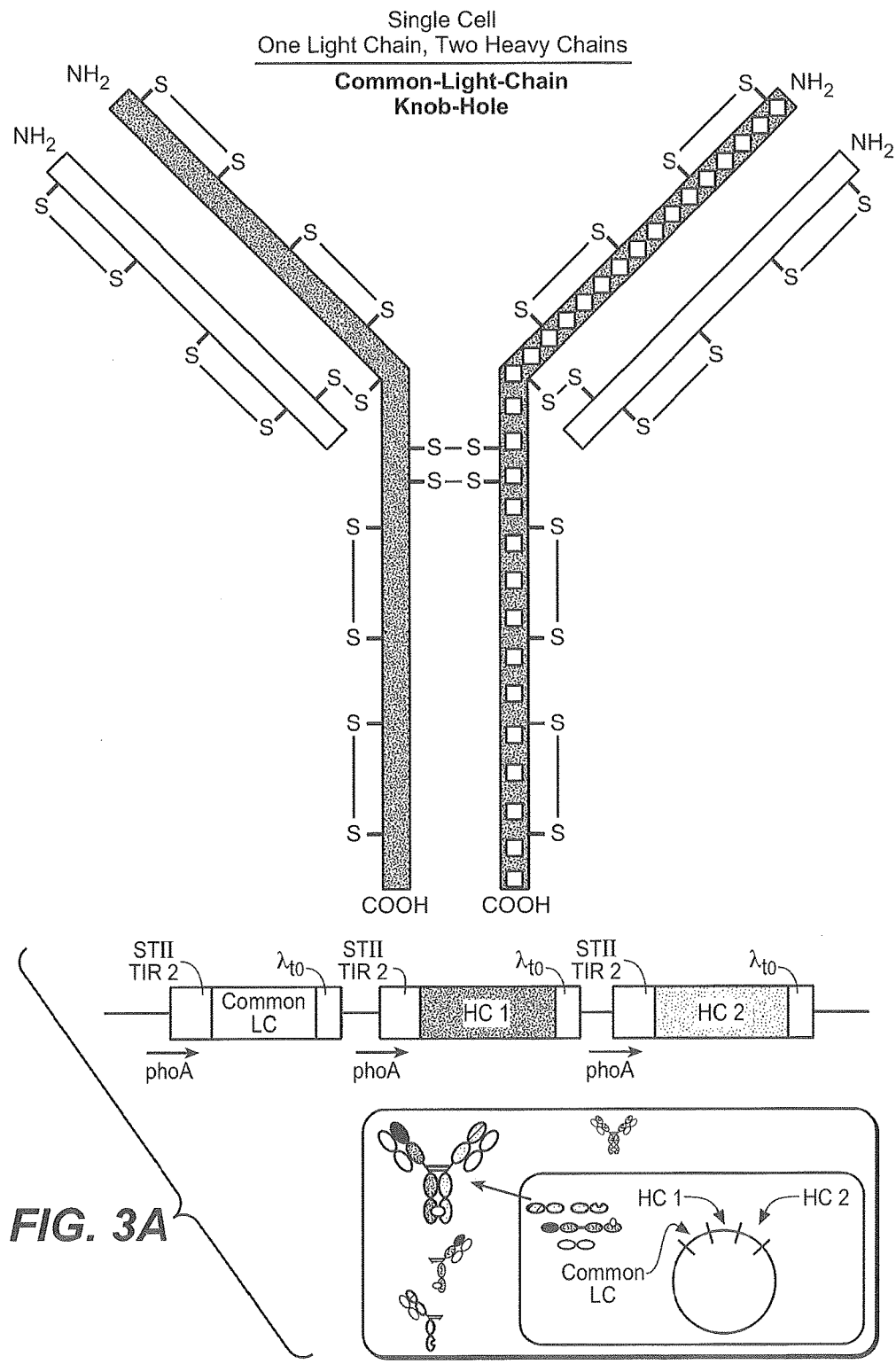
FIG. 3A illustrates the production of heteromultimeric proteins, e.g., bispecific antibodies, using the common light chain method. The produced BsAb has two different heavy chains with each being paired with a common light chain.
Figure 3B:
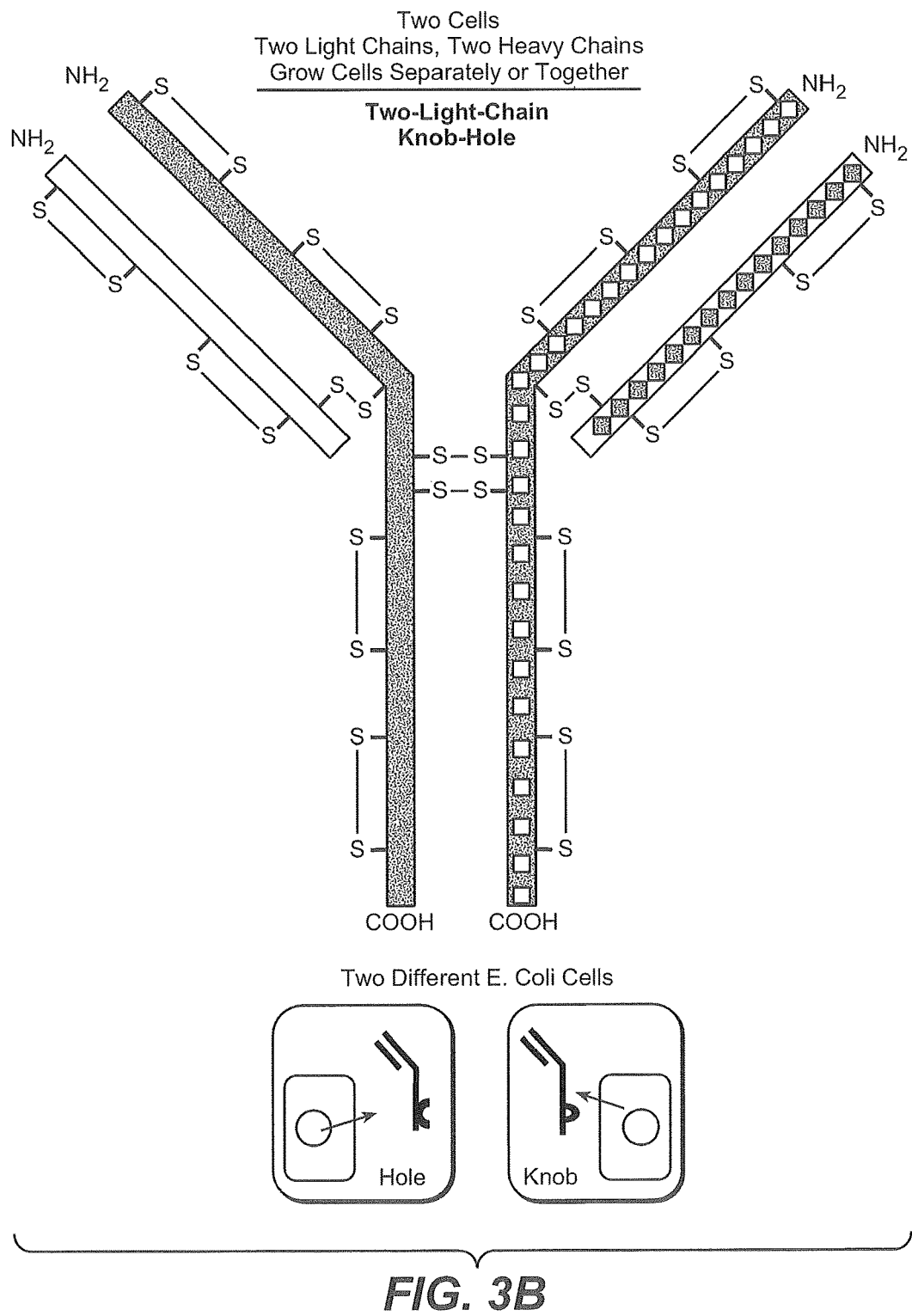
FIG. 3B illustrates the production of heteromultimeric proteins, e.g., bispecific antibodies, using separately engineered and expressed half-antibodies. The produced BsAb typically has two different heavy chains, each paired with its cognate light chain. In this method each light chain is not necessarily the same for each half-antibody.
Figure 4A:
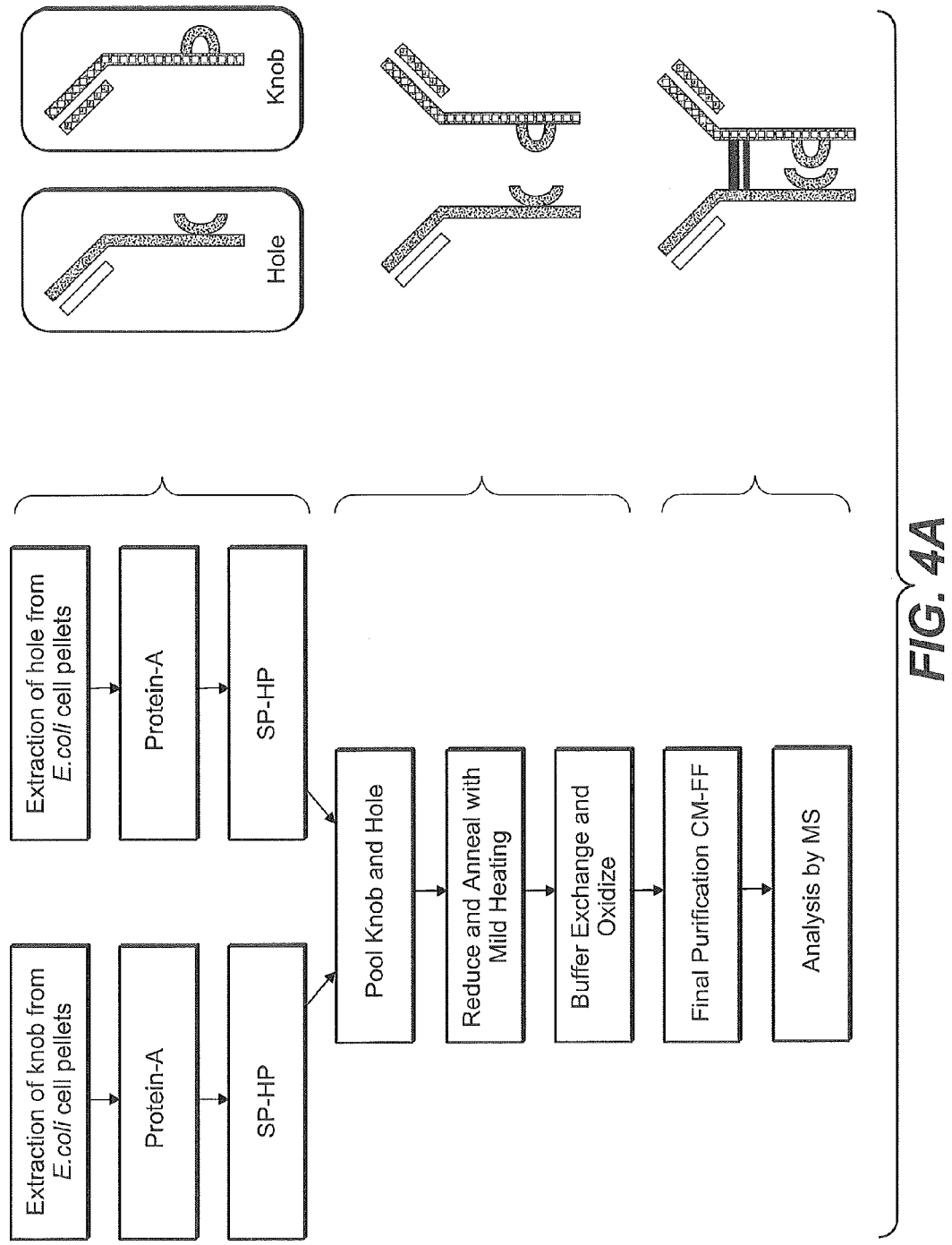
FIG. 4A is a flow diagram for the production of bispecific antibodies using separately engineered and expressed half-antibodies. In this method, redox chemistry is used.

Half-antibodies containing either the knob or hole mutations were generated in separate cultures by expressing the heavy and light chains using the constructs described in Example 1 in a bacterial host cell, e.g., *E. coli*. See FIGS. 3B and 4A. In this Method #1 the knob half-antibody was an anti-EGFR and the hole half-antibody was an anti-c-met. The expression plasmids of Example 1 were introduced into *E. coli* host strains 33D3 (Ridgway et al. (1999) 59 (11): 2718) or 64B4 (W3110 ΔfhuA ΔphoA ilvG+Δprc spr43H1 ΔdegP ΔmanA lacI$^q$ ΔompT) and transformants were selected on carbenicillin containing LB plates. Transformants were then used to inoculate an LB starter culture containing carbenicillin, and this was grown overnight with shaking at 30° C. The starter culture was diluted 100× into a phosphate limiting media C.R.A.P. (Simmons et al., 2002, J. Immunol. Methods, 263:133-147) containing carbenicillin, and this was grown for 24 hours with shaking at 30° C. The cultures were centrifuged, and the cell pellets frozen until the start of antibody purification. The pellets were thawed and resuspended in an extraction buffer containing 25 mM Tris-base adjusted to pH 7.5 with hydrochloric acid, 125 mM NaCl and 5 mM EDTA (TEB or Tris Extraction Buffer) with a volume to weight ratio of 100 mL TEB per 5 grams of cell pellet, and extracted by disrupting the cells using microfluidics by passing the resuspended mixture through a Microfluidics Corporation model 110F microfluidizer (Newton, Mass.) three times. The bacterial cell extract was then clarified by centrifugation for 20 minutes at 15,000×g and the supernatant collected and filtered through a 0.22 micron acetate filter prior to purification.

Figure 4B:
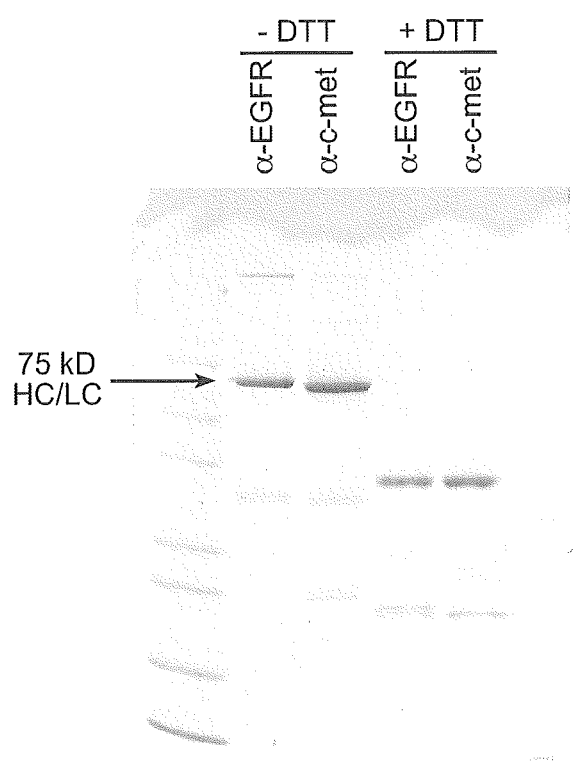
FIG. 4B shows a Coomassie stained gel. The two half-antibodies were analyzed under reducing and non-reducing conditions by SDS-PAGE. The predominant fraction is the 75 kD light chain-heavy chain pair for each half-antibody under non-reducing conditions. Under reducing conditions (e.g., treatment with DTT) each chain is visible as a separate band.
Figure 4C:
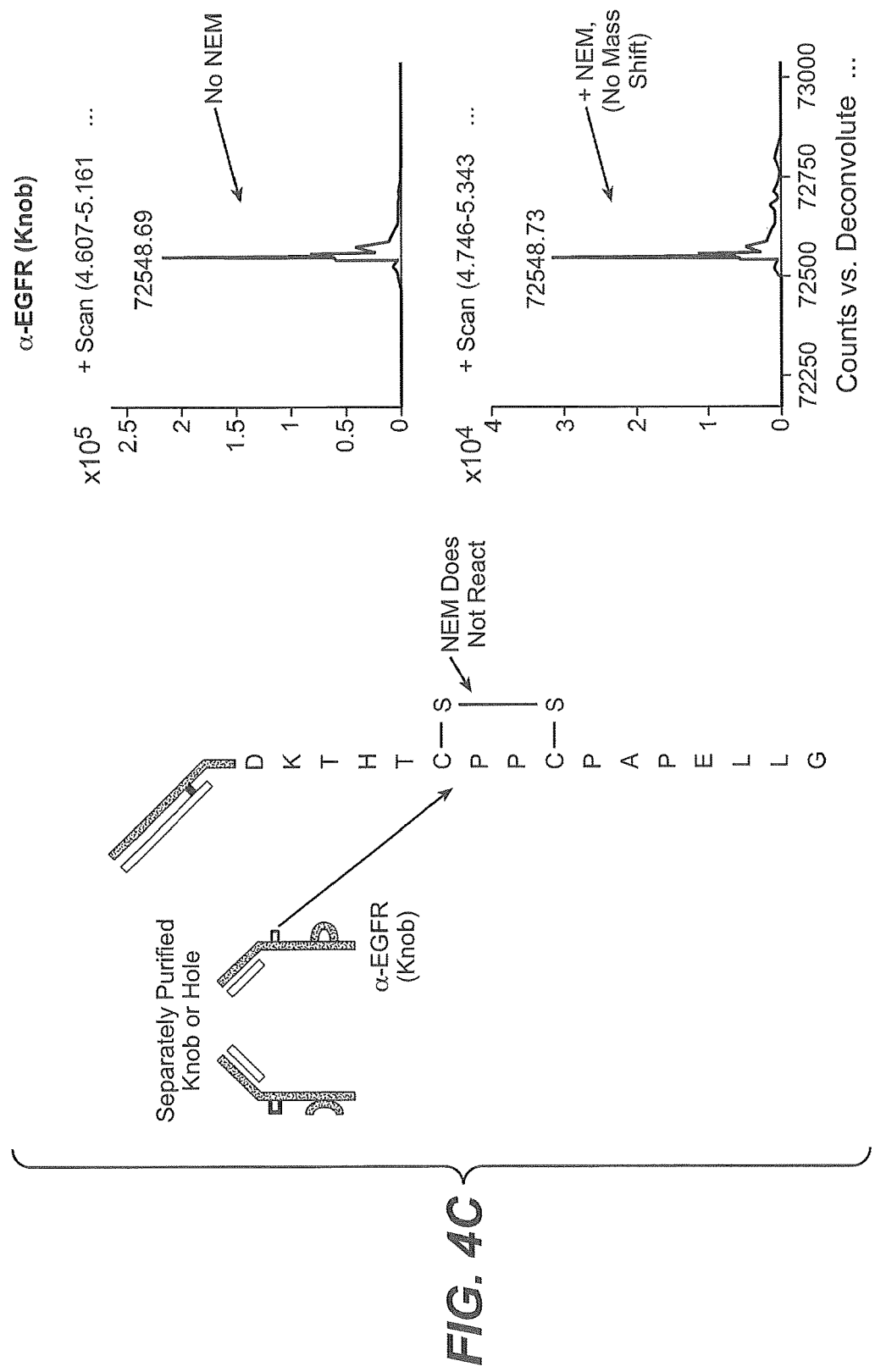
FIG. 4C shows the results of ESI-TOF mass spectrometry of a half-antibody with and without 1 mM N-ethylmaleimide (NEM) treatment. No change in the mass of the half-antibody is observed upon treatment with NEM indicating that all cysteines are fully oxidized. The oxidized hinge cysteines are represented as a cyclic disulfide in the depicted amino acid sequence. The expected mass for the half-antibody is 72,548 Daltons, which is what is observed by mass spectrometry indicating no covalent adducts.

Each half-antibody was purified separately by Protein A capture followed by cation exchange chromatography. Clarified cell extracts from the knob half-antibody were loaded onto a 1 mL HiTrap MabSelect SURE column from GE Healthcare (Pistcataway, N.J.) at 2 mL/min. After loading the column was washed with 10 column volumes (CV) of 40 mM sodium citrate, pH 6.0, 125 mM sodium chloride, and 5 mM EDTA followed by 5 column volumes of 20 mM sodium citrate at pH 6.0 to facilitate capture by the cation exchange column. The affinity captured half-antibodies were eluted with 10 column volumes (CV) of 0.2 mM acetic acid (pH 2-3) and directly captured on a 1 mL HiTrap SP-HP strong cation exchange column from GE Healthcare. The column was washed with 10 CV of buffer A containing 25 mM 2-(N-morpholino)ethanesulfonic acid (MES) pH 5.8. The half-antibodies were eluted with a linear gradient of 0-50% buffer B (25 mM MES, pH 5.8 and 1 M sodium chloride (NaCl)). Both proteins eluted between 20-40% B and the eluant peak as determined by UV absorbance at 280 nm and by non-reducing SDS-PAGE analysis of the collected fractions were pooled separately as the knob or hole half-antibody. Both proteins generally exhibited a major elution peak and all fractions that contained heavy chain and light chain species that were oxidized to one another were included in the pool. Analysis of the purified half-antibodies by reducing and non-reducing SDS-PAGE are shown in FIG. 4B. The results indicate that most of the expressed and captured protein is 75 kD in size. We confirmed this by ESI-TOF mass spectrometry shown in FIG. 4C. The mass of the half-antibodies were the expected masses indicating that there were no disulfide adducts on any cysteine, including the two cysteine residues in the hinge region. To determine if the hinge cysteines were reduced exhibiting a reactive free thiol, the proteins were reacted in at a neutral pH with 1 mM N-ethylmaleimide (NEM) for one hour before analysis by mass spectrometry. The mass of the protein was unchanged indicating that the hinge cysteines were oxidized to each other most likely in an intrachain disulfide, e.g., a cyclic disulfide. In order to assemble a fully intact, bispecific antibody using these two half-antibodies (knob and hole), it was necessary to first reduce the intrachain disulfides at the hinge region to liberate the cysteine free thiols so that they could subsequently be oxidized to the other heavy chain to form the 150 kD bispecific antibody.

Figure 4D:
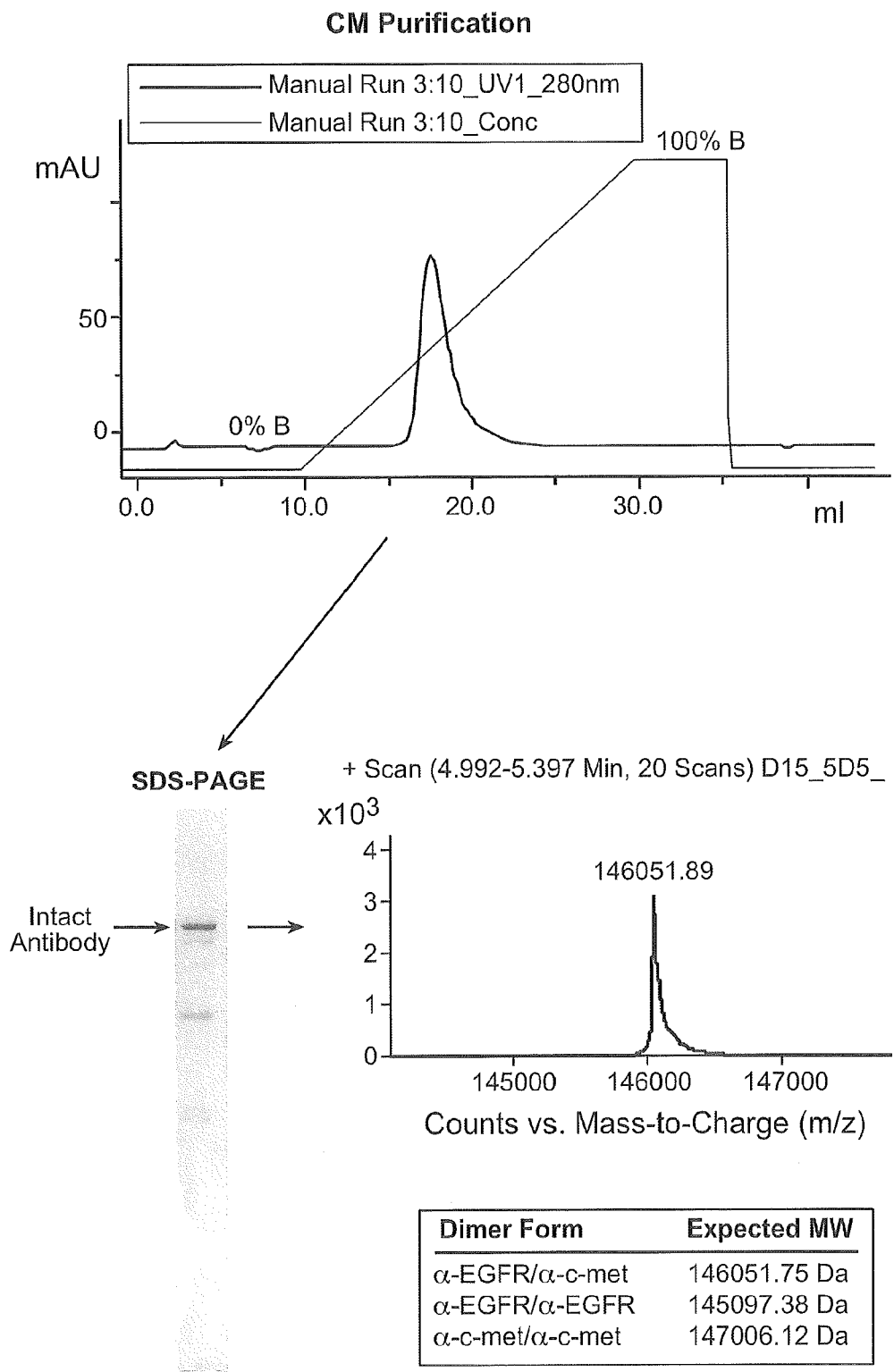
FIG. 4D shows the carboxymethyl (CM) chromatogram, a photo of a SDS-PAGE gel and the deconvoluted mass for the production of an anti-EGFR/anti-c-met bispecific antibody. The CM chromatography produces a single peak that is subsequently analyzed by SDS-PAGE. The major band on the gel is the full-length (i.e., intact) bispecific antibody. A minor band can also be seen at the 75 kD range. The major band was subsequently analyzed by mass spectrometry and indicated that the only detectable intact antibody product was in agreement with theoretical MW of an anti-EGFR/anti-c-met bispecific antibody.

To accomplish the annealing, reduction and reoxidation of the two complementary half-antibodies to form the intact bispecific molecules the following procedure was developed. After independent isolation, the purified proteins were combined together at equal mass in the Pool step of the procedure (shown in FIG. 5A), the pH of the pool was adjusted to 7.5 by adding one-tenth volume of 1 M Tris, pH 7.5, and proteins were reduced with 0.5 mM Tris[2-carboxyethyl] phosphine (TCEP) at room temperature. After reduction for 2 hours the pooled proteins were buffer exchanged into 25 mM Tris, pH 7.5, and 125 mM NaCl using 5 mL Zeba Desalt spin columns (Pierce, Rockford, Ill.) resulting in a volume of about 4 mLs of a protein concentration of 1 mg/mL. The proteins were then annealed by heating the mixture to 52° C. for 25 minutes followed by cooling to room temperature, about 20° C. The annealed antibodies were concentrated using 10 kD MW cutoff spin concentrators to a volume of 0.5 mL with a protein concentration of about 8 mg/mL and oxidized by the addition of 300 micromolar dehydroascorbic acid (DHAA) to the reaction mixture from a stock solution of 100 mM DHAA dissolved in dimethylsulfoxide. The amount of DHAA added for oxidation is about 10-fold excess over the protein molar concentration. After oxidation overnight at room temperature, the oxidized material was run on an S-200 gel filtration column (22 mL S200 Tricorn from GE Healthcare) in a buffer containing 25 mM MES pH 6.0 and 300 mM NaCl. The intact antibody was pooled and diluted 10-fold in water. The BsAb protein was then purified by weak cation exchange chromatography using a carboxymethyl (CM) resin (1 mL HiTrap CM-FF, GE Healthcare) with a pH gradient elution from 4.5 to 9.2. The buffer A and B composition consisted of 20 mM sodium citrate, 30 mM MES, 20 mM HEPES, 20 mM imidizole, 20 mM Tris, 20 mM CAPS, and 25 mM NaCl, where the A buffer is adjusted to pH 4.2 with HCl and the B buffer is adjusted to pH 9.2 (or 10.4) using NaOH. The purified material obtained after CM chromatography was analyzed by mass spectrometry to determine the exact molecular composition (FIG. 4D). Mass spec analysis indicated that the only detectable intact antibody product was with a MW of 146,051.89, which matches nearly identically with the heterodimeric knob-hole species anti-EGFR/anti-c-met with a theoretical MW of 145,051.75. The yield of this procedure, beginning with about 2 mg of the knob and 2 mg of the hole was about 0.5-1 mg.

Figures 5A, 5B:
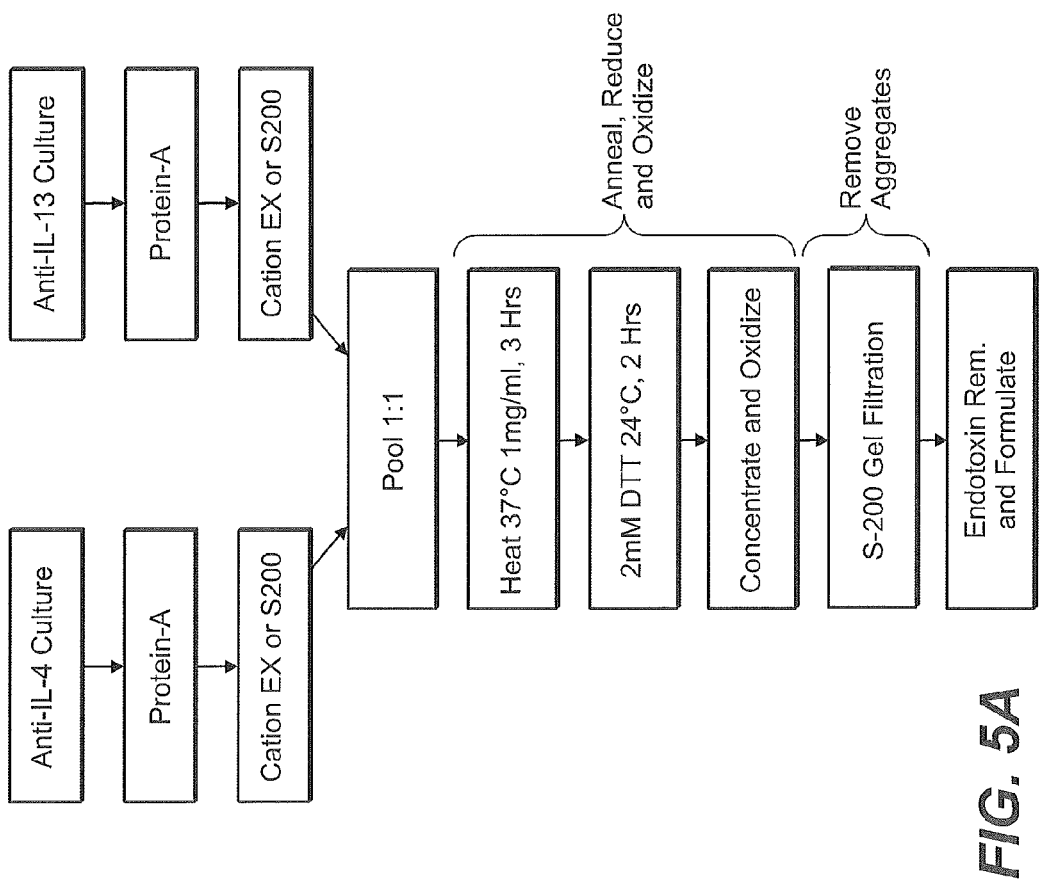
FIG. 5A is a flow diagram for the large scale production of bispecific antibodies using separately engineered and expressed half-antibodies.
FIG. 5B is photograph of a gel showing the purified half-antibodies were mostly the ~75 kD species under non-reducing conditions. Under reducing conditions (e.g., treatment with DTT) each chain is visible as a separate band.
Figure 5C:
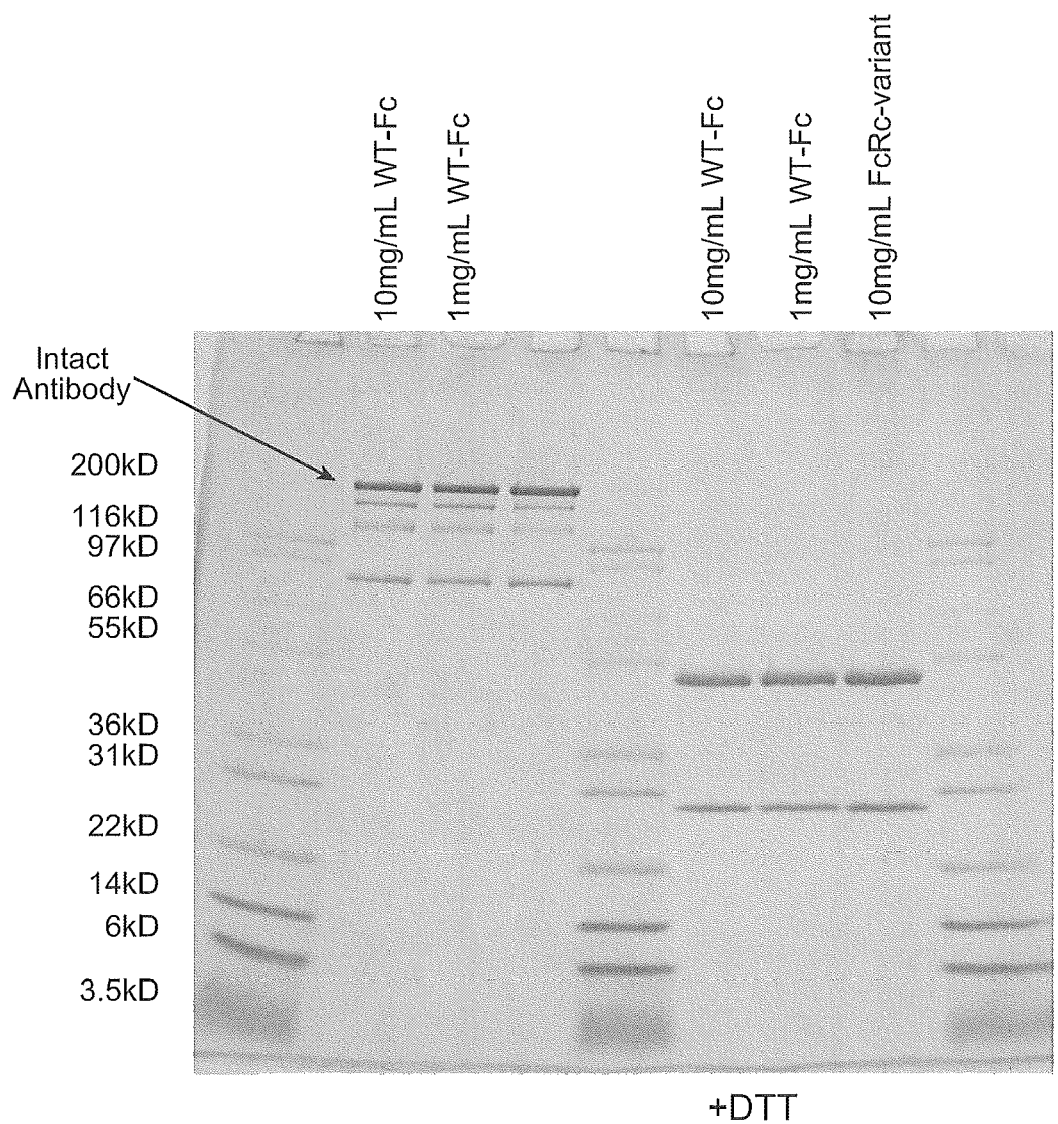
FIG. 5C shows the results of the SDS-PAGE analysis of the purified bispecific after removal of aggregates indicating that the major species is the intact bispecific antibody at 150 kD. Also shown are the same samples under reducing conditions indicating that all isolated product is either a light or heavy antibody chain.

For large scale production of antibodies for in vivo experimentation such as the determination of pharmacokinetic properties in non-human primates, 100 mg to gram scale quantities of antibody are needed. We developed a procedure using a separate, independent culture for each half-antibody as shown in FIG. 5A to produce intact bispecific antibodies in these quantities. For these preparations, 10 liter fermentations were required to produce cell pellets or whole broth with sufficient quantities of antibody (Simmons et al., 2002. J. Immunol. Methods, 263:133-147, and U.S. Pat. No. 6,979,556). In the course of experimentation either cell pellets or bacterial whole broth were used for biomass containing expressed half-antibodies. In some cases, a significant fraction of the antibody had leaked out into the media, where whole broth gave higher yields. For cell pellets, the material was resuspended in extraction buffer containing 25 mM Tris, pH 7.5, 5 mM EDTA, and 125 mM NaCl and lysed by microfluidization using a Model HC80003A microfluidizer from Microfluidics (Newton, Mass.). Whole broth was directly microfluidized without the addition of additives. In both cases, three passes of the material through the instrument was done. In this example, we prepared 500 mg of two versions of a bispecific antibody targeting the cytokines interlukin-4 (knob) and interleuikin-13 (hole).

The first version of the bispecific contained a human IgG1a Fc with only the knob and hole mutations and the second contained a further modified Fc with two mutations, T307Q and N434A, that lead to a greater affinity for the neonatal Fc receptor (FcRn). The second versions are expected to impart a slower clearance and longer half-life for the antibody. The hole antibody (targeting IL-4) and the knob antibody (targeting IL-13) of both versions of the Fc (WT-Fc for the former and FcRn-variant for the later) were both grown separately in 10 liter fermentation and the whole broth containing growth media and bacterial cells were homogenized and purified independently. After microfluidization of the whole broth, the extract was treated with an equal volume of 0.4% polyethyleneimine (PEI) (pH 9.0) to prepare the extract for clarification by centrifugation. The mixture was stirred for 3 hours at room temperature or overnight at 4° C. PEI caused extensive precipitation of the extract which was clarified by centrifugation at 15,000×g for 45 minutes. The supernatant was subsequently filtered by 0.22 micron filters before loading on a 100 mL Mab Select SURE Protein A capture column. The extract was loaded at 20 ml/min and washed with 40 mM sodium citrate, pH 6.0, and 100 mM NaCl until the UV absorbance at 280 reached a stable baseline, generally about 10 column volumes (CV). The wash buffer was changed to 20 mM sodium citrate, pH 6.0 and washed for about 2 CV. The captured half-antibody was eluted using 0.2 M acetic acid. After isolation by Protein A the antibodies were purified by cation exchange chromatography using S-FF resin (GE Healthcare) or gel filtration chromatography using S200 resin (GE Healthcare) to remove impurities and aggregates. The purified half-antibodies were mostly the ~75 kD species as seen in FIG. 5B. After the second isolation step, 500 mg of each half-antibody were pooled together at a concentration of 1 mg/mL and the pH was adjusted to 7.5 using 1 M Tris, pH 7.5. The mixture was heated to 37° C. in an incubator and monitored by gel filtration for the emergence of the 150 kD antibody species. After 2 hours, the annealing was complete showing complete conversion to the dimeric 150 kD species and the mixture was cooled to room temperature. The proteins were reduced by the addition of 2 mM DTT for two hours at 24° C. and subsequently concentrated to 20 mg/mL using 10 kD cutoff spin filters. The concentrated solution was oxidized by dialysis overnight in a buffer containing only 25 mM Tris, pH 8.0. The oxidized material was subsequently analyzed for purity and aggregation. The intact antibody species was determined by mass spectrometry to be the intact, fully oxidized heterodimeric bispecific molecule however gel filtration and SDS-PAGE analysis indicated the presence of significant amounts of aggregate, some of which was clearly the result of disulfide linked multimers (DATA not shown). To further purify the bispecific antibody for in vivo experimentation, the antibody was separated over an S-200 gel filtration column in Tris, pH 7.5 and 125 mM NaCl. The purified material exhibited a greater than 30% loss of material due to the removal of introduced aggregates. For the final stages of the preparation, the protein was adhered to a cation exchange column, washed with 0.1% TX114 in 50 mM sodium acetate, pH 5.0, to remove contaminating endotoxin, and eluted with a high pH buffer containing 50 mM Tris, pH 8.0. The eluted protein was then formulated by dialysis into a buffer suitable for in vivo experimentation and stored at 4° C. The final material consisting of the WT-Fc and the FcRn-variant was analyzed by SDS-PAGE, mass spectrometry, LAL assays for determining contaminating endotoxin levels, and gel filtration analysis. The results of the SDS-PAGE are shown in FIG.

Figure 6A:
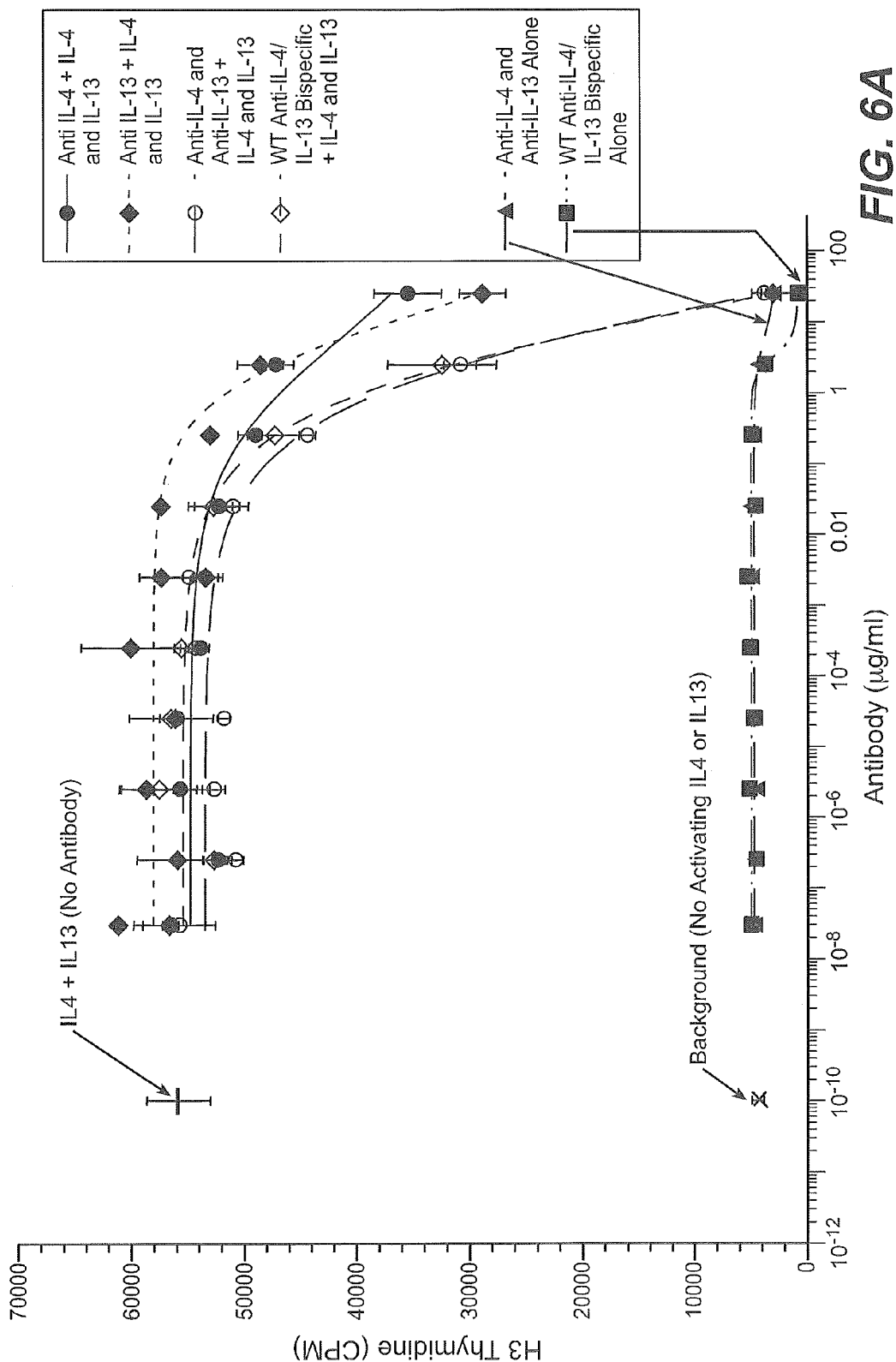
FIG. 6A is a graph showing the biological activity of the antibodies in a TF-2 cell proliferation assay testing neutralization of the cytokines IL-4 and IL-13. The graph shows that the bispecific possesses similar activity as the two mammalian-produced, full-length antibodies added together or separately.

5C, and indicate that the major species is the intact bispecific antibody at 150 kD. FIG. 6A shows the biological activity of the antibodies in a TF-2 cell proliferation assay testing neutralization of the cytokines IL-4 and IL-13. For the assay, anti-IL-4/IL-13 bispecific, anti-IL-4 and anti-IL-13 antibodies were used at a starting concentration of 25 ug/ml and serially diluted 10 fold in a 96 well culture plate (Falcon, Cat#353072) to a final concentration of 0.025 pg/ml in assay media (culture media without rhGM-CSF) or assay media containing 0.4 ng/ml human IL-4 (R&D Systems, Catalog #204-IL) plus 20 ng/ml human IL-13 (Genentech Inc.) in a final volume of 50 ul/well. Diluted antibodies were pre-incubated for 30 minutes at 37° C.

Following preincubation, TF-1 cells cultured in RPMI 1640 (Genentech, Inc.) 10% Fetal Bovine Serum (HyClone, Cat# SH300071.03), 2 mM L-glutamine 100 units/mL Penicillin 100 μg/mL Streptomycin (Gibco, Cat#10378) and 2 ng/mL rhGM-CSF (R&D Systems, Cat #215-GM) were washed 2 times with assay media and resuspended in assay media to obtain a final concentration of $2\times10^5$ cells/ml. 50 ul of cells were added to each well containing either the diluted antibodies, assay media plus IL-4 and IL-13 cytokines (maximal proliferation control) or assay media alone (background control). All samples were plated in duplicate. Plates were incubated at 37° C. at 5% $CO_2$ for 4 days. 1 uCi $^3H$ Thymidine (Perkin Elmer, Cat# NET027005MC) was added to each well during the final 4 hrs of incubation. Plates were harvested onto a Unifilter-96 GF/C (Perkin Elmer, Cat#6005174) using a Packard Filtermate, $^3H$ thymidine incorporation was measured using a TopCount NXT (Perkin Elmer). Data was plotted using KaleidaGraph. The results indicate that the WT anti-Il-4/anti-IL-13 bispecific antibody is as effective as IgG antibody combinations of IL-4 and IL-13 in neutralizing IL-4 and IL-13 activity.

Figure 6B:
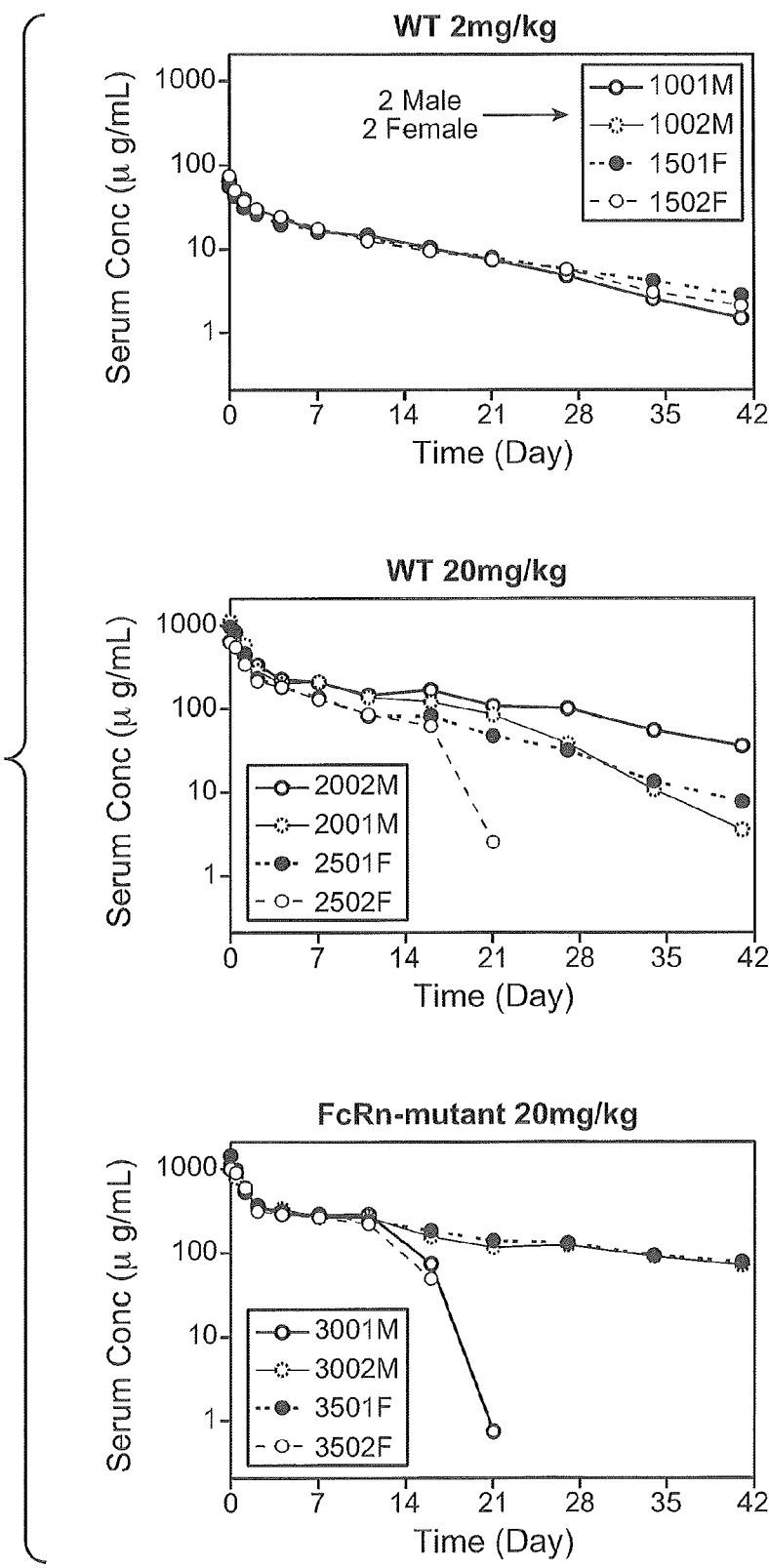
FIG. 6B is a panel of three graphs showing the pharmacokinetic (PK) properties of an anti-IL-4/anti-IL-13 bispecific antibody in cynomologous monkey for the wild-type Fc and a mutated Fc as determined by ELISA. The first graph shows the PK properties at a 2 mg/kg dose for the wild-type Fc. The middle graph shows the PK properties at a 20 mg/kg dose, also for the wild-type Fc. The final graph shows the PK properties at a 20 mg/kg dose for the mutant Fc. The bispecific exhibits the expected two compartment clearances in the animals tested. Females are represented by closed symbols and males are represented by open symbols. In three animals, an anti-therapeutic response was seen as indicated by the sharp decrease in measured antibody in serum at day 21.

The two antibodies (WT anti-IL-4/anti-IL-13 and FcRn-variant anti-IL-4/anti-IL-13) were then tested for their pharmacokinetic (PK) properties in cynomologous monkey. Using a single dose injection, the WT molecule formulated in 20 mM histidine-acetate, pH 5.5, 240 mM sucrose, and 0.02% Tween 20 at 10.8 mg/mL and 1 mg/mL and the FcRn-variant in 20 mM sodium phosphate, pH 7.5, 240 mM sucrose, and 0.02% Tween 20 at 10.5 mg/mL, were administered by IV injection. The dosing level was 20 mg/kg and 2 mg/kg for the two WT concentrations and 20 mg/kg for the FcRn-variant. Serum samples from two female and two male monkeys that were injected with the three treatments were taken periodically over the course of 42 days. The serum samples were assayed for the intact bispecific antibody by ELISA wherein one antigen, either IL-4 or IL-13, was coated onto the plates and the antibody subsequently captured from the serum. The amount of captured bispecific antibody present was determined by detection with a second biotinylated ligand either IL-13 or IL-4 (whichever ligand had not been coated onto the plates), and enzyme-coupled streptavidin. The results in FIG. 6B shows the expected two compartment clearances of the three samples. The PK properties of the two different versions of the antibody are shown in Table 2 in comparison to two other antibodies that are derived from CHO production hosts (Avastin and Herceptin) and contain Fc-glycosylation. It is clear that the *E. coli* produced bispecific antibody is similar to the CHO derived antibodies from a standard process and that the FcRn-variant has a longer half-life.

TABLE 2

| Population Mean (% RSE) | Vc (mL/kg) | CL (mL/kg/day) | T½ (day) |
|---|---|---|---|
| WT | 29.0 (9.48) | 4.49 (7.66) | ~10 |
| FcRn | 15.8 (5.72) | 2.11 (2.47) | ~18 |
| Avastin | | 4.3 | ~12 |
| Herceptin | | 5.5 | ~9 |

Method #2—Production of Knob Half-Antibody and Hole Half-Antibody in Separate (i.e., Independent) Cultures, Mixing Whole Broth Prior to Purification of the Half-Antibodies and Lysis without the Addition of a Reductant to Form Intact BsAb.

This method was an attempt to reduce the number of steps in the process by purifying the knob and the hole half-antibodies at the same time. Therefore, fermentation broths were mixed prior to pelleting and resuspending in extraction buffer. It was thought that each host cell would release its expressed half-antibody containing the cyclic disulfide within the hinge region into the extraction buffer upon cell membrane disruption. Subsequently, the purification of both half-antibodies could be done simultaneously followed by the redox-annealing step to form the intact BsAb. Surprisingly, we discovered that the knob-hole antibodies heterodimerized and oxidized on their own to form a full length antibody (~150 kD) at greater than 20% of the combined total of the intact and half-antibody (~75 kD) (see Table 3).

Figure 7:
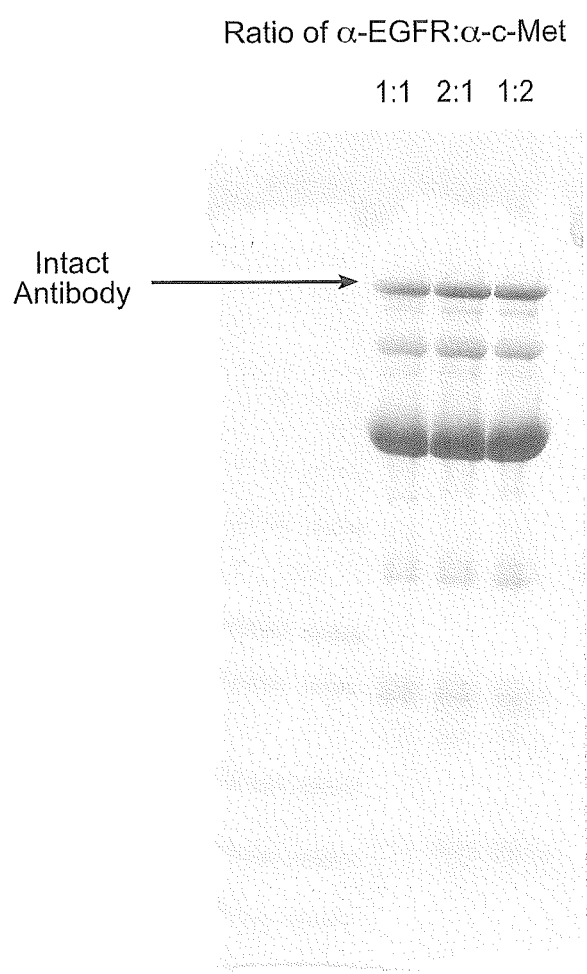
FIG. 7 is a photograph of a polyacrylamide gel. Whole fermentation broth was mixed prior to lysis at varying ratios. After lysis protein was extracted and loaded onto the gel under non-reducing conditions. Purified bispecifics formed during this procedure are visible as the top band on the gel.

The knob half-antibody and hole half-antibody expressing host cells were grown and induced in separate cultures using the process as described in Method #1, supra. The whole cell fermentation broth from each culture was mixed with the other at three different volume ratios and then centrifuged to form a single cell pellet. The whole cell fermentation broths were mixed together to a final volume of 500 mL at an (anti-c-met):(anti-EGFR) ratio of 1:1, 2:1 or 1:2, with the intent to match recovery of the two antibodies in relatively equal abundance and knowing that the anti-EGFR half antibody expressed similar to the cMet antibody under the same conditions. Each cell pellet was resuspended in extraction buffer and lysed. Protein was extracted and purified by Protein-A chromatography followed by cation exchange chromatography as described in Example 2, Method #1. The extraction buffer contained 25 mM Tris, pH 7.5, 125 mM NaCl, and 5 mM EDTA. When purified separately, each of the knob-half-antibody and hole-half-antibody form a cyclic disulfide within the hinge region, i.e., an intrachain disulfide, preventing covalent association of the knob and hole heavy chains. However, it was found that when the first and second host cells were lysed together either after co-culturing or after mixing whole fermentation broths prior to centrifugation, there was some level of assembly into the intact antibody species. FIG. 7 shows the intact antibody species observed in the three ratios. This suggested that modifications to the procedure could result in spontaneous formation of the intact bispecific antibody which could substantially eliminate the need for additional chemistry steps.

Quantitation of the two protein species was done by separating 5 micrograms of protein by SDS-PAGE using a Novex 4-20% Tris-Glycine gel (Invitrogen, Carlsbad Calif.). After electrophoresis the gel was stained with colloidal Coomassie stain containing 150 mM ammonium sulfate, 1.74 M acetic acid, 10% methanol and 0.4 g/L Coomassie Dye R250 in water. The gel was destained with 10% acetic acid in water and subsequently equilibrated in Gel-Dry Drying Solution (Invitrogen) and dried between two sheets of cellophane. After drying the gel, the protein bands were quantified by the Odyssey IR imaging system (LI-COR Biosciences, Lincoln, Nebr.) at 700 nm.

TABLE 3

Licore fluorescent signals for intact antibodies and half-antibodies after mixed isolations from two separately grown knob and hole cultures. [this is a measure of a hinge]

| Volume Ratio (c-met:EGFR) | 150 kD RFUs | 75 kD RFUs | Combined RFUs | % of 150 RFU/total |
|---|---|---|---|---|
| 1:1 | 36.01 | 98.78 | 134.8 | 26.72 |
| 2:1 | 36.8 | 107 | 143.8 | 25.59 |
| 1:2 | 34.64 | 107.83 | 142.5 | 24.31 |

Method #3—Production of Knob Half-Antibody and Hole Half-Antibody in Independent Cultures, Independent Centrifugation, Pellets Mixed & Resuspended Followed by Lysis, and Purification of the BsAb without the Addition of a Reductant.

This method is an attempt to reduce the number of steps in the process by purifying the knob and the hole at the same time.

The cells are cultured independently and pelleted by centrifugation. The pellets are mixed and resuspended together in extraction buffer. It is believed that the half-antibodies will be released into the extraction buffer upon disruption of the cell membranes and that a similar product profile will be seen as with Method #2, above.

Example 3

Heteromultimeric Protein Production Using a Single Mixed Cell Culture

This example illustrates the formation of heteromultimeric proteins from a culture comprising two host cell populations, wherein there is no addition of a reductant in the process.

Method #4—Production of Knob Half-Antibody and Hole Half-Antibody from Different Cell Populations in the Same Culture to Form Intact BsAb without the Addition of Reductant.

Co-culture experiments were first performed in 0.5 liter shake flasks with two different E. coli transformants containing either a knob or hole half-antibody. For this experiment, a starter culture of both the knob (anti-EGFR) and hole (anti-cMet) half-antibodies were produced by overnight culture in LB-media (100 μg/ml carbenicillin) in 5 mL cultures at 30° C. The overnight cultures of equal $OD_{600}$ were used to inoculate 500 ml complete CRAP-media (100 μg/ml carbenicillin) in three different ratios (anti-EGFR: anti-cMet; 1.5:1, 1:1 and 1:1.5) keeping the total seed volume to 1/100 of the culture. Cells were grown for 24 hrs at 30° C., 200 rpm. The cells were then pelleted by centrifugation (6750×g, 10 minutes, 4° C.) and used for purification.

The cells were resuspended in extraction buffer containing 25 mM Tris, pH 7.5, 5 mM EDTA, and 125 mM NaCl at a ratio of 100 mL per 10 g cell pellet. After extraction by microfluidization and preparation for chromatography as described in Example 2, the cell extracts of the three different ratios were purified by first capturing the bispecific antibody on a Mab Select SURE 1 mL HiTrap column (GE Healthcare, S. San Francisco, Calif.) and with a column wash buffer containing only 40 mM sodium citrate at pH 6.0. After washing and elution as described in Example 2, the protein A capture pools were loaded onto an SP-HP cation exchange column and purified as described in Example 2. After separation by cation exchange, the chromatographic peaks from each of the three purifications were pooled and concentrated to a volume of about 50-100 microliters, and with a protein concentration of about 15 mg/mL. The initial inoculation ratios appeared to make a difference in the final amount of intact antibody, and this was a higher proportion of intact bispecific antibody to lower molecular weight forms than was observed when the cell pellets were mixed together after overnight culturing at 37° C. See Table 4.

TABLE 4

| Inoculation Ratio | 150 kD RFUs | 75 kD RFUs | Combined RFUs | % of 150 RFU/total |
|---|---|---|---|---|
| 1.5 to 1 | 11.71 | 10.28 | 22.0 | 53.25 |
| 1 to 1 | 9.09 | 8.96 | 18.1 | 50.36 |
| 1 to 1.5 | 7.28 | 8.71 | 16.0 | 45.53 |

Figure 8B:
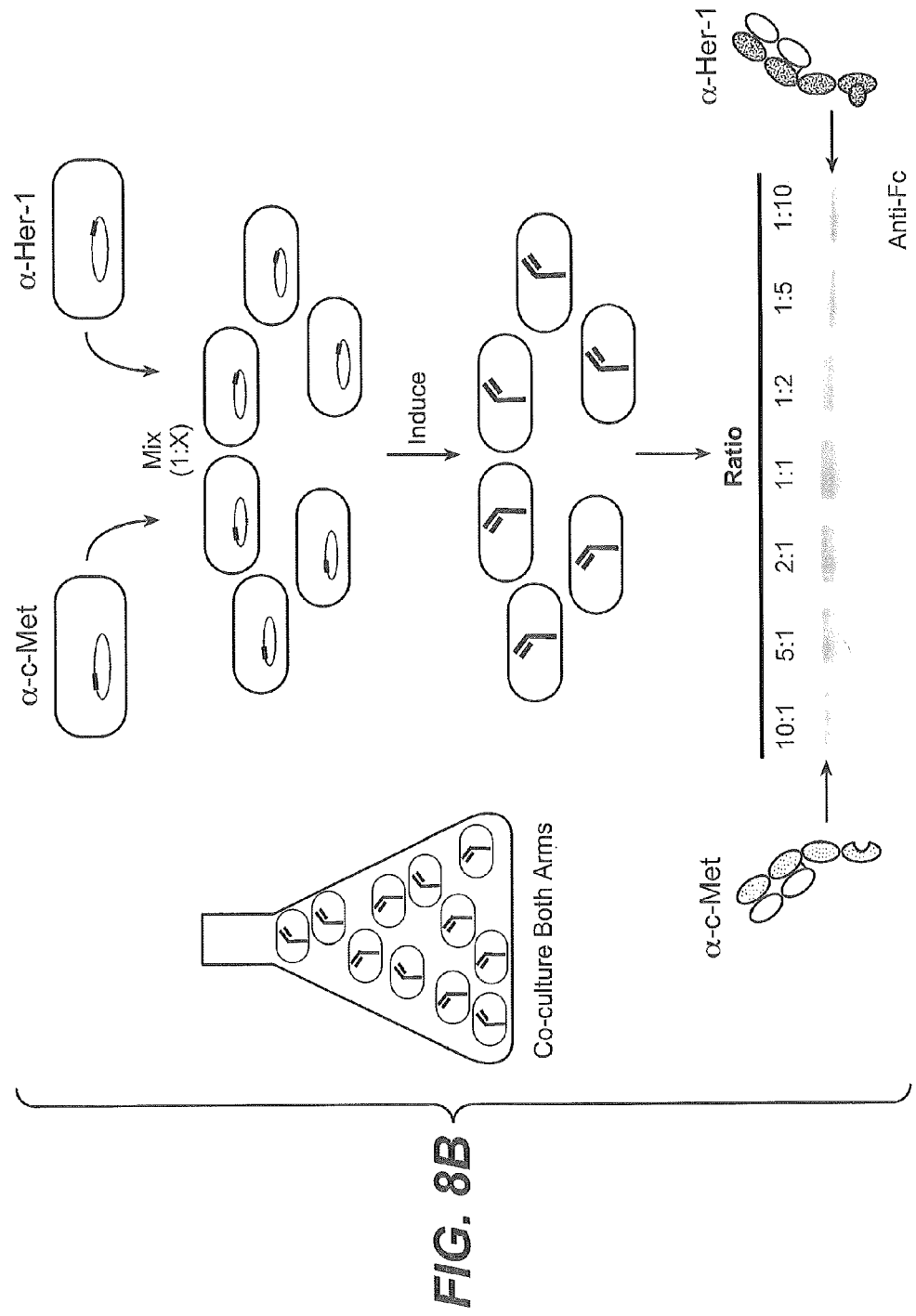
FIG. 8B is a schematic of a co-culture experiment varying the cell population of the initial inoculation. The ratios used and the relative amount of full-length bispecific are shown at the bottom of the figure.

To determine if co-culture can be extended to the 10 liter fermentation scale, which is critical for scale up procedures, several experiments were done with the anti-EGFR and anti-cMet half-antibodies. For 10 liter fermentations, an inoculation starting culture was used that contained a 1:1 cell ratio of anti-EGFR and anti-cMet. The 10 liter co-cultures were grown under identical conditions as for the single half-antibody cultures described in Example 2. Either cell pellet or whole broth was used for extraction and isolation of the antibody material, also as described above. For extraction of material from the cell pellets, about 2.5 kg of paste was produced from one 10 liter fermentation. The cell pellets were resuspended in 5 Liters of buffer containing 25 mM Tris, pH 7.5, and 125 mM NaCl. The pellet was treated with a polytron mixer for 2 minutes prior to resuspending the pellet, and then microfluidized, clarified, and prepared for Protein A capture as described in Example 2. The fermentation experiment was repeated two more times and the results of the co-culture isolation from 10 liter fermentors are shown in FIG. 8C. Mass spectrometry was used to characterize the ~150 kD protein and the ~75 kD protein to determine the molecular components. To our surprise, the dominant upper MW protein is the bispecific antibody and the ~75 kD protein was primarily the cMet half-antibody due to its differential expression profile. This indicates that the bispecific antibody has completely formed without the need for additional chemistry steps. Because the bispecific antibody is a 1:1 stoichiometric combination of the knob and hole half-antibodies, the presence of only a 75 kD protein indicates that the majority of the limiting half-antibody had been spontaneously incorporated into the intact bispecific antibody.

Figure 8D:
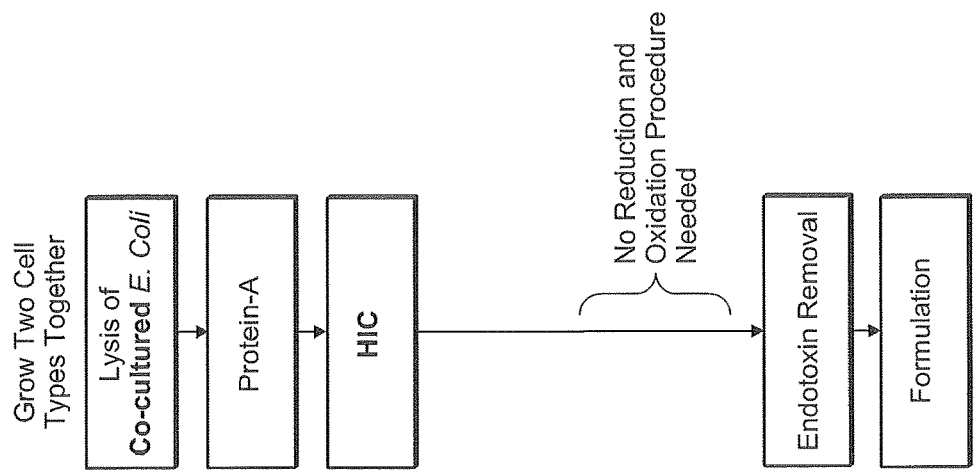
FIG. 8D is a flow chart of the co-culture process for the production of heteromultimeric proteins, e.g., bispecific antibodies.
Figure 8C:
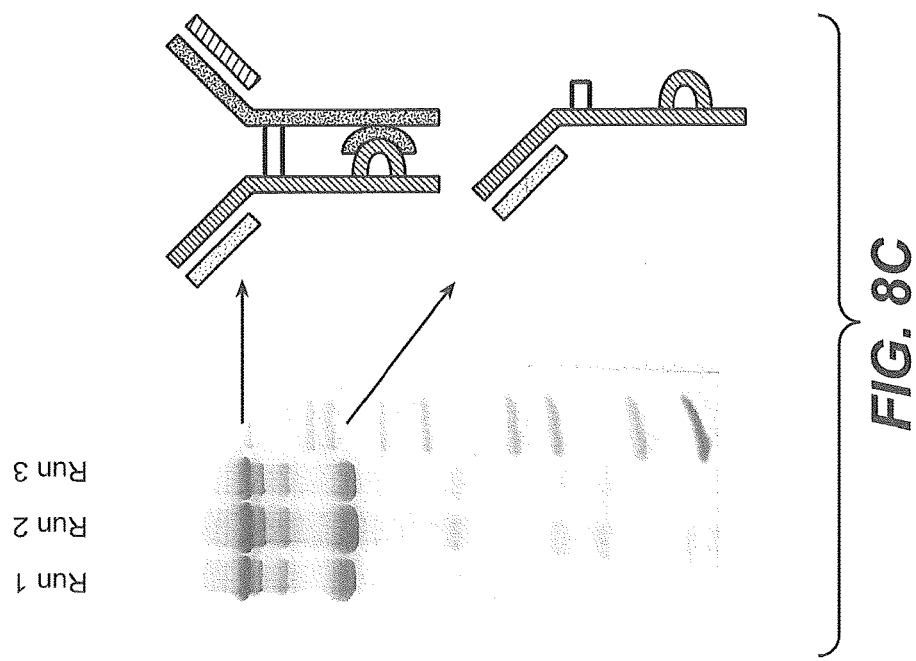
FIG. 8C is a photograph of a gel for three separate 10 liter fermentation runs of a 1:1 cell ratio of anti-EGFR and anti-c-Met. Each run produced as the main product the full-length bispecific indicating the reproducibility of the process.
Figure 8E:
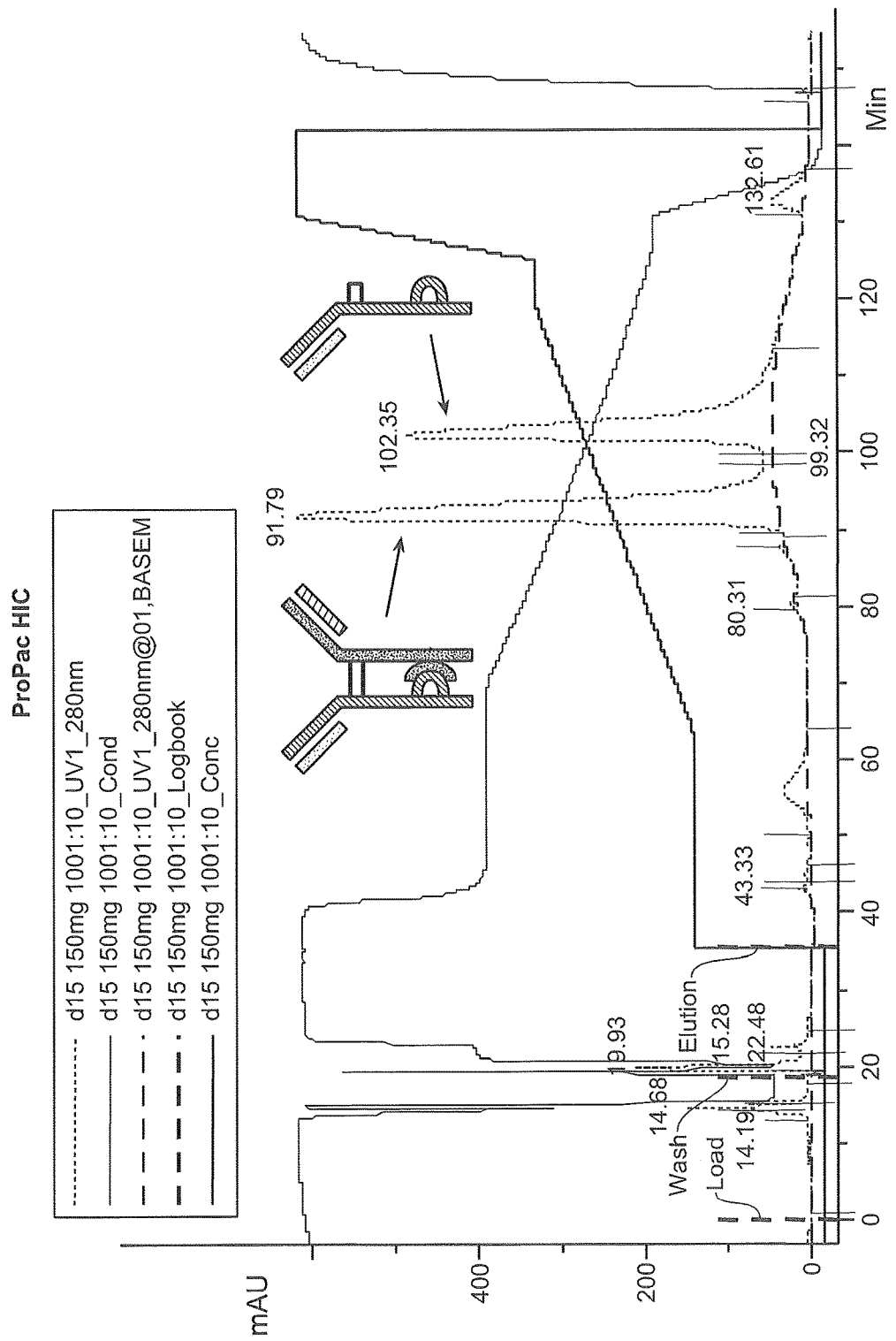
FIG. 8E is a chromatogram of the UV absorbance at 280 nm identified two significant peaks at retention times 91.79 and 102.35. Subsequent analysis by mass spectrometry indicated that the intact bispecific antibody was effectively separated from the excess half-antibody.
Figure 8F:
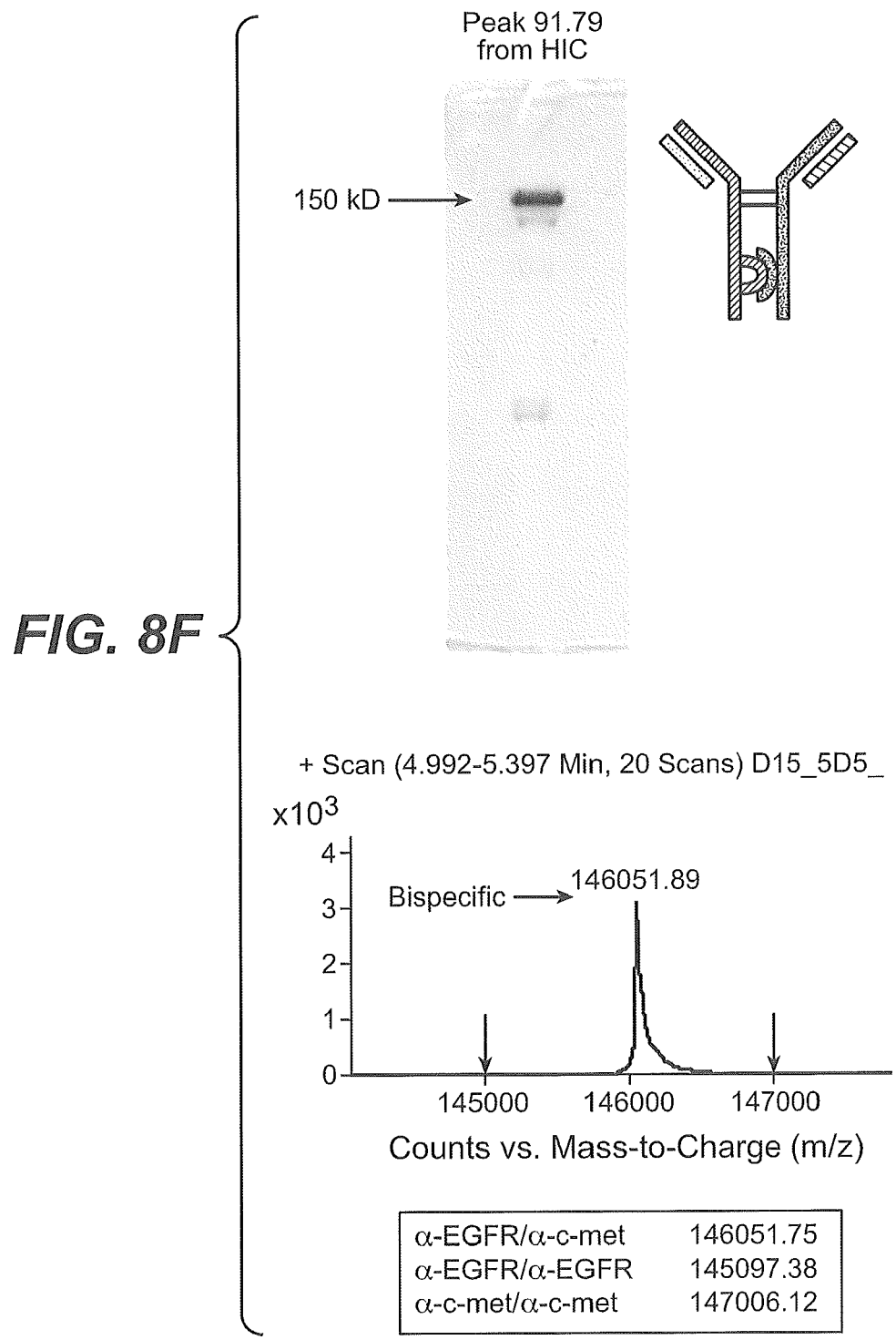
FIG. 8F shows the analysis of Peak 91.79 from FIG. 8E by SDS-PAGE and mass spectrometry. Decovolution of mass spectrometry data produced a single peak at 146,051.89 Daltons, which is in agreement with the expected mass of the bispecific antibody. Contaminating homodimeric species were not detected.
Figure 8G:
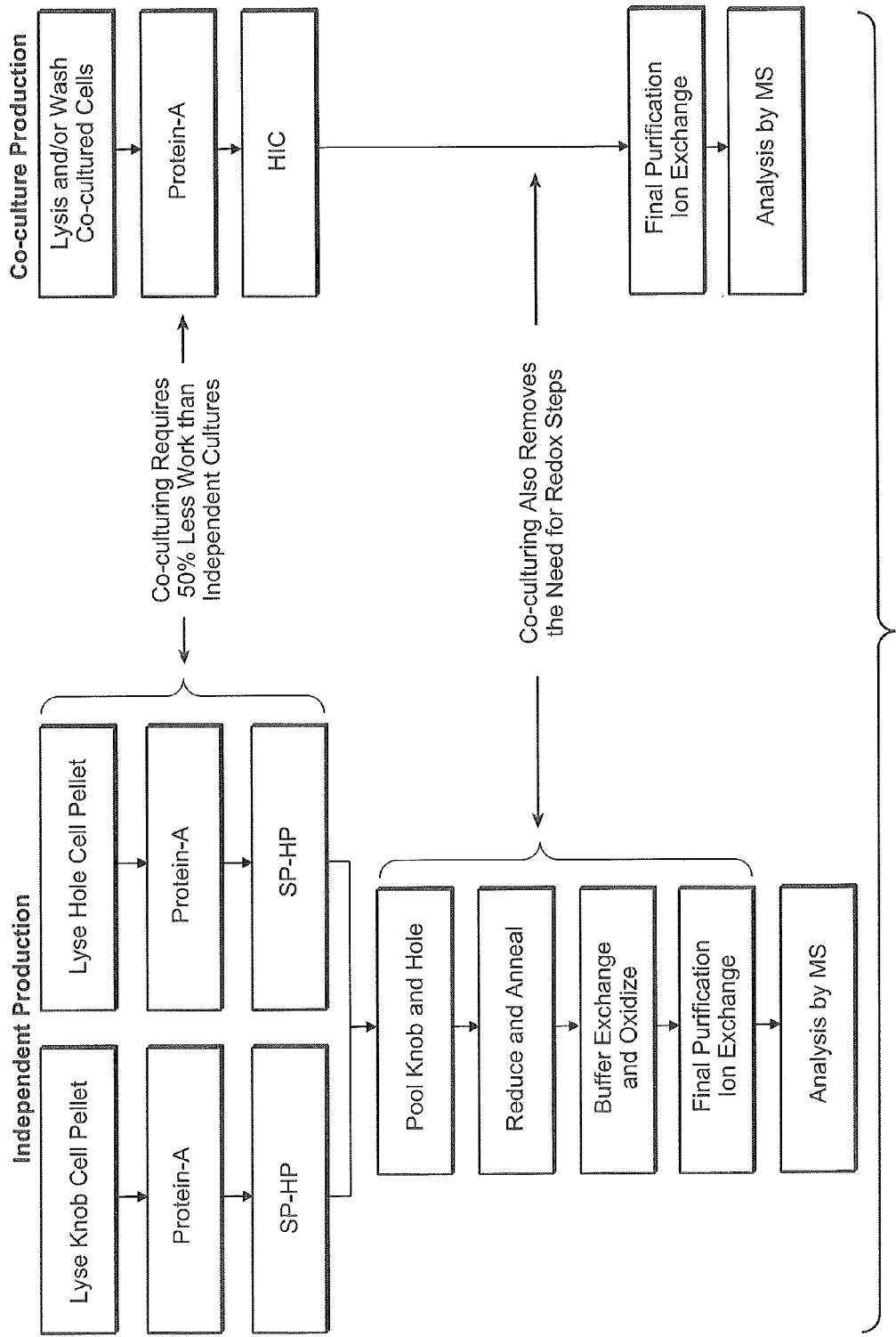
FIG. 8G is a comparison of the work flows for independent production and co-culture production of heteromultimeric proteins.

This observation led to the development of a simplified expression and purification scheme as shown in FIG. 8D. After protein A capture, the antibody was diluted 1:1 with a buffer containing 1.5 M ammonium sulfate and 25 mM sodium phosphate pH 6.5 and loaded onto a hydrophobic interaction column (HIC) Dionex Pro Pac HIC-10 4.6 mm×100 mm (Sunnyvale, Calif.). A gradient of 30-60% B, with the A buffer composed of 25 mM sodium phosphate, pH 6.95, and 1.5 M ammonium sulfate, and the B buffer composed of 25 mM sodium phosphate, pH 6.95, and 25 isopropyl alcohol. Proteins were separated with a 15 CV gradient. The protein separated into two major species, one containing the intact bispecific antibody and the other containing the excess anti-EGFR half-antibody. The results of the chromatographic separation are shown in FIG. 8E. The fractions containing the intact antibody were pooled and treated to remove any remaining contaminating endotoxin by adherence to an S-FF column in a 25 mM sodium acetate buffer at pH 5.0, washing with the same acetate buffer containing 0.1% Triton X114, and then removing the detergent by washing with the starting acetate buffer. The protein was eluted from the S-FF column using 25 mM Tris, pH 8.0, pooled, and analyzed by SDS-PAGE, mass spectrometry and LAL assays for endotoxin. The protein contained 0.076 EU/mg of endotoxin in the final preparation, indicating that it is suitable for in vivo applications. The final characterization is shown in FIG. 8F. The SDS-PAGE analysis shows a majority of the protein to be the final intact bispecific antibody, and the mass spec analysis shows the expected molecular weight for the bispecific antibody, and the lack of any contaminating species, in particular the homodimeric forms that could be present. The comparison of the modified procedure using coculturing compared to the procedure that requires annealing and redox chemistry is shown in FIG. 8G.

Method #5—Production of Knob Half-Antibody and Hole Half-Antibody in the Same Culture to Form Intact BsAb Using Differing Knob:Hole Ratios.

This example shows that host cells using similar expression constructs (differing only in the half-antibody to be expressed) do not outgrow each other and produce intact BsAb.

Experiments have demonstrated that controlling the ratio of either chain is easily done by adjusting the inoculation ratio prior to expansion and expression. The two strains do not outgrow one another.

To determine if the ratio of inoculation is preserved over the fermentation of a co-culture, an experiment was conducted to determine the amount of the knob or hole heavy chain that was present at the end of a 24 hour fermentation of co-cultures with different cell ratios. Cells harboring either the knob (anti-EGFR) or hole (anti-c-Met) plasmid were grown separately in LB-media (100 µg/ml carbenicillin) over night at 30° C. The starter culture was used to inoculate complete CRAP-media (100 µg/ml carbenicillin) with different ratios of overnight culture keeping the combined inoculation volume at 1:100 of the final culture. The ratios tested for anti-EGFR:anti-c-Met were 10:1, 5:1, 2:1, 1:1, 1:2, 1:5, and 1:10. After culturing for 24 hrs at 30° C. cell samples were obtained and analyzed by non-reduced SDS-PAGE (12% TrisGlycine) followed by Western blotting with Goat anti-Human IgG-Fc Antibody HRP conjugated (Bethyl Laboratories, Inc., Montgomery, Tex.). The heavy chains of the two species resolve by SDS-PAGE and the result is shown in FIG. 8B. The amount of each half-antibody correlates with the inoculation ratio of the co-culture, indicating that cells harboring plasmids encoding different half-antibodies do not outgrow each other in a co-culture.

Method #6—Production of Knob Half-Antibody and Hole Half-Antibody in the Same Culture to Form Intact BsAb—Membrane Permeabilization.

This example shows that membrane permeabilization releases the half-antibodies into the media and with the subsequent formation of an intact BsAb without the need for additional chemistry (e.g., redox or coupling).

It is known that mutations leading to the loss of lipoprotein synthesis alters the cell membrane of E. coli conferring leakiness of periplasmic proteins into the media and also renders E. coli hypersensitive to EDTA (Hirota, Y. et al. PNAS 74:1417-1420 (1977)). The release of expressed antibody from strain 65G4 (W3110 ΔfhuA ΔphoA ilvG+ Δprc spr43H1 ΔdegP ΔmanA lacI$^q$ ΔompT Δlpp) with and without addition of EDTA was compared. Cells expressing either a-IL-4 (hole) or α-IL-13 (knob) were co-cultured as described in Method #4 in a 1:1 ratio and grown in an incubator shaker at 200 rpm for 20 hrs at 30° C. At the end of the incubation the culture was split into three equal aliquots. One sample served as a control with no EDTA added. To the other two samples EDTA, pH 8.0, was added to 10 mM final concentration. Incubation was continued for all samples for 30 minutes, after which one of the EDTA treated samples had MgCl$_2$ added to 20 mM final concentration. All samples were incubated for an additional 30 minutes in the incubator shaker before removing cells by centrifugation (9200×g, 20 minutes, 4° C.) and the supernatant filtered through a GF/F filter (Whatman, Piscataway, N.J.) and 0.2 µm PES filter (Nalgene, Rochester, N.Y.). DNaseI, bovine pancreas (Sigma, St. Louis, Mo.) can be added to 4 mg/l to improve filtration.

The filtered supernatant was then directly loaded over a 1 mL Protein A MabSelect SURE HiTrap column (GE Healthcare) as described previously. The captured protein was eluted with acetic acid as described above and the peak recovery of the protein can be seen in FIG. 9A. The results show that the total UV absorbance increases in the EDTA treated samples. This absorbance is intact bispecific antibody and excess half-antibody. See FIGS. 9B and 9C.

In a separate experiment the anti-IL-4 and anti-IL-13 half-antibodies were expressed separately or as a 1:1 co-culture of 65G4 cells. Cells were cultured as described above (Method #4) with the exception of supplementing the complete CRAP media with Silicone Antifoam (Fluka, Buchs, Switzerland) to 0.02% (v/v). After culturing the cells for 24 hrs, 30° C., 200 rpm in an incubator shaker, EDTA, pH 8.0, was added to 10 mM final concentration and incubation continued for one hour before adding MgCl$_2$ to 20 mM. Cells were harvested by centrifugation (6750×g, 10 minutes, 4° C.), the supernatant filtered (0.2µPES, Nalgene, Rochester, N.Y.) and antibodies were captured by protein A as described above and analyzed by SDS-PAGE and mass spectrometry. The results shown in FIG. 9D indicate that intact bispecific antibody formation is observed only in the presence of both halves of the bispecific. Additionally, the majority of the anti-IL-13 antibody was incorporated into the bispecific antibody without any additional redox chemistry as mass spec analysis indicated that the 75 kD protein band was mostly the anti-IL-4 half-antibody. The protein A purified bispecific antibody was diluted 1:1 with ammonium sulfate buffer and further purified with a 7.5 mm×150 mm ProPac HIC-10 column (Dionex, Sunnyvale, Calif.) using the same procedure as described in Example 3. The intact bispecific antibody was found to elute at a retention time of 99.68. This peak was pooled and analyzed by SDS-PAGE in non-reducing conditions and found to be nearly entirely composed of the intact antibody species. To confirm that this protein was a pure heterodimeric bispecific molecule, we analyzed the protein by ESI-TOF LC/MS. About 10 micrograms of the bispecific antibody were injected onto a PLRP-S 300 A 3 micrometer 50×2.1 mm reverse phase column (Polymer Laboratories) and separated by a 4.3 minute gradient of 34-45% 0.05% TFA and acetonitrile using an Agilent 1200 Series HPLC and a flow rate of 0.5 mL/min and a column heater at 80° C. Protein eluting from the LC was analyzed by an Agilent 6210 TOF. A single peak containing protein was observed, and this peak was deconvoluted using Agilent Mass Hunter software version B.02.00 using a mass range of 50,000-160,000, 1.0 Da step, 30.0 S/N threshold, average mass of 90, an unlimited mass range and an isotope width set to automatic. The majority of the signal representing the expected mass of the bispecific molecule. The mass for the intact heterodimeric bispecific calculated from the amino acid sequence is 144,044 which is within 1-2 Daltons of the measured mass, whereas the calculated masses of the possible homodimeric proteins are 144,954.6 for anti-IL-4 and 145, 133.4 for anti-IL-13.

Figures 1, 9E:
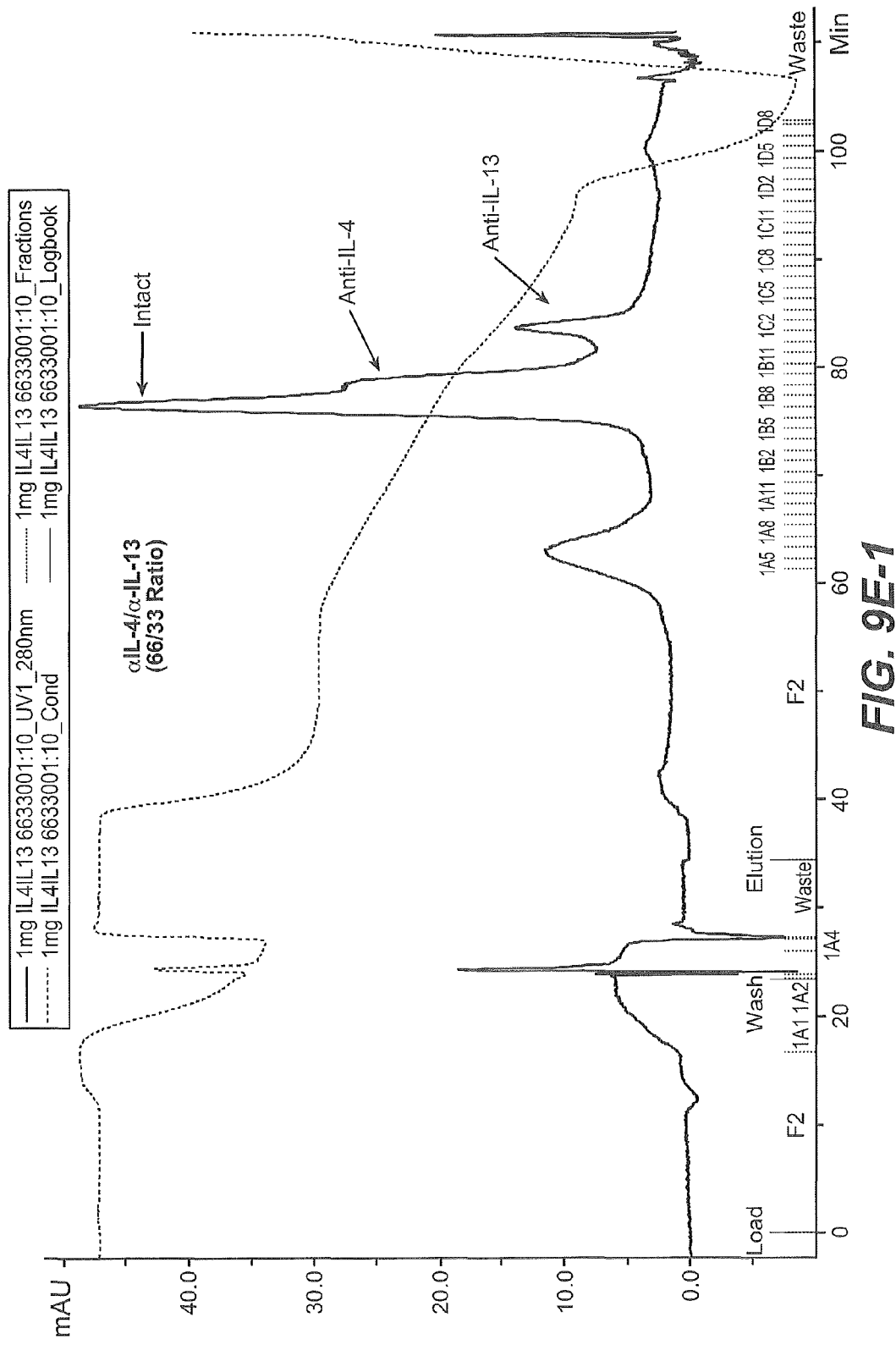
Figures 2, 9E:
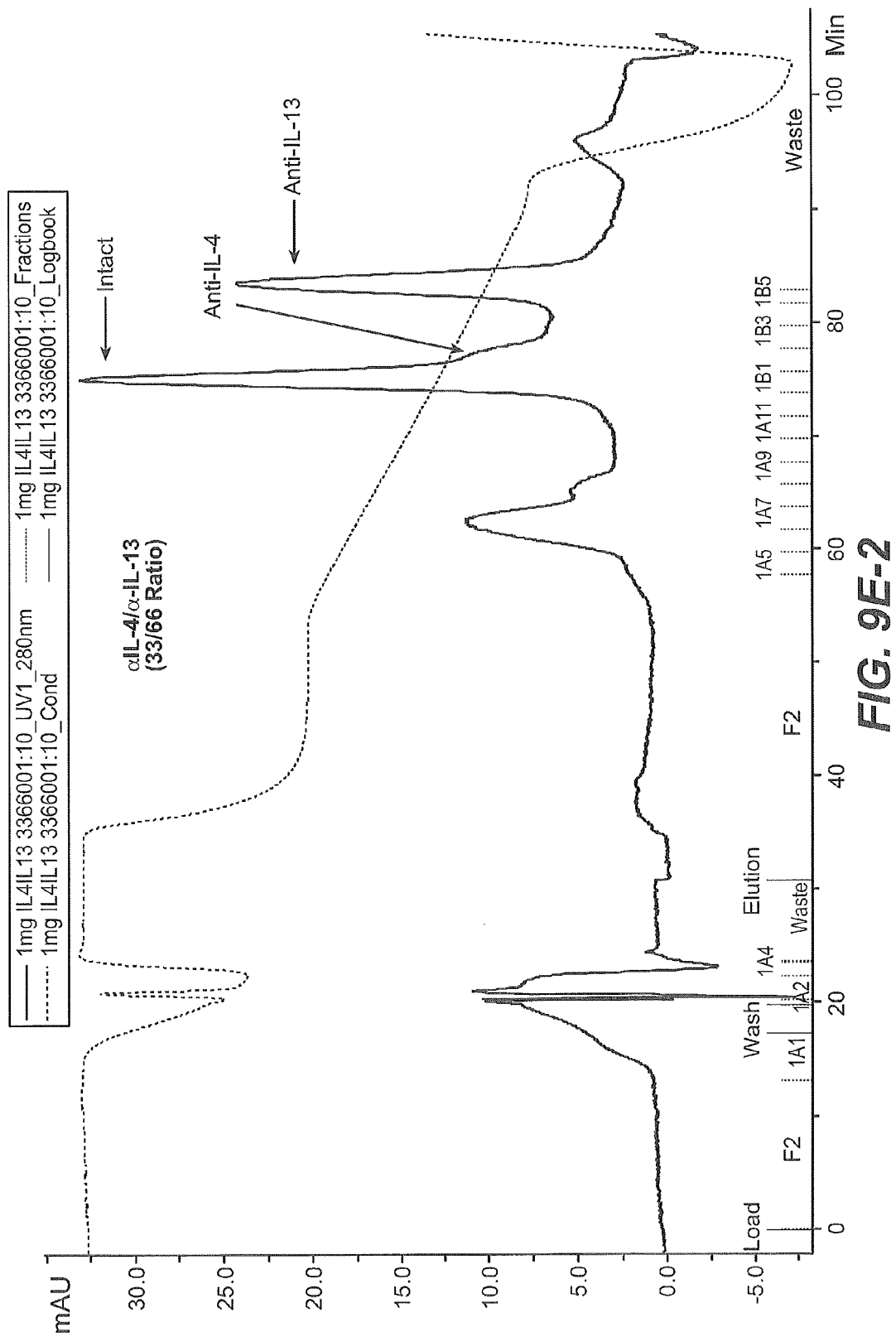
Figure 9F:
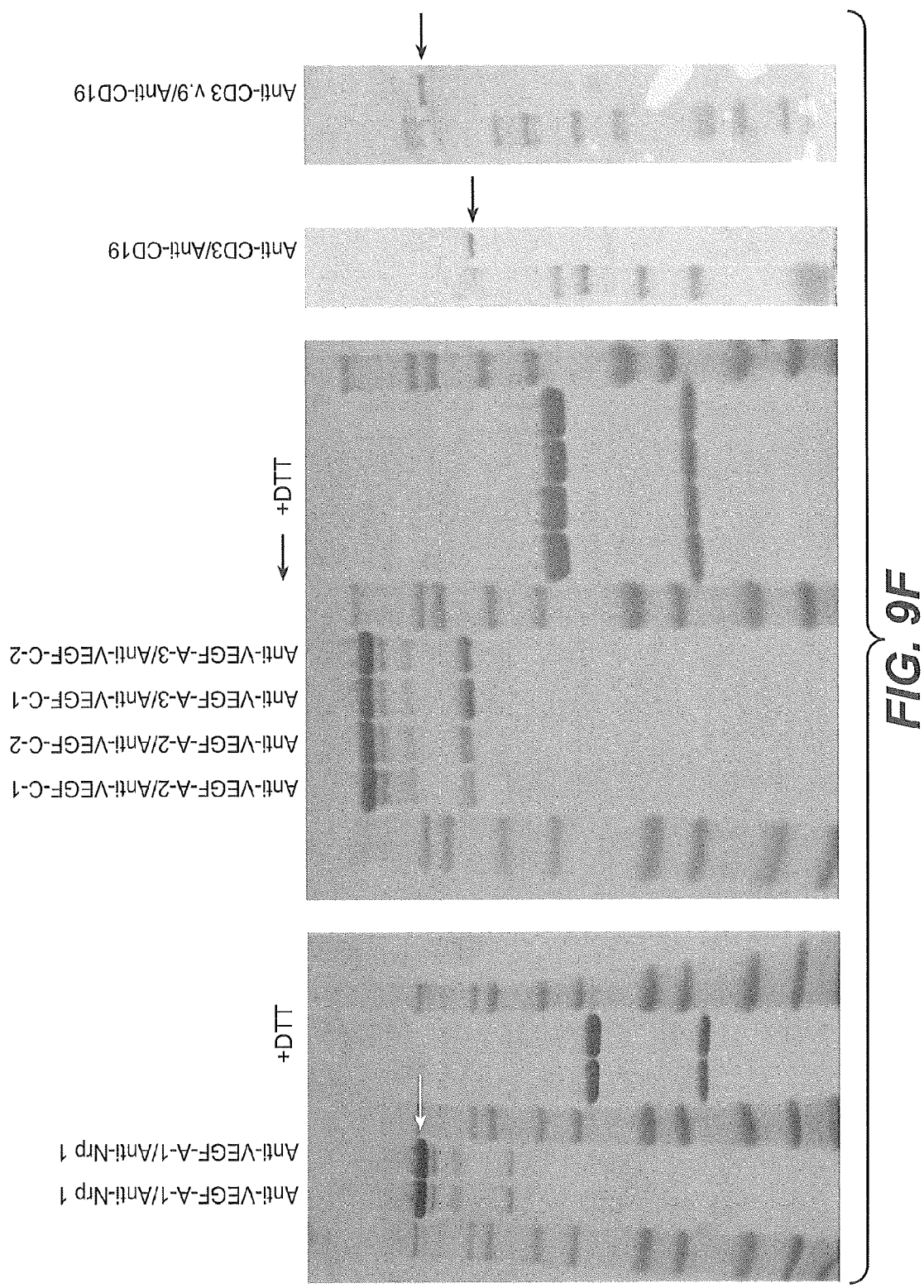
FIG. 9F is a panel of four photographs showing the SDS-PAGE analysis under reducing and non-reducing conditions of eight different bispecific antibodies produced by the co-culture process described herein The non-reducing gels for the anti-CD3/anti-CD19 heteromultimeric proteins is not shown. Arrows indicate the intact bispecific antibodies.
Figure 10:
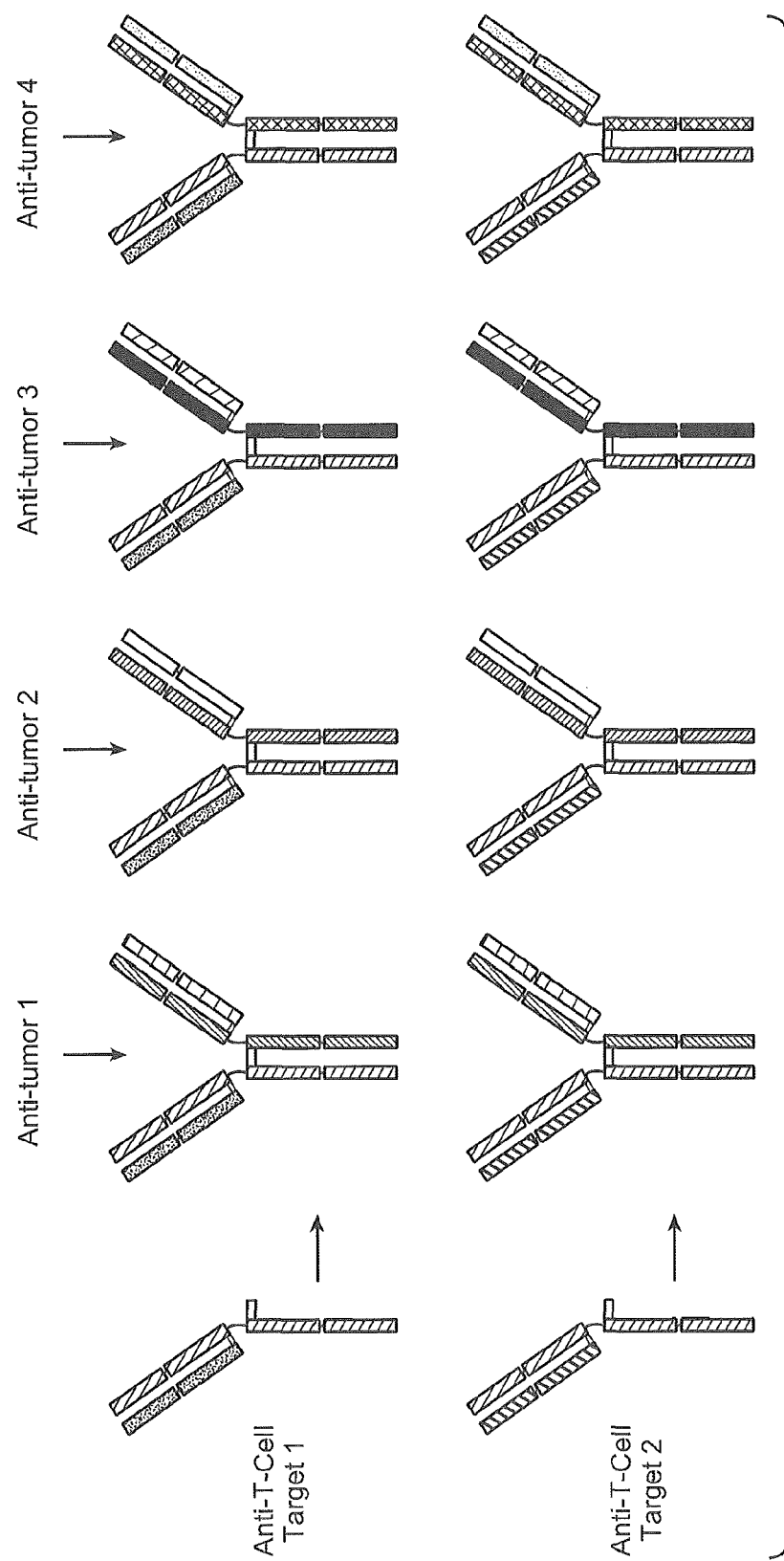
FIG. 10 is a schematic of a matrix approach to screening heteromultimeric proteins.

We tested if different inoculation ratios would again persist throughout the culture for this set of antibodies and also in the context of the Ipp deletion of 65G4. Seed cultures with either anti-IL-4 (hole) or anti-IL-13 (knob) of equal $OD_{600}$ were used to inoculate 500 ml CRAP media at 2:1 and 1:2 ratios, cultured and permeabilized at the end of the fermentation as described before (see Method #6). The two different media preparations were purified by Protein A capture followed by HIC separation as described above, except that the pH of the HIC A and B buffers were lowered to 6.5. The results of the two different starting culture ratios are shown in FIG. 9E. It is observed that the majority of the protein is the intact bispecific antibody. The other peaks were characterized by mass spectrometry and labeled on the FIG. 9E. The anti-IL-13 half-antibody is slightly detected, and a significant amount more of anti-IL-4 is seen. In the 33/66 ratio of anti-IL-4 to anti-IL-13, there is more anti-IL-13 observed with a slight amount of anti-IL-4 remaining. Here we see that the ratio of inoculation is maintained throughout the culture and that the optimization of the process could be achieved by balancing the ratios of expressed antibody halves through manipulating the started culture ratios.

We have continued to test this process of co-culture expression in delta-Ipp cells on a number of different antibody variants. We show in FIG. 9F the final purified proteins after formulation post HIC chromatography of a few exemplary half-antibodies.

Example 4

Heteromultimeric Protein Libraries

This example illustrates the construction of a heteromultimeric protein library.

Certain methods that may be used to screen mixtures of bispecific antibodies or to rapidly generate large arrays of bispecific antibodies using the methods described.

Method #7

In some cases the choice of bispecific antibody is not known, but could be the result of the combination of many different half-antibodies. Alternatively, a specific target combination may be desired, e.g., anti-IL-4/anti-IL-13 but there are a number of candidate half-antibodies to choose from. Finding the specific half-antibody combination that yields the best binding or efficacy may be accomplished by combining the half-antibodies in a matrix format, one can produce many bispecific antibody variants rapidly. For this experiment, one antibody such as anti-CD3 can be produced at about 10-fold (or greater) excess over the amount of antibody needed for screening. This molecule can then be annealed and oxidized using the procedure described in Example #1. About one tenth of the total amount of the first antibody can be used to combine with an equal amount of about 10 half-antibodies targeting different antigens (such as anti-CD19, anti-CD20, etc.) as diagramed in FIG. 10. If an additional primary half-antibody is needed to combine with the second half-antibody repertoire, this can be done to yield a set of screening molecules.

In a second modification of the method, the primary antibody (such anti-CD3) can be grown as a co-culture using "normal" E. coli host cells or with a mutant strain having a non-functional lipoprotein phenotype. This half-antibody can then be systematically added to each of the variable half-antibodies producing an array of bispecific molecules all containing the primary targeting half-antibody.

Method #8

The primary half-antibody can be combined with a host of alternative partnering half-antibodies in a manner that consists of producing this half-antibody in sufficient quantity to combine with all of the other antibody half-antibodies combined. A bulk annealing can then be performed in a single reaction such that the primary half-antibody is either the knob or the hole version of the heavy chain and the set of secondary targeting half-antibodies are the complimentary mutant. Here, a complex mixture of antibodies can be produced that may be useful treating disease as a combination.

Alternatively, a co-culture approach using the methods described in the above Examples can be used to produce a complex mixture of bispecific antibodies with a set primary half-antibody and a variable secondary half-antibody. Such a mixture could then be isolated in bulk and used as a screening material such that a positive result in the pool of bispecific variants could be later deconvoluted to determine the active bispecific antibody species, or the combined mixture could be used as a more effective therapeutic mixture.

Example 5

In Vitro Activity

This example that the bispecific antibodies described herein possess activity in in vitro systems. Two cell lines were employed in this Example 5 and in Example 6, below. In these experiments KP4, a pancreatic ductal carcinoma cell line, and A431, an epidermoid carcinoma cell line, are both strongly driven by Met or EGFR, respectively, therefore these are good cell lines and tumor xenografts to explore efficacy of bsAb against each target independently.

The KP4 cell line was obtained from the Riken BioResource Center Cell Bank (Cell line #: RCB1005; 3-1-1 Koyadai, Tuskuba-shi, Ibaraki 305-0074 Japan). The A431 cell line (CRL-1555) was obtained from the American Type Culture Collection (ATCC, Manassas, Va.).

Cancer cells, A431, were washed once with PBS, resuspended in serum-free medium, counted, and then added to 96-well plates (2500 cells/well). Cells were then treated with human HGF (0.5 nM) and TGFα (0.05 nM) alone or with a dose range of either (1) anti-EGFR, (2) Anti-c-met antibody ("one-armed" c-met), (3) the combination of anti-EGFR and Anti-c-met antibody or (4) the bispecific anti-EGFR/anti-c-met antibody. Three day AlamarBlue™ assays were performed according to manufacturer's recommendations (BioSource International; Camarillo, Calif.). $IC_{50}$ values were determined by nonlinear regression analysis with a four-parameter model (KaleidaGraph ver. 3.6, Synergy Software; Reading, Pa.).

In the KP4 cell assay which is Met dependent in vitro and in vivo, growth stimulated by treatment with TGF-alpha and HGF can be inhibited by Anti-c-met antibody, the combination of Anti-c-met antibody and anti-EGFR, and the bispecific antibody. Treatment with anti-EGFR shows limited activity as a single agent in these cells. There was, however, more potent inhibition by the bispecific antibody in KP4 cells than anti-c-met alone or anti-c-met plus anti-EGFR Abs added separately. In A431 cells, which are primarily driven by EGFR, neither the anti-EGFR antibody nor the anti-c-met antibody alone were able to significantly inhibit cell proliferation. The combination of both molecules did show some inhibition of cell proliferation, however, the bispecific antibody exhibited greater activity at the same concentrations. Also, the cells exhibited apoptosis in addition to anti-proliferation.

Figure 11:
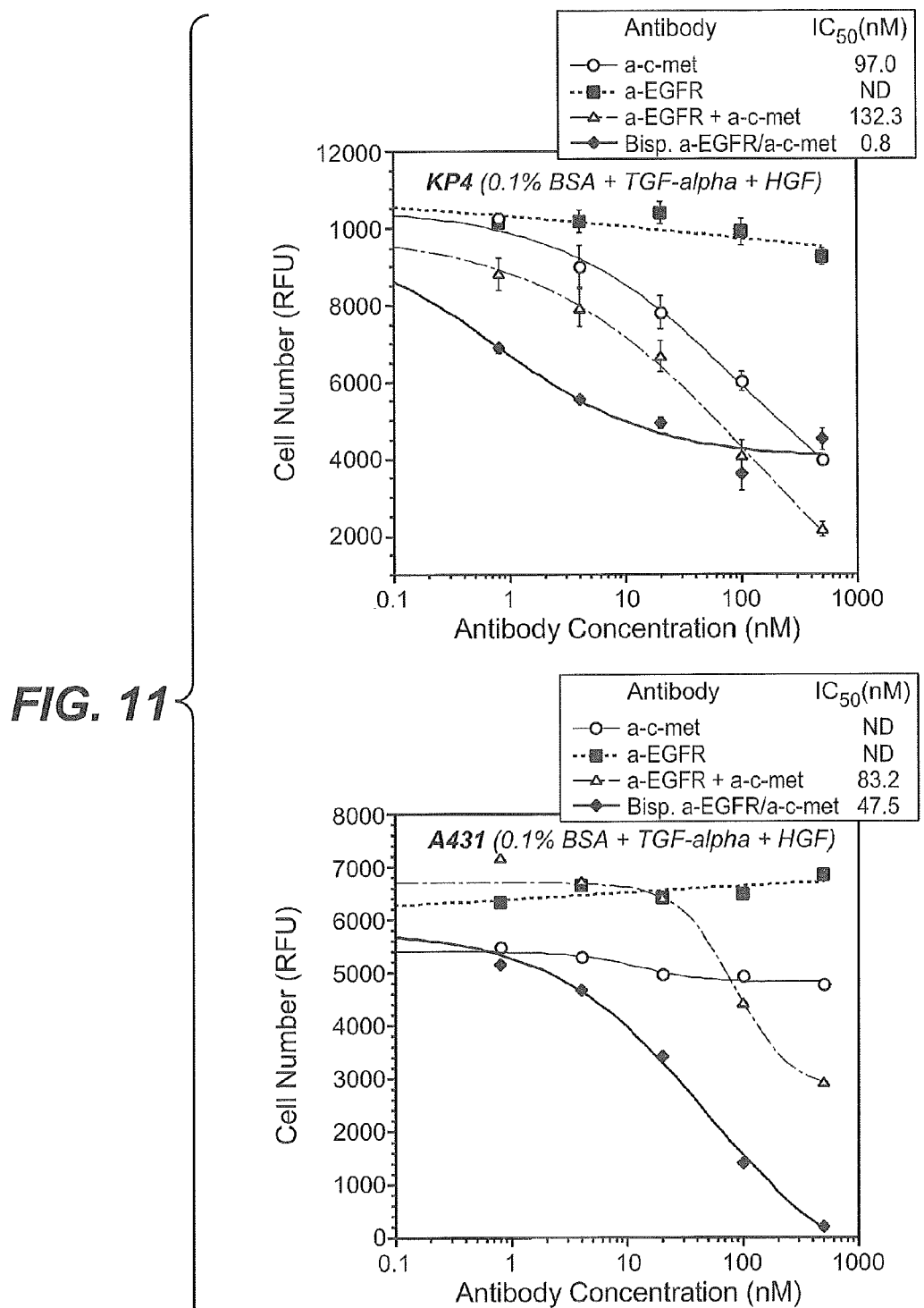
FIG. 11 shows two graphs for in vitro activity of bispecific antibodies produced using the methods described herein.

In these assays the bispecific antibody showed improved performance relative to the other antibodies alone or the combination of anti-Met and anti-EGFR antibodies added separately. These data suggest that it is the arrangement of anti-Met and anti-EGFR antibodies together on one antibody that makes the bispecific superior. The results are shown in FIG. 11.

Example 6

In Vivo Activity

This example demonstrates that the bispecific antibodies described herein possess activity in in vivo models.

Female nude mice that were 6-8 weeks old and weighed 22-30 g were obtained from Charles River Laboratories, Inc. (Hollister, Calif.). The mice were housed at Genentech in standard rodent micro-isolator cages and were acclimated to study conditions for at least 3 days before tumor cell implantation. Only animals that appeared to be healthy and that were free of obvious abnormalities were used for the study. All experimental procedures conformed to the guiding principles of the American Physiology Society and were approved by Genentech's Institutional Animal Care and Use Committee. Mice were injected subcutaneously with either human KP4 pancreatic cancer cells (5 million cells in Hank's Balanced Salt Solution (HBSS) plus Matrigel (BD Biosciences) per mouse) or human A431 epidermoid carcinoma cells (5 million cells in HBSS plus Matrigel/mouse). When tumors reached ~150 mm$^3$, mice were randomized and treated with vehicle or the bispecific EGFR/c-met (bsEGFR/c-met) (50 mg/kg IP 1×/week) for 2 weeks.

Tumor volumes were measured in two dimensions (length and width) using Ultra Cal-IV calipers (Model 54-10-111; Fred V. Fowler Co.; Newton, Mass.) and analyzed using Excel, version 11.2 (Microsoft Corporation; Redmond Wash.). Tumor inhibition graphs were plotted using Kaleida-Graph, version 3.6 (Synergy Software; Reading, Pa.). The tumor volume was calculated with the following formula:

Tumor size(mm$^3$)=(longer measurement×shorter measurement$^2$)×0.5

The data was analyzed by the mixed modeling approach described below. Here, a strict average and standard deviation are not calculated. Rather than provide standard deviations to account for the variability, confidence intervals are used. These are reported in the table as the upper and lower limits in the parenthesis next to AUC/day % TGI. Animal body weights were measured using an Adventura Pro AV812 scale (Ohaus Corporation; Pine Brook, N.J.). Graphs were generated using KaleidaGraph, version 3.6. Percent weight change was calculated using the following formula:

Group percent weight change=(new weight−initial weight)/initial weight)×100

To appropriately analyze the repeated measurement of tumor volumes from the same animals over time, a mixed modeling approach was used (Pinheiro et al., Linear and Nonlinear Mixed Effects Models. (2008) R package version 3.1-89). This approach addresses both repeated measurements and modest dropouts due to any non-treatment-related deaths of animals before the study end.

Cubic regression splines were used to fit a non-linear profile to the time courses of log$_2$ tumor volume at each dose level. These non-linear profiles were then related to dose within the mixed model. Tumor growth inhibition as a percentage of vehicle (% TGI) was calculated as the percentage of the area under the fitted curve (AUC) for the respective dose group per day in relation to the vehicle, using the following formula:

% TGI=100×(1−AUC$_{dose}$/AUC$_{veh}$)

To determine the uncertainty intervals (UIs) for % TGI, the fitted curve and the fitted covariance matrix were used to generate a random sample as an approximation to the distribution of % TGI. The random sample was composed of 1000 simulated realizations of the fitted-mixed model, where the % TGI has been recalculated for each realization. The reported UIs were the values for which 95% of the time, the recalculated values of % TGI would fall in this region given the fitted model. The 2.5 and 97.5 percentiles of the simulated distribution were used as the upper and lower UIs.

Plotting was performed and generated using R, version 2.8.1 (R Development Core Team 2008; R Foundation for Statistical Computing; Vienna, Austria) and Excel, version 12.0.1 (Microsoft Corporation). Data were analyzed using R, version 2.8.1, and the mixed models were fit within R using the nlme package, version 3.1-89 (Pinheiro et al., 2008).

Figure 12:
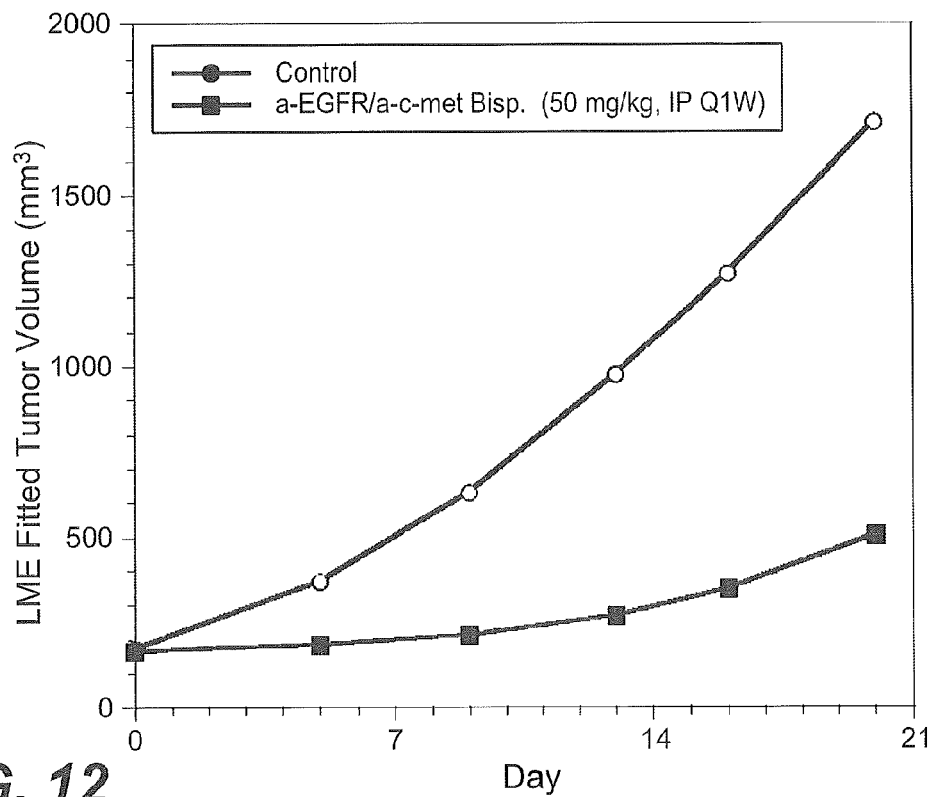
FIG. 12 is a graph showing that the anti-EGFR/anti-c-met bispecific possesses anti-tumor activity in a KP4 pancreatic xenograft in vivo model.
Figure 13:
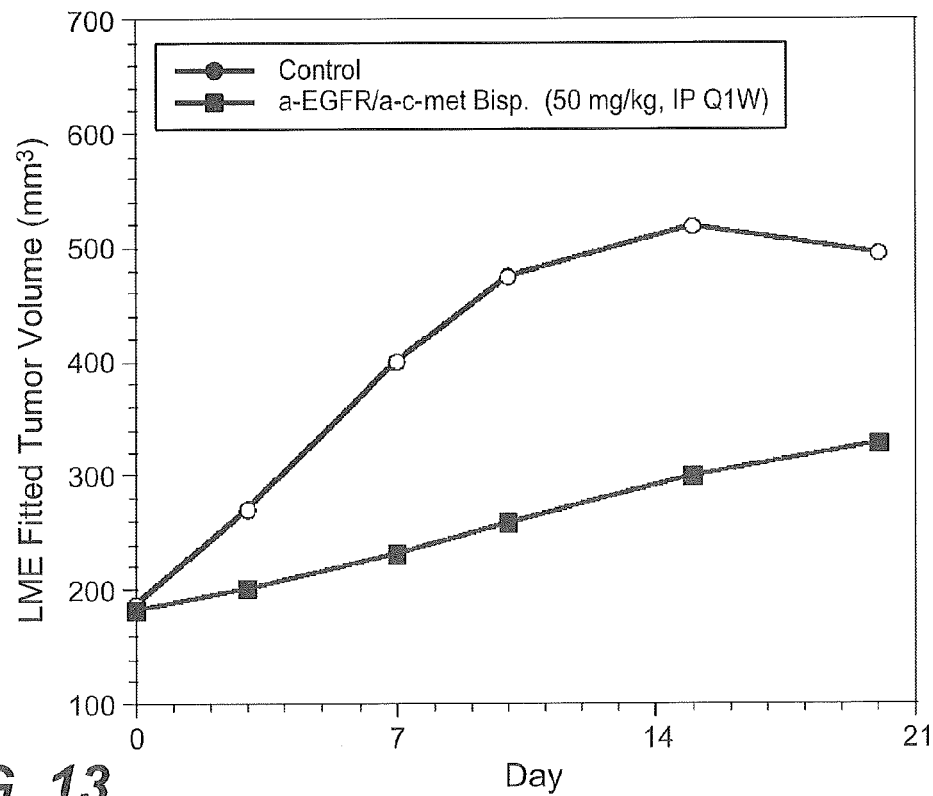
FIG. 13 is a graph showing that the anti-EGFR/anti-c-met bispecific possesses anti-tumor activity in an A431 epidermoid carcinoma xenograft in vivo model.
Figure 14A:
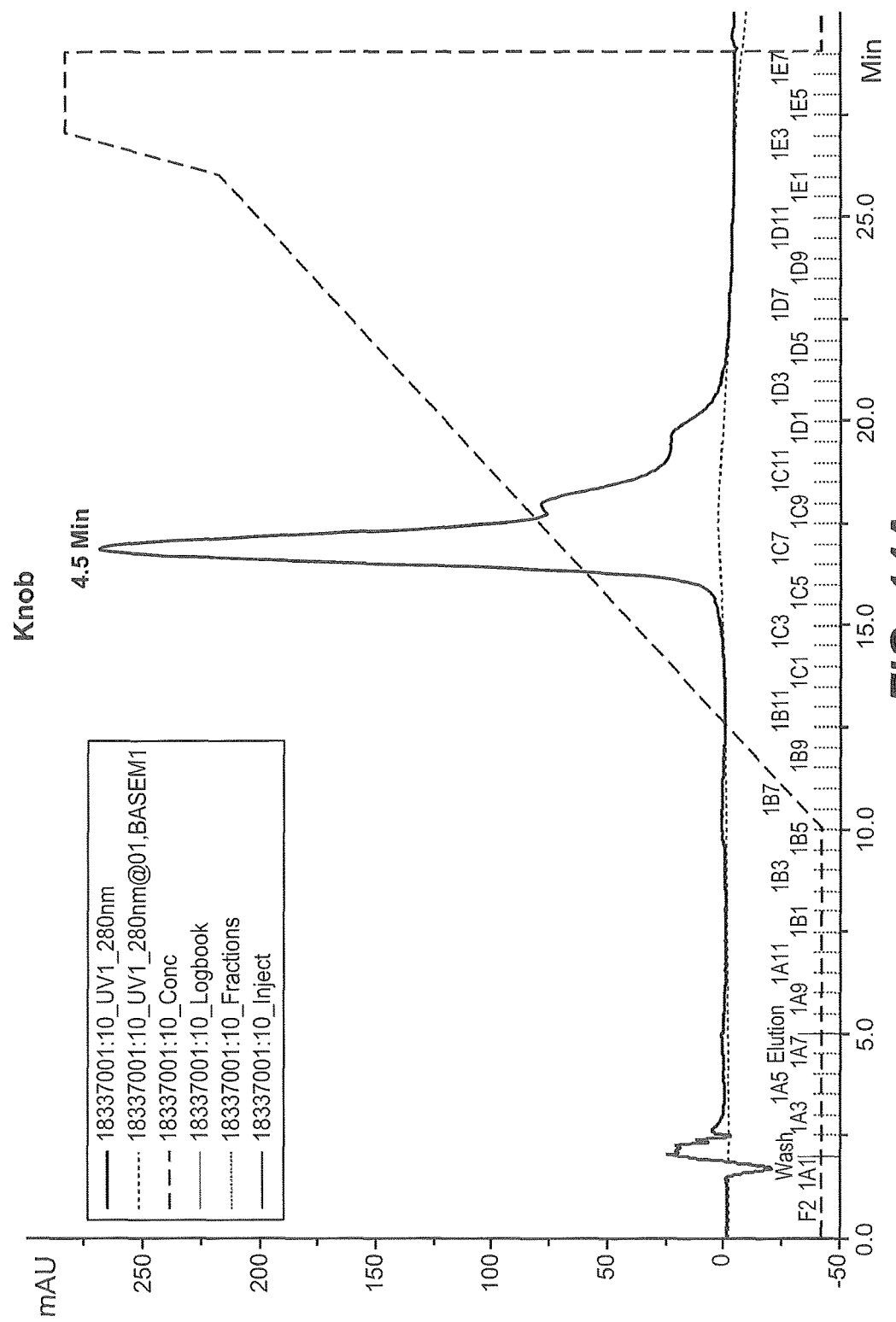
FIG. 14 shows the HIC of A) knob pre-assembly B) hole pre-assembly C) bispecific post assembly.
FIG. 14D is a gel of each arm pre-assembly
Figure 14B:
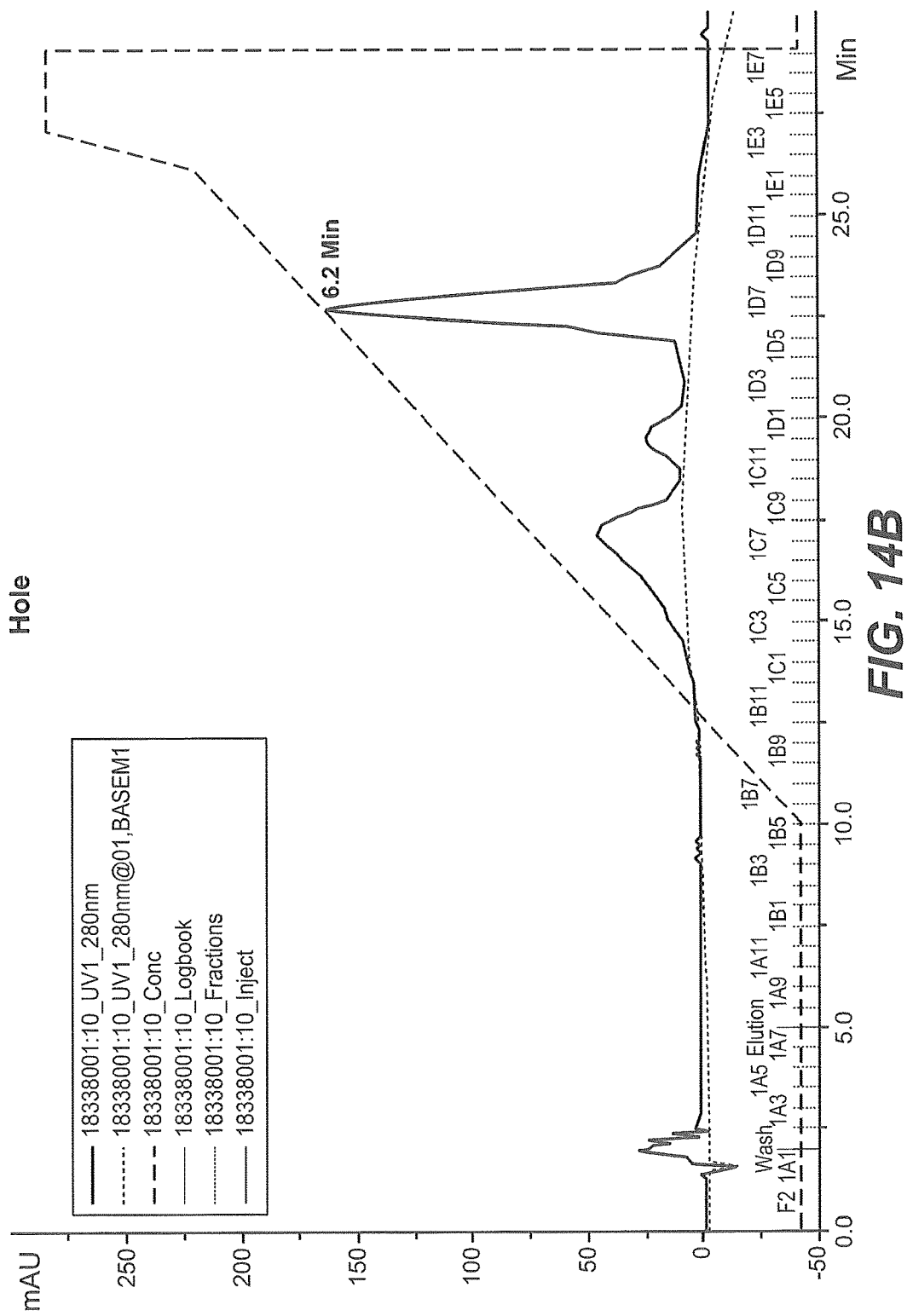
Figure 14C:
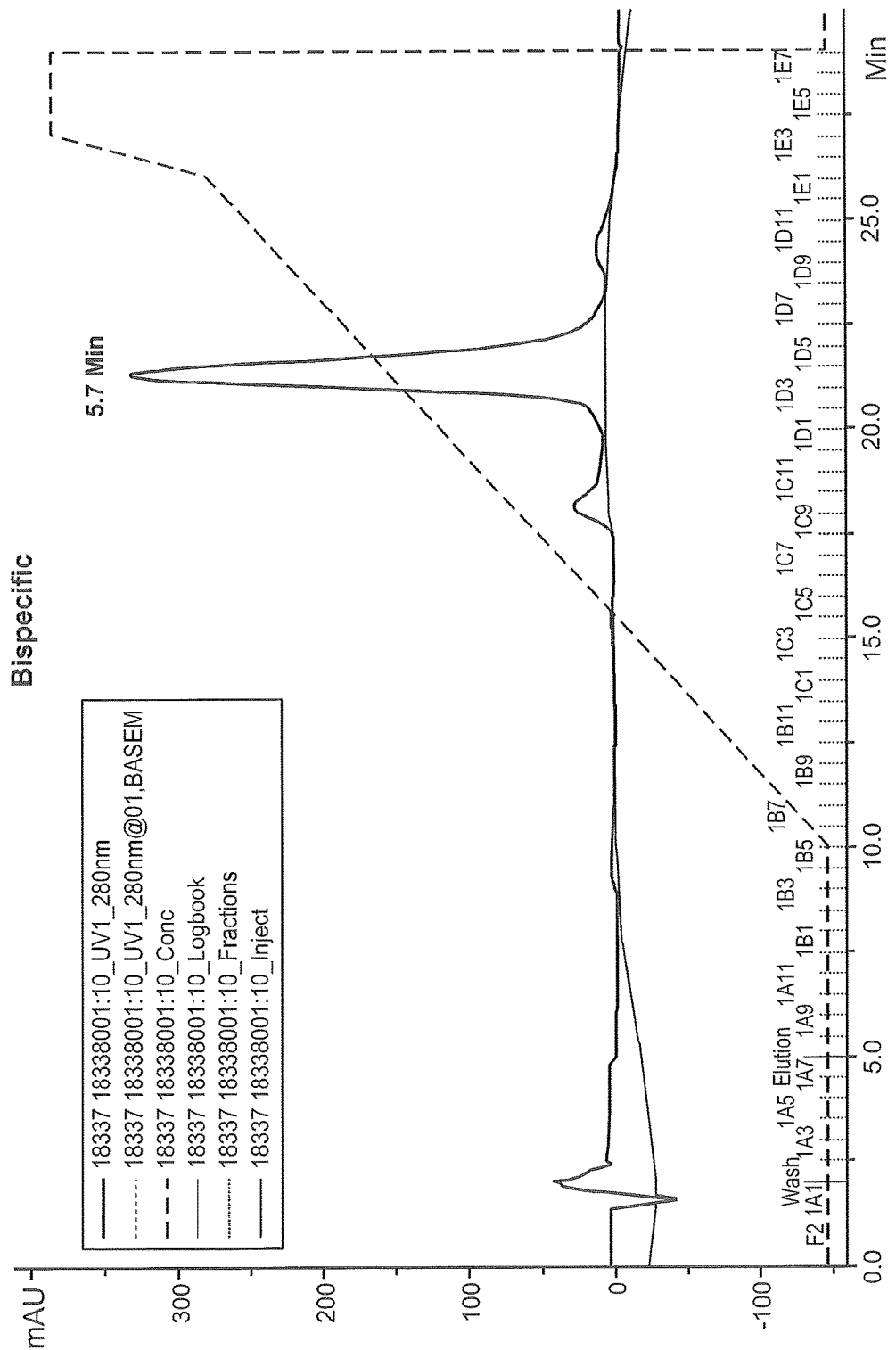
Figure 14D:
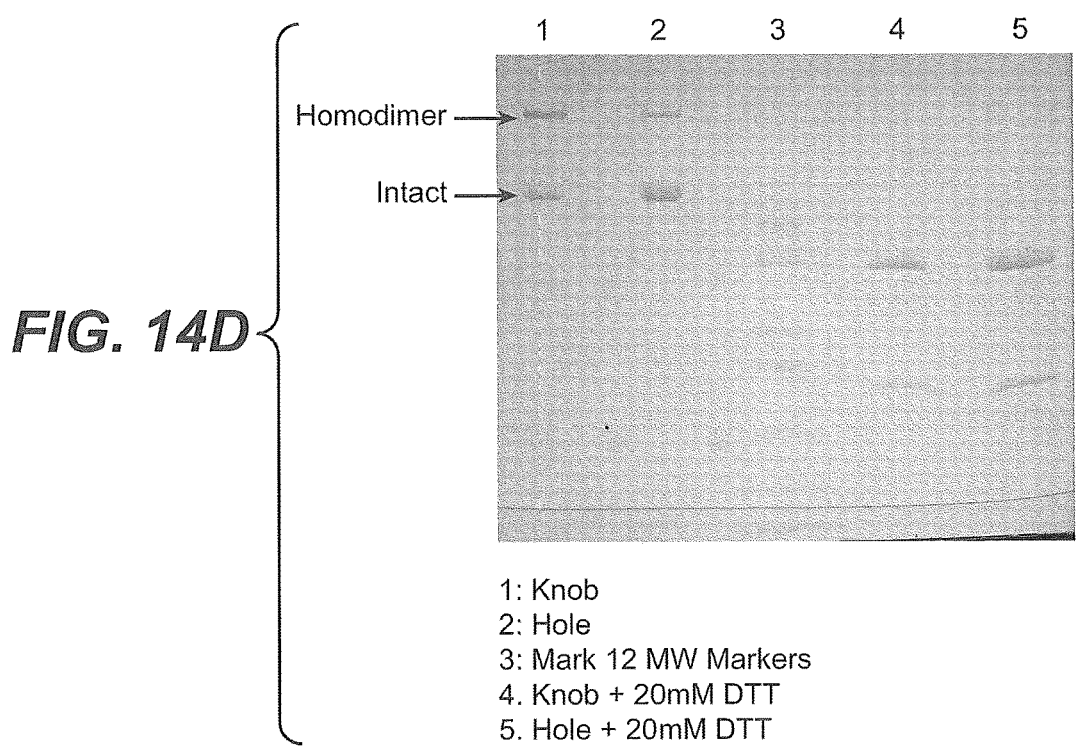
Figure 15:
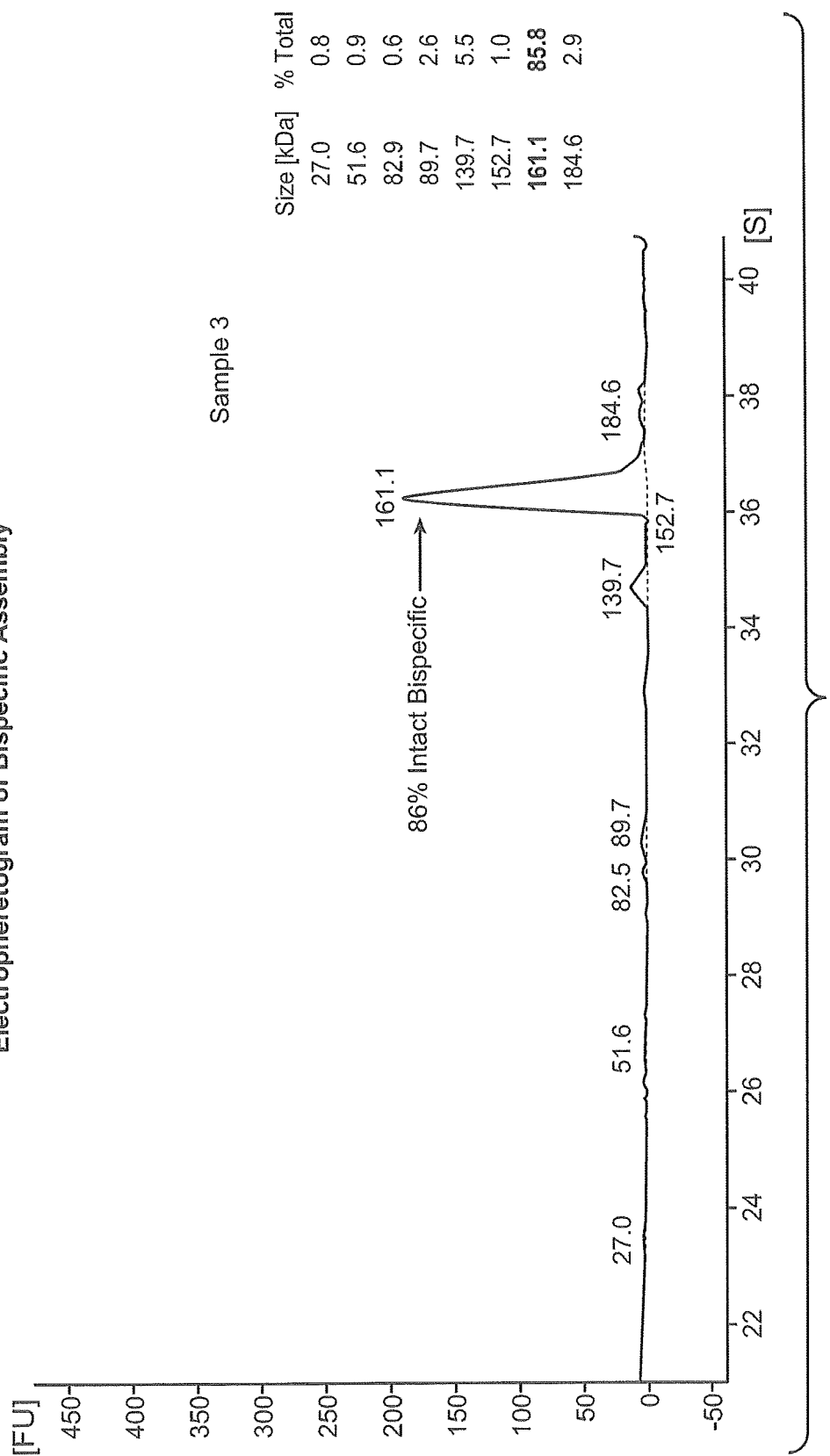
FIG. 15 shows an electrophoretogram of assembled material indicating that 86% of the material is fully oxidized.
Figure 16A:
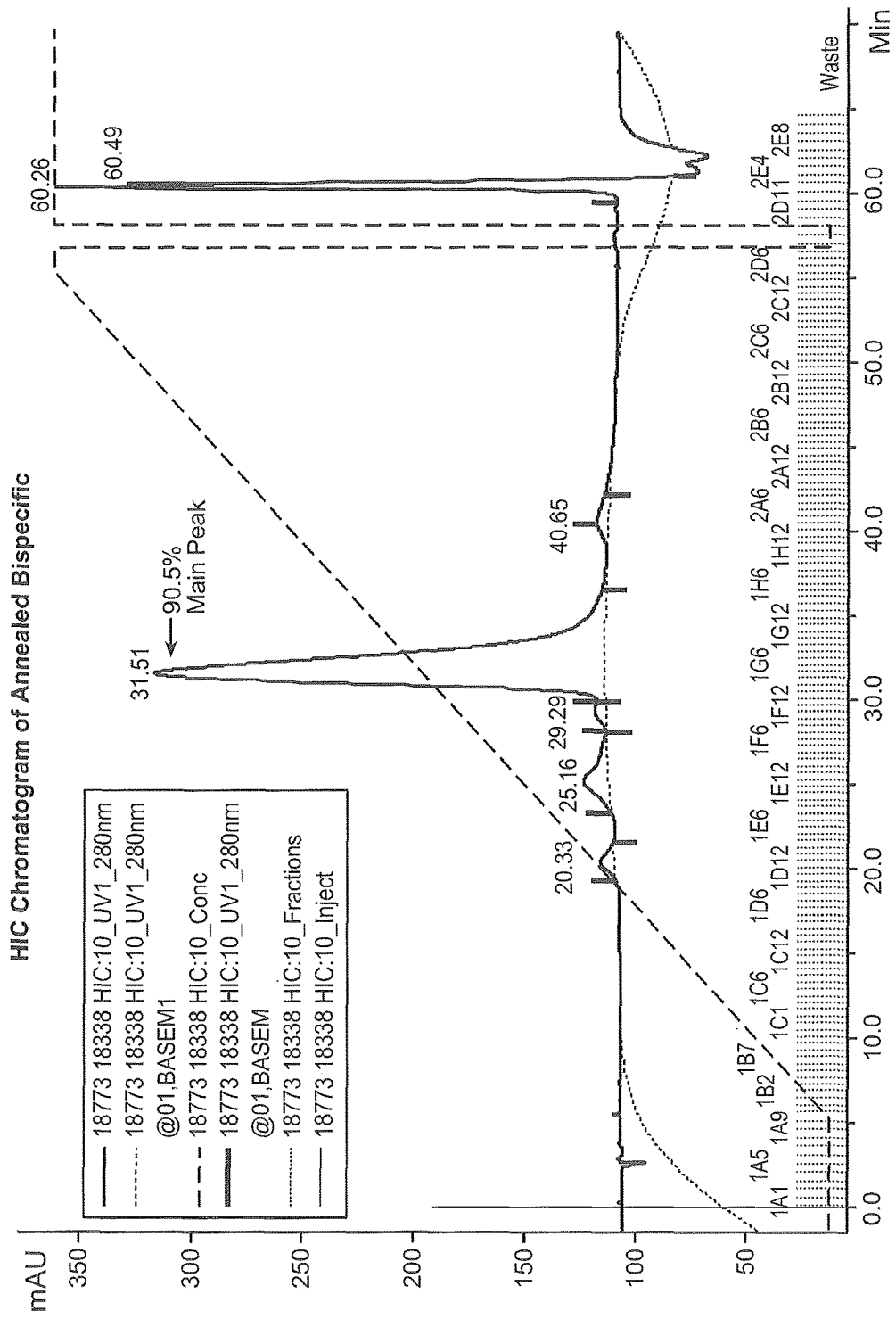
FIG. 16: Characterization of assembled bispecific A) HIC chromatogram of annealed bispecific indicates that the material is >90.5 percent bispecific B) gel of purified material C) mass spectronomy deconvolution of final sample, and D) table of theoretical masses.
Figure 16B:
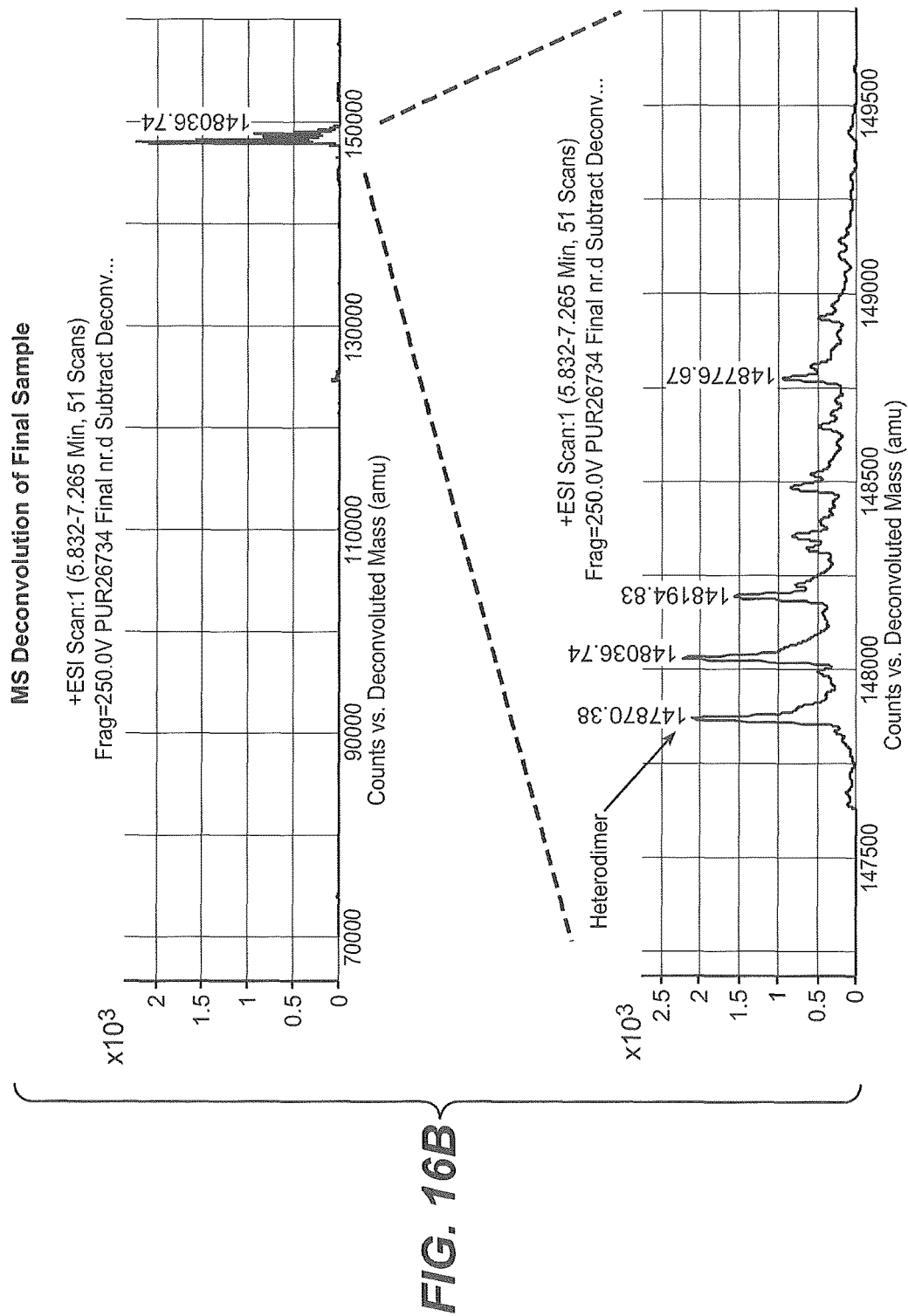
Figures 16C, 16D:
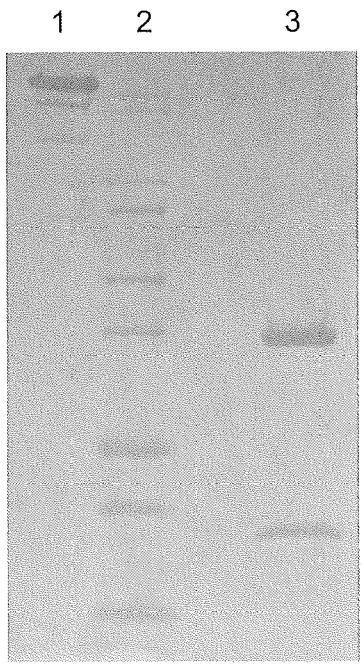
Figure 17:
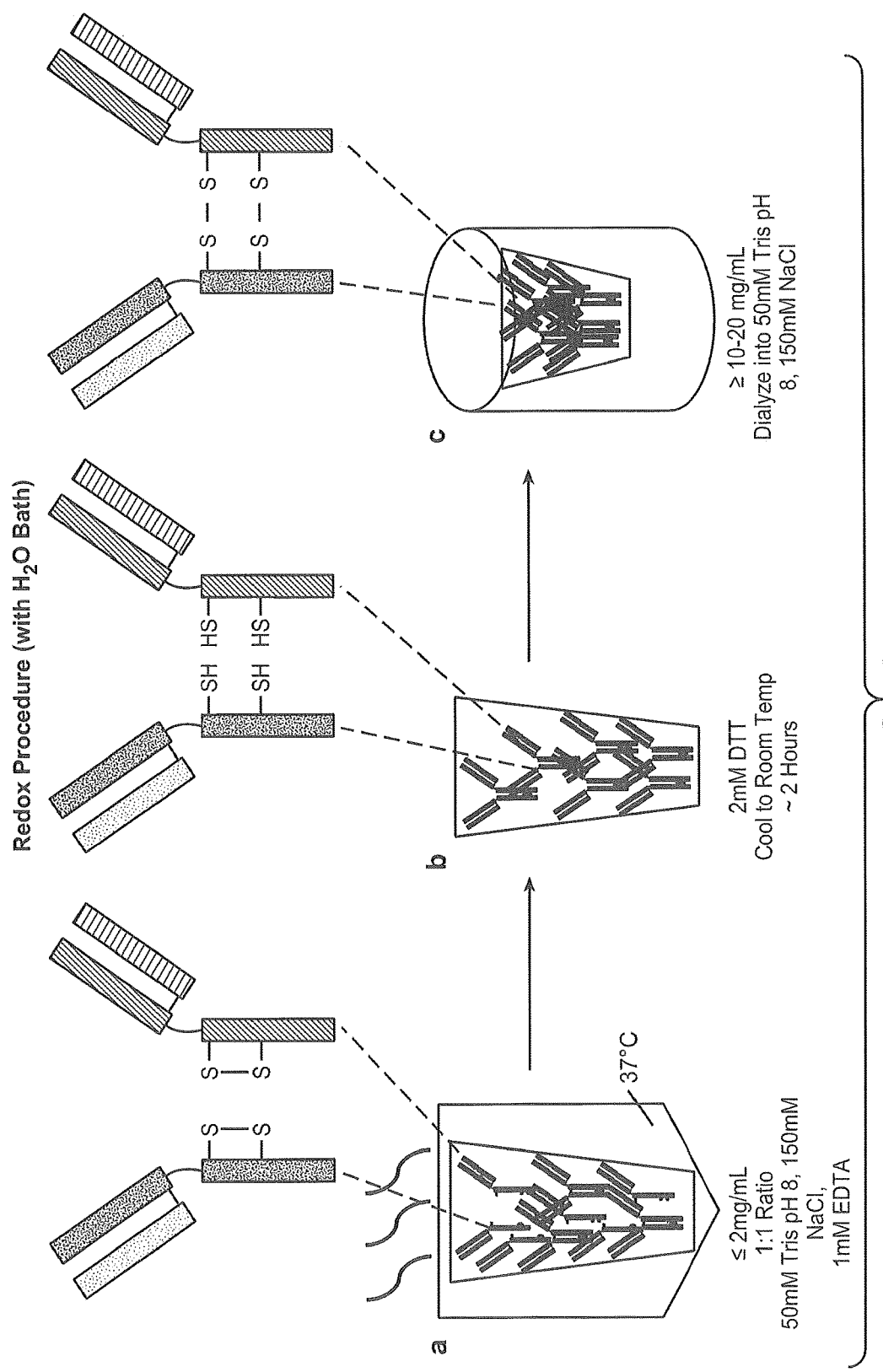
FIG. 17 is a schematic of redox procedure (with heat): a) sample is heated for an hour to allow cyclisation of disulfide bonds, b) then cooled and cysteines are reduced using 2 mM DTT for two hours, and c) then concentrated and cysteines are air oxidized by dialysis at room temperature.
Figure 18:
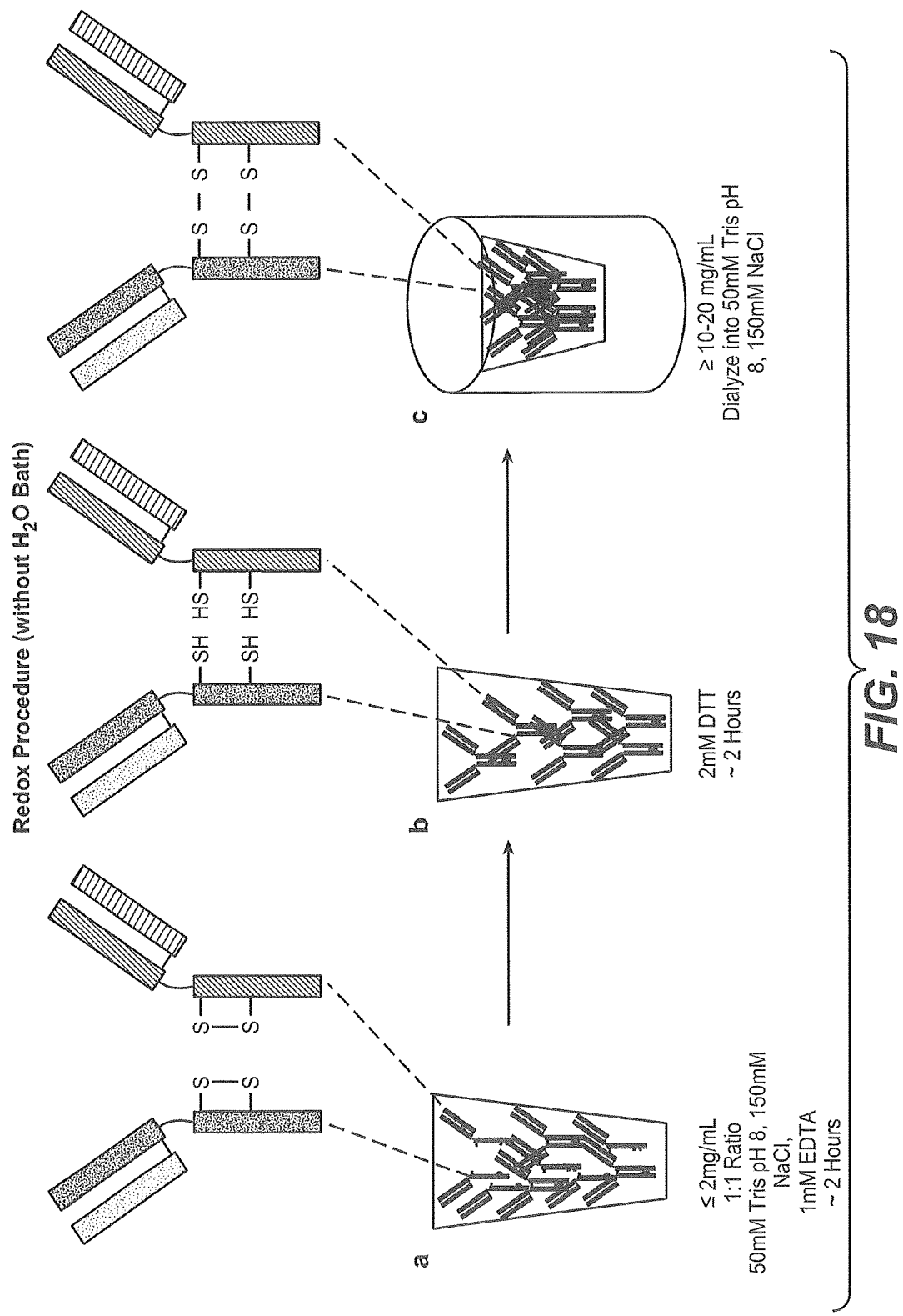
FIG. 18 is a schematic of redox procedure (without heat): a) sample is mixed for two hours, b) cysteines are reduced using 2 mM DTT for two hours, and c) then concentrated and cysteines are air oxidized while EDTA is removed by dialysis at room temperature
Figure 19B:
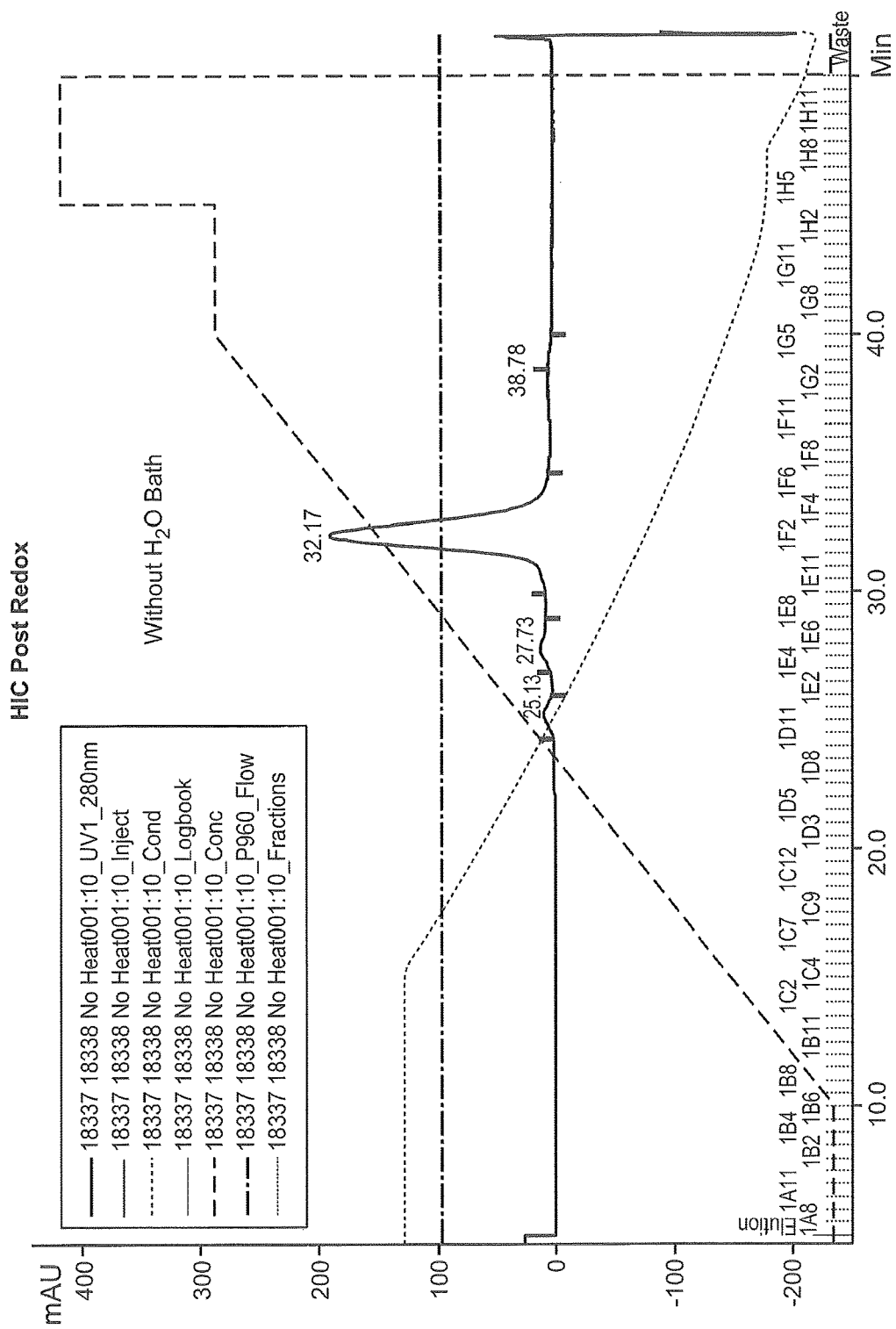
FIG. 19: Analytics of assembled bispecific A) HIC chromatogram using redox procedure with heating step B) HIC chromatogram using redox procedure without heating step.

FIGS. 12 & 13 show the in vivo activity of the anti-EGFR/c-met bispecific antibody in KP4 pancreatic xenograft model and A431 epidermoid carcinoma xenograft model, respectively. The bispecific antibody was able to inhibit the growth of the tumors in vivo for both models as compared with control animals that received only the vehicle as a treatment. The graphs indicate the tumor volume was decreased by administration of the bispecific antibody with the Linear Mixed Effects (LME) fitter tumor volume of 505 mm$^3$ in KP4 xenografts at 20 days after treatment compared to 1710 mm$^3$ for the vehicle only arm and 328 mm$^3$ in A431 xenografts after 20 days compared to 495 mm$^3$ in the vehicle only control. Overall there was a significant change in the AUC/day expressed as % TGI. For the bispecific antibody treatment in the KP4 xenografts, there was 85% tumor growth inhibition (TGI) and in the A431 xenograft models there was a 68% TGI.

Example 7

Heteromultimeric Protein Production Using CHO Cell Culture

This example illustrates the formation of heteromultimeric proteins from a culture comprising two host CHO cell populations.

Half-antibodies containing either the knob or hole mutations were generated in separate cultures by transiently expressing the heavy and light chains using constructs and techniques well known in the art. (See, for example, Ye et al., Biotechnol Bioeng. 2009 Jun. 15; 103(3):542-51.) Cells were cultured in 1 liter of media (see, for example, Wong et al., J. Biol. Chem. 2007 282(31):22953-22963) and harvested after 14 days.

Each half antibody was captured on a 5 mL MabSURE SELECT column. The column was then washed with 10 column volumes (CV) of the equilibration buffer followed by 10 CV of a sodium citrate low conductivity buffer (equilibration buffer consisting of 50 mM TRIS pH 8.0, 150 mM NaCl, 0.05% Triton X-100, 0.05% Triton X-114; low conductivity wash buffer consisting of 25 mM Sodium Citrate pH 6.0). Each arm was eluted with 0.15 M Sodium Acetate pH 2.7.

Each half antibody was dialyzed into 50 mM TRIS pH 8.0, 150 mM NaCl, 1 mM EDTA at a ratio of 1 to 300 at room temperature overnight. Each arm was then centrifuged, filtered using 0.22 micron cellulose acetate filters and the two arms mixed together at a ratio of 1 to 1 (the total concentration was less than 2 mg/mL). The mixture was then processed one of two ways as follows:

Redox (with water bath): The mixture was then heated in a water bath at 37° C. After an hour, the redox mixture was removed from the water bath and left to cool to room temperature. Once the mixture reached room temperature, freshly prepared reducing agent, dithiothreitol (DTT), was added to achieve a final concentration of 2 mM DTT. The mixture was left at room temperature for two hours, then concentrated using Amicon Ultracell centrifugal filters (10K) to 11 mg/mL and dialyzed into 50 mM TRIS pH 8.0, 150 mL NaCl (1:300) overnight.

Redox (no water bath): The mixture was left at room temperature for 3 hours, after which freshly prepared reducing agent, dithiothreitol (DTT), was added to achieve a final concentration of 2 mM DTT. The mixture was left at room temperature for two hours, concentrated using Amicon Ultracell centrifugal filters (10K) to 11 mg/mL, and dialyzed into 50 mM TRIS pH 8.0, 150 mL NaCl (1:300) overnight.

Following redox, the assembled material was purified on a 15 mL HIC ProPac 10 column using a 20 CV gradient similar to the previous section. The running buffer was 25 mM Potassium Phosphate, 0.7M Ammonium Sulfate pH 6.5 and the elution buffer was 25 mM Potassium Phosphate pH 6.5, 25% isopropanol. One mL fractions were collected and peak fractions were separated by 4-20% Tris-Glycine SDS PAGE to analyze purity and pooled accordingly. The pools were then concentrated using Amicon Ultracell centrifugal filters (10K) to around 1.5 mg/mL and dialyzed into 50 mM TRIS pH 8.0, 150 mM NaCl and 0.22 μm filtered.

The identity of each assembled bispecific was confirmed by Mass Spectrometry. Purity was analyzed by 4-20% Tris-Glycine SDS PAGE gel and bioanalyzer. Aggregate levels were determined by SEC-MALS.

Results are shown in FIGS. 14-19. This example demonstrates that bispecific antibodies can be produced using CHO host cells. One skilled in the art will recognize that the method can be used to produce other heteromultimeric proteins.

What is claimed is:

1. A method of preparing a heteromultimeric protein comprising a first antibody heavy chain paired with a first antibody light chain and a second antibody heavy chain paired with a second antibody light chain, and wherein the first and second antibody heavy chains are linked by at least one interchain disulfide bond, the method comprising the steps of:
   (a) culturing a first host cell comprising a first nucleic acid encoding the first antibody heavy chain and the first antibody light chain under conditions where a first half antibody comprising the first antibody heavy chain and the first antibody light chain is expressed;
   (b) culturing a second host cell comprising a second nucleic acid encoding the second antibody heavy chain and the first antibody light chain under conditions where a second half antibody comprising the second antibody heavy chain and the second antibody light chain is expressed;
   (c) combining cultures of the first and second host cells to produce a combined culture comprising the first host cells and second host cells, wherein the heteromultimeric protein is formed in the combined culture; and
   (d) recovering the heteromultimeric protein without prior recovery or purification of the first and second half antibodies from separate cultures.

2. The method of claim 1, wherein the first antibody heavy chain comprises a first heterodimerization domain and the second antibody heavy chain comprises a second heterodimerization domain.

3. The method of claim 1, wherein the first antibody heavy chain comprises a first Fc domain and the second antibody heavy chain comprises a second Fc domain.

4. The method of claim 3, wherein the first Fc domain and the second Fc domain meet at an interface, wherein the interface of the first Fc domain comprises a cavity, and wherein the interface of the second Fc domain comprises a protuberance which is positionable in the cavity in the interface of the first Fc domain.

5. The method of claim 2, wherein the first heterodimerization domain and the second heterodimerization domain comprise a leucine zipper.

6. The method of claim 2, wherein the first heterodimerization domain and the second heterodimerization domain comprise a coiled coil.

7. The method of claim 1, wherein said at least one interchain disulfide bond is in the hinge region of an antibody.

8. The method of claim 1, wherein said at least one interchain disulfide bond is between hinge regions of the first and second antibody heavy chains.

9. The method of claim 1, wherein the first and/or second antibody heavy chain comprises a $C_H$-domain or variant thereof.

10. The method of claim 1, wherein the first and/or second antibody heavy chain comprises an Fc region or variant thereof.

11. The method of claim 1, wherein the first antibody heavy chain and the first antibody light chain polypeptide form a first target binding arm, and wherein the second antibody heavy chain and the second antibody light chain form a second target binding arm.

12. The method of claim 1, wherein the first and second antibody heavy chains each comprise at least a portion of a human $C_H2$ and/or $C_H3$ domain.

13. The method of claim 1, wherein the first and second half antibodies are humanized.

14. The method of claim 1, wherein the first antibody heavy chain and first antibody light chain are encoded on separate expression plasmids.

15. The method of claim 1, wherein the first antibody heavy chain and first antibody light chain are encoded on the same expression plasmid.

16. The method of claim 1, wherein the first and second host cells are selected from the group consisting of prokaryotic cells, eukaryotic cells, mammalian cells and plant cells.

17. The method of claim 1, wherein the first and second host cells are prokaryotic cells.

18. The method of claim 17, wherein said prokaryotic cells are E. coli cells.

19. The method of claim 18, wherein said E. coli cells are lpp deficient.

20. The method of claim 1, wherein the first and second host cells are mammalian cells.

21. The method of claim 20, wherein said mammalian cells are CHO cells.

22. The method of claim 1, wherein the recovery step further comprises at least one purification step.

23. The method of claim 22, wherein the at least one purification step comprises:
(i) capturing said heteromultimeric protein on a column comprising Protein A,
(ii) eluting said heteromultimeric protein from said column, and
(iii) diluting said eluted heteromultimeric protein into a solution containing a chaotropic agent or mild detergent.

24. The method of claim 1, wherein the heteromultimeric protein is selected from the group consisting of an antibody, a bispecific antibody, a multispecific antibody, a one-armed antibody, a multispecific monovalent antibody, a bispecific maxibody, a monobody, an immunoadhesin, a peptibody, a bispecific peptibody, a monovalent peptibody, and an affibody.

25. The method of claim 24, wherein the heteromultimeric protein is an antibody.

26. The method of claim 24, wherein the heteromultimeric protein is a bispecific antibody.

27. The method of claim 24, wherein the heteromultimeric protein is a multispecific antibody.

28. The method of claim 24, wherein the heteromultimeric protein is a one-armed antibody.

29. The method of claim 25, wherein said antibody comprises a heavy chain constant domain and a light chain constant domain.

30. The method of claim 25, wherein said antibody is humanized.

31. The method of claim 25, wherein the antibody is a full-length antibody.

32. The method of claim 1, wherein the first antibody heavy chain and first antibody light chain are human.

33. The method of claim 25, wherein said antibody is human.

34. The method of claim 25, wherein the antibody is an antibody fragment comprising at least a portion of human $C_H2$ and/or $C_H3$ domain.

35. The method of claim 34, wherein said antibody fragment is an Fc fusion polypeptide.

36. The method of claim 26, wherein the bispecific antibody is selected from the group consisting of IgG, IgA and IgD.

37. The method of claim 36, wherein the bispecific antibody is IgG.

38. The method of claim 37, wherein the IgG is IgG1.

39. The method of claim 37, wherein the IgG is IgG2.

40. The method of claim 25, wherein the antibody is a therapeutic antibody.

41. The method of claim 25, wherein the antibody is an agonist antibody.

42. The method of claim 25, wherein the antibody is an antagonistic antibody.

43. The method of claim 25, wherein the antibody is a diagnostic antibody.

44. The method of claim 25, wherein the antibody is a blocking antibody.

45. The method of claim 25, wherein the antibody is a neutralizing antibody.

46. The method of claim 25, wherein the antibody is capable of binding to a tumor antigen.

47. The method of claim 46, wherein the tumor antigen is not a cell surface molecule.

48. The method of claim 46, wherein the tumor antigen is not a cluster differentiation factor.

49. The method of claim 25, wherein the antibody is capable of binding to a cluster differentiation factor.

50. The method of claim 25, wherein the antibody is capable of binding to a cell survival regulatory factor.

51. The method of claim 25, wherein the antibody is capable of binding specifically to a cell proliferation regulatory factor.

52. The method of claim 25, wherein the antibody is capable of binding to a molecule associated with tissue development or differentiation.

53. The method of claim 25, wherein the antibody is capable of binding to a cell surface molecule.

54. The method of claim 25, wherein the antibody is capable of binding to a lymphocyte.

55. The method of claim 26, wherein the first and second light chains of the bispecific antibody comprise different variable domain sequences.

56. The method of claim 39, wherein at least 40% of the first half-antibody and second half-antibody form said bispecific antibody.

57. The method of claim 26, wherein said bispecific antibody is capable of specifically binding two different antigens or two epitopes on the same antigen.

58. The method of claim 57, wherein the bispecific antibody is capable of specifically binding two different antigens.

59. The method of claim 1, wherein at least 40% of the first half antibody and second half antibody in the combined culture form the heteromultimeric protein.

60. The method of claim 22, wherein no more than 10% of the first and second half antibodies are present as monomers or homodimers prior to the step of purifying the heteromultimeric protein.

61. The method of claim 1, wherein the first and second antibody heavy chains comprise different variable domain sequences and wherein the first and second antibody light chains comprise different variable domain sequences.

62. The method of claim 1, wherein the first antibody heavy chain and first antibody light chain are linked to each other via disulfide bonds, and wherein the second antibody heavy chain and second antibody light chain are linked to each other via disulfide bonds.

63. The method of claim 1, wherein the difference in pI values between the first half antibody and second half antibody is at least 0.5.

64. The method of claim 1, further comprising a step of adding a reductant.

65. The method of claim 1, wherein the first and second half antibodies are secreted into culture medium of the combined culture comprising the first host cells and second host cells.

66. The method of claim 65, wherein the heteromultimeric protein is formed in the culture medium of the combined culture comprising the first host cells and second host cells.

67. The method of claim 1, further comprising disrupting the cell membrane in the combined culture comprising the first host cells and second host cells to form the heteromultimeric protein.

68. The method of claim 67, wherein disrupting the cell membrane is selected from the group consisting of permeabilizing the cell membrane and cell membrane disintegration.

69. The method of claim 68, wherein disrupting the cell membrane is selected from the group consisting of enzymatic lysis, cell lysis, sonication, osmotic shock, passage through a microfluidizer, addition of EDTA, various detergents, solvents (such as toluene, dimethyl sulfoxide, etc), surfactants (such as Triton-X 100, Tween 20, etc), hypotonic buffers, use of freeze/thaw techniques, electroporation, and passage through a stainless steel ball homogenizer.

70. The method of claim 1, wherein the first and second nucleic acids are recombinant nucleic acids.

71. The method of claim 3, wherein the first Fc domain and the second Fc domain meet at an interface, wherein the interface of the second Fc domain comprises a cavity, and wherein the interface of the first Fc domain comprises a protuberance which is positionable in the cavity in the interface of the second Fc domain.

72. The method of claim 1, wherein the second antibody heavy chain and second antibody light chain are encoded on separate expression plasmids.

73. The method of claim 1, wherein the second antibody heavy chain and second antibody light chain are encoded on the same expression plasmid.

74. The method of claim 1, wherein the second antibody heavy chain and second antibody light chain are human.

75. The method of claim 67, wherein the first and second host cells are prokaryotic cells.

* * * * *

UNITED STATES PATENT AND TRADEMARK OFFICE
CERTIFICATE OF CORRECTION

Page 1 of 1

PATENT NO. : 9,637,557 B2
APPLICATION NO. : 13/092708
DATED : May 2, 2017
INVENTOR(S) : Justin Scheer et al.

It is certified that error appears in the above-identified patent and that said Letters Patent is hereby corrected as shown below:

In the Claims

At Column 89, Claim number 1, Line number 67, please replace "first" with --second--.

Signed and Sealed this
Nineteenth Day of December, 2017

Joseph Matal
*Performing the Functions and Duties of the*
*Under Secretary of Commerce for Intellectual Property and*
*Director of the United States Patent and Trademark Office*